US009676756B2

(12) United States Patent
Bauer et al.

(10) Patent No.: US 9,676,756 B2
(45) Date of Patent: Jun. 13, 2017

(54) SUBSTITUTED PYRIMIDINYL KINASE INHIBITORS

(71) Applicant: PORTOLA PHARMACEUTICALS, INC., South San Francisco, CA (US)

(72) Inventors: Shawn M. Bauer, Pacifica, CA (US); Zhaozhong J. Jia, San Mateo, CA (US); Yonghong Song, Foster City, CA (US); Anjali Pandey, Fremont, CA (US)

(73) Assignee: PORTOLA PHARMACEUTICALS, INC., South San Francisco, CA (US)

( * ) Notice: Subject to any disclaimer, the term of this patent is extended or adjusted under 35 U.S.C. 154(b) by 0 days.

(21) Appl. No.: 14/434,075

(22) PCT Filed: Oct. 8, 2013

(86) PCT No.: PCT/US2013/063942
§ 371 (c)(1),
(2) Date: Apr. 7, 2015

(87) PCT Pub. No.: WO2014/058921
PCT Pub. Date: Apr. 17, 2014

(65) Prior Publication Data
US 2015/0259328 A1    Sep. 17, 2015

Related U.S. Application Data

(60) Provisional application No. 61/711,170, filed on Oct. 8, 2012.

(51) Int. Cl.
| *C07D 405/14* | (2006.01) |
|---|---|
| *C07D 401/12* | (2006.01) |
| *C07D 401/14* | (2006.01) |
| *C07D 403/12* | (2006.01) |
| *A61K 31/506* | (2006.01) |
| *C07D 239/48* | (2006.01) |

(52) U.S. Cl.
CPC ......... *C07D 405/14* (2013.01); *C07D 239/48* (2013.01); *C07D 401/12* (2013.01); *C07D 401/14* (2013.01); *C07D 403/12* (2013.01)

(58) Field of Classification Search
None
See application file for complete search history.

(56) References Cited

U.S. PATENT DOCUMENTS

| 6,080,747 | A | 6/2000 | Uckun et al. |
|---|---|---|---|
| 6,080,748 | A | 6/2000 | Uckun et al. |
| 6,133,305 | A | 10/2000 | Tang et al. |
| 6,177,433 | B1 | 1/2001 | Uckun et al. |
| 6,210,654 | B1 | 4/2001 | Ihle et al. |
| 6,313,130 | B1 | 11/2001 | Uckun et al. |
| 6,316,635 | B1 | 11/2001 | Tang et al. |
| 6,433,018 | B1 | 8/2002 | Siddiqui et al. |
| 6,486,185 | B1 | 11/2002 | McMahon et al. |
| 6,506,763 | B2 | 1/2003 | Tang et al. |
| 6,528,509 | B1 | 3/2003 | Hale et al. |
| 6,593,357 | B1 | 7/2003 | Green et al. |
| 6,608,048 | B2 | 8/2003 | Tsou et al. |
| 6,610,688 | B2 | 8/2003 | Liang et al. |
| 6,635,651 | B2 | 10/2003 | Uckun et al. |
| 6,677,368 | B2 | 1/2004 | Cui et al. |
| 6,683,082 | B2 | 1/2004 | Tang et al. |
| 6,696,448 | B2 | 2/2004 | Tang et al. |
| 6,699,865 | B2 | 3/2004 | Hale et al. |
| 6,777,417 | B2 | 8/2004 | Liang et al. |
| 6,784,195 | B2 | 8/2004 | Hale et al. |
| 6,815,439 | B2 | 11/2004 | Harris et al. |
| 6,825,190 | B2 | 11/2004 | Moon et al. |
| 6,949,580 | B2 | 9/2005 | Hale et al. |
| 6,969,760 | B2 | 11/2005 | Ihle et al. |
| 6,998,391 | B2 | 2/2006 | Lyons et al. |
| 7,056,944 | B2 | 6/2006 | Hale et al. |
| 7,074,793 | B2 | 7/2006 | Hukdins et al. |
| 7,105,529 | B2 | 9/2006 | Davis et al. |
| 2001/0007033 | A1 | 7/2001 | Tang et al. |
| 2002/0115173 | A1 | 8/2002 | Ben-Sasson et al. |
| 2002/0137141 | A1 | 9/2002 | Ben-Sasson et al. |
| 2003/0149064 | A1 | 8/2003 | Pease |
| 2003/0236244 | A1 | 12/2003 | Ledford |
| 2004/0029902 | A1 | 2/2004 | Singh et al. |
| 2004/0102455 | A1 | 5/2004 | Burns |
| 2004/0142404 | A1 | 7/2004 | Wilks |
| 2004/0147507 | A1 | 7/2004 | Ledeboer |
| 2004/0214817 | A1 | 10/2004 | Pierce |
| 2005/0234049 | A1 | 10/2005 | Singh et al. |

(Continued)

FOREIGN PATENT DOCUMENTS

| WO | 95/03701 A1 | 2/1995 |
|---|---|---|
| WO | 99/15500 A1 | 4/1999 |

(Continued)

OTHER PUBLICATIONS

Berge, S.M. et al., "Pharmaceutical Salts," Journal of Pharmaceutical Science, 66:1-19, 1977.
Braselmann et al., "R406, an Orally Available Spleen Tyrosine Kinase Inhibitor Blocks Fc Receptor Signaling and Reduces Immune Complex-Mediated Inflammation," J Pharmacol Exp Ther 319(3): 998-1008 (2006).
Burnett and Knapper, "Targenting Treatment in AML," Hematology Am Soc Hematol Educ Program 2007: 429-34 (2007).
Catlett-Falcone et al., "Constitutive Activation of Stat3 Signaling Confers Resistance to Apoptosis in Human U266 Myeloma Cells," (1999), Immunity 10:105-115.
Chen, L., et.al, "Protein tyrosine phosphatase receptor-type O truncated (PTPROt) regulates SYK phosphorylation, proximal B-cell-receptor signaling, and cellular proliferation," Blood, 2006; 108:3428-3433.

(Continued)

*Primary Examiner* — Michael Barker
(74) *Attorney, Agent, or Firm* — Mintz, Levin, Cohn, Ferris, Glovsky and Popeo, P.C.

(57) ABSTRACT

Provided are substituted pyrimidinyl compounds for inhibition of JAK and/or Syk kinase, pharmaceutical compositions thereof, methods for inhibiting JAK and/or Syk kinase activity, and methods for treating conditions mediated at least in part by JAK and/or Syk kinase activity.

23 Claims, No Drawings

(56) References Cited

U.S. PATENT DOCUMENTS

2007/0060603 A1    3/2007    Singh et al.
2009/0318407 A1    12/2009    Bauer et al.

FOREIGN PATENT DOCUMENTS

| | | |
|---|---|---|
| WO | 00/00202 A1 | 1/2000 |
| WO | 00/10981 A1 | 3/2000 |
| WO | 00/39101 | 7/2000 |
| WO | 00/47583 A1 | 8/2000 |
| WO | 00/51587 A2 | 9/2000 |
| WO | 00/55159 A2 | 9/2000 |
| WO | 01/42246 A2 | 6/2001 |
| WO | 01/45641 A2 | 6/2001 |
| WO | 01/52892 A2 | 7/2001 |
| WO | 01/56993 A2 | 8/2001 |
| WO | 01/57022 A2 | 8/2001 |
| WO | 01/72758 A1 | 10/2001 |
| WO | 02/00661 A1 | 1/2002 |
| WO | 02/43735 A1 | 6/2002 |
| WO | 02/48336 A2 | 6/2002 |
| WO | 02/59110 | 8/2002 |
| WO | 02/060492 A1 | 8/2002 |
| WO | 02/060927 A1 | 8/2002 |
| WO | 02/096909 A1 | 12/2002 |
| WO | 02/102800 A1 | 12/2002 |
| WO | 03/002542 | 1/2003 |
| WO | 03/020698 A2 | 3/2003 |
| WO | 03/030909 | 4/2003 |
| WO | 03/048162 A1 | 6/2003 |
| WO | 03/063794 A2 | 8/2003 |
| WO | 03/066601 | 8/2003 |
| WO | 03/074515 | 9/2003 |
| WO | 03/101989 A1 | 12/2003 |
| WO | 03/106416 | 12/2003 |
| WO | 2004/014382 A1 | 2/2004 |
| WO | 2004/016597 A2 | 2/2004 |
| WO | 2004/041789 A1 | 5/2004 |
| WO | 2004/041810 A1 | 5/2004 |
| WO | 2004/041814 A1 | 5/2004 |
| WO | 2004/046112 A2 | 6/2004 |
| WO | 2004/046118 | 6/2004 |
| WO | 2004/046120 A2 | 6/2004 |
| WO | 2004/047843 A1 | 6/2004 |
| WO | 2004/058749 A1 | 7/2004 |
| WO | 2004/058753 A1 | 7/2004 |
| WO | 2004/085388 A2 | 10/2004 |
| WO | 2004/092154 A1 | 10/2004 |
| WO | 2005/009957 A1 | 2/2005 |
| WO | 2005/016344 A1 | 2/2005 |
| WO | 2005/016893 | 2/2005 |
| WO | 2005/016894 | 2/2005 |
| WO | 2005/028475 A2 | 3/2005 |
| WO | 2005/033107 A1 | 4/2005 |
| WO | 2005/037800 | 4/2005 |
| WO | 2005/066156 | 7/2005 |
| WO | 2005/122294 A1 | 12/2005 |

OTHER PUBLICATIONS

Chen, Monti et al., "SYK-dependent tonic B-cell receptor signaling is a rational treatment target in diffuse large B-cell lymphoma," Blood 111(4): 2230-7 (2008).

Chen, R. et al., "MicroRNA regulation in mantle cell lymphoma," Journal of Clinical Oncology, 2007 ASCO Annual Meeting Proceedings (Post-Meeting Edition).vol. 25, No. 18S (Jun. 20 Supplement), 2007: 8056.

Cheng, Alec et al., "SYK tyrosine kinase required formouse viability and B-cell development," Nature 378(6554):303-6 (1995).

Couture, C. et al., "Activation of p56lck by p72,k through Physical Association and N-Terminal Tyrosine Phosphorylationt," Mol. Cell. Biol., 14:5249-5258, 1994.

Couture, C. et al., "p56lck-independent activation and tyrosine phosphorylation of p72sYk by T-cell antigen receptor/CD3 stimulation," Proc. Natl. Acad. Sci. USA, 91:5301-5305, 1994.

Crow, A.R. et al., "Inhibition of Immune Thrombocytopenic Purpura (ITP) by an Orally Bioavailabl Inhibitor of Syk Kinase Activity," Blood, 106:abstract 2165, 2005.

Crowley, M.T. et al., "A Critical Role for Syk in Signal Transduction and Phagocytosis Mediated by Fc g Receptors on Macrophages," J. Exp. Med., 186:1027-1039, 1997.

Frank, "STAT Signaling in the Pathogenesis and Treatment of Cancer," (1999), Mol. Med. 5:432:456.

Garcia-Bustos et al., "PIK1, an essential phosphatidylinositol 4-kinase associated with the yeast nucleus," (1994), Embo J. 13:2352-2361.

Gobessi et al., "Constitutive activation of the protein tyrosine kinase Syk in Chronic Lymphocytic Leukemia B-cells", *Blood* (ASH Annual Meeting Abstracts) 2007 110: Abstract 1123.

Gururajan et al., "Cutting Edge: Constitutive B Cell Receptor Signaling Is Critical for Basal Growth of B Lymphoma," 2006, 176:5715-5719.

Gururajan et al., "Spleen Tyrosine Kinase (Syk), a Novel Target of Curcumin, Is Required for B Lymphoma Growth," J Immunol 178(1): 111-21 (2007).

Hanks & Hunter, "The eukaryotic protein kinase superfamily: kinase (catalytic) domain structure and classification," (1995), FASEB J. 9:576-596.

Heinrich, Griffith et al., "Inhibition of c-kit receptor tyrosine kinase activity by STI 571, a selective tyrosine kinase inhibitor," Blood 96(3): 925-32 (2000).

Hiles et al., "Phosphatidylinositol 3-Kinase: Structure and Expression of the 110 kd Catalytic Subunit," (1992), Cell 70:419-429.

Hutchcroft, J E. et al., "Association of the 72-kDa Protein-tyrosine Kinase PTK72 with the B Cell Antigen Receptor," J. Biol. Chem., 267:8613-8619, 1992.

Irish et al., "Altered B-cell receptor signaling kinetics distinguish human follicular lymphoma B cells from tumor-infiltrating nonmalignant B cells," *Blood*, 2006; 108: 3135-3142.

Jumaa, Hendriks et al., "B cell signaling and tumorigenesis," Annu Rev Immunol 23: 415-45 (2005).

Kirken, "Targeting JAK3 for Immune Suppression and Allograft Acceptance," (2001), Transpl. Proc. 33:3268-3270.

Knighton et al., "Crystal structure of the catalytic subunit of cyclic adenosine monophosphate-dependent protein kinase," (1991), Science 253:407-414.

Kraus et al., "Survival of Resting Mature B Lymphocytes Depends on BCR Signaling via the Igα/β Heterodimer," Cell 117(6): 787-800 (2004).

Kuno, Y. et.al., "Constitutive kinase activation of the *TEL-Syk* fusion gene in myelodysplastic syndrome with t(9;12)(q22;p12)," Blood, 2001; 97:1050-1055.

Kunz et al., "Target of Rapamycin in Yeast, TOR2, Is an Essential Phosphatidylinositol Kinase Homolog Required for G1 Progression," (1993), Cell 73:585-596.

Kuppers, R., "Mechanisms of B-Cell Lymphoma Pathogenesis," Nat Rev Cancer, 2005; 5:251-262.

Lam, Kuhn et al., "In Vivo Ablation of Surface Immunoglobulin on Mature B Cells by Inducible Gene Targeting Results in Rapid Cell Death," Cell 90(6): 1073-83 (1997).

Latour, S. et al., "Regulation of T-Cell Antigen Receptor Signalling by Syk Tyrosine Protein Kinase," Mol Cell Biol., 17:4434-4441, 1997.

Law, D.A. et al., "Genetic and Pharmacological Analyses of Syk Function in allbb3 Signaling in Platelets," Blood, 93:2645-2652, 1999.

Leonard et al., "Molecular mechanisms in allergy and clinical immunology." (2000), J. Allergy Clin. Immunol. 105:877-888.

Leseux, L. et. al., "Syk-dependent mTOR activation in follicular lymphoma cells," Blood, 2006; 108:4156-4162.

Linfeng, Chen et al., "SYK-dependent tonic B-cell receptor signaling is a rational treatment target in diffuse large B-cell lymphoma," *Blood*, Feb. 2008; 111: 2230-2237.

Malaviya et al., Targeting Janus Kinase 3 in Mast Cells Prevents Immediate Hypersensitivity Reactions and Anaphylaxis, (1999), J. Biol. Chem. 274:27028-27038.

(56) References Cited

OTHER PUBLICATIONS

Malaviya et al., "Genetic and Biochemical Evidence for a Critical Role of Janus Kinase (JAK)-3 in Mast Cell-Mediated Type I Hypersensitivity Reactions," (1999), Biochem. Biophys. Res. Commun. 257:807-813.
Muller-Ladner et al., "Activation of the IL-4 STAT Pathway in Rheumatoid Synovium," (2000), J. Immunol. 164:3894-3901.
Nielsen et al., "Constitutive activation of a slowly migrating isoform of Stat3 in mycosis fungoides: Tyrphostin AG490 inhibits Stat3 activation and growth of mycosis fungoides tumor cell lines," (1997), Prac. Natl. Acad. Sci. USA 94:6764-6769.
Poole, A. et al., "The Fc receptor g-chain and the tyrosine kinase Syk are essential for activation of mouse platelets by collagen," EMBO J., 16:2333-2341, 1997.
Reilly, M.P., "Heparin-induced thrombocytopenia/thrombosis in a transgenic mouse model requires human platelet factor 4 and platelet activation through FcgRIIA," Blood, 98:2442-2447, 2001.
Rinaldi, A. et.al, "Genomic and expression profiling identifies the B-cell associated tyrosine kinase Syk as a possible therapeutic target in mantle cell lymphoma," Br. J. Haematol., 2006; 132:303-316.
Rolli, Gallwitz et al. "Amplification of B Cell Antigen Receptor Signaling by a Syk/ITAM Positive Feedback Loop," Mol Cell 10(5): 1057-69 (2002).
Rossi, A.B. et al., "Identification of the Syk kinase inhibitor R112 by a human mast cell screen," J Allergy Clin. Immunol., 118:749-755, 2006.
Seidel et al., "Pharmaceutical intervention in the JAK/STAT signaling pathway," (2000), Oncogene 19:2645-2656.
Sudbeck et al., "Structure-based Design of Specific Inhibitors of Janus Kinase 3 as Apoptosis-inducing Antileukemic Agents," (1999), Clin. Cancer Res. 5:1569-1582.
Suzuki et al., (2000), *Blood* 96:2172-2180.
Takata, M. et al., "Tyrosine kinases Lyn and Syk regulate B cell receptorcoupled Ca2+ mobilization through distinct pathways," EMBO J., 13:1341-1349, 1994.
Trieu et al., "A Specific Inhibitor of Janus Kinase-3 Increases Survival in a Transgenic Mouse Model of Amyotrophic Lateral Sclerosis," (2000), Biochem Biophys. Res. Commun. 267:22-25.
Underhill, D.M and Goodridge, H. S., "The many faces of ITAMs," *Trends Immunol.*, 28:66-73, 2007.
Wossning, T. et al., "Deregulated Syk inhibits differentiation and induces growth factor-independent proliferation of pre-B cells," JEM, 2006; 203:2829-2840.
Yousefi, S. et al., "Requirement of Lyn and Syk Tyrosine Kinases for the Prevention of Apoptosis by Cytokinesin Human Eosinophils," J. E. Med., 183:1407-1414, 1996.
Yu et al., "Constitutive Activation of the Janus Kinase STAT Pathway in T Lymphoma Overexpressing the Lck Protein Tyrosine Kinase," (1997), J. Immunol. 159:5206-5210.

SUBSTITUTED PYRIMIDINYL KINASE INHIBITORS

CROSS REFERENCE TO RELATED APPLICATIONS

This application is a National Stage Entry of PCT/US2013/063942, filed Oct. 8, 2013, and claims the benefit of U.S. Provisional Patent Application No. 61/711,170, filed Oct. 8, 2012; the entire disclosures of which are incorporated herein by reference.

BACKGROUND OF THE INVENTION

This invention is directed to pyrimidine-5-carboxamide compounds that act as inhibitors of spleen tyrosine kinase (Syk) and/or JAK kinases. This invention is also directed to pharmaceutical compositions containing the pyrimidine-5-carboxamide compounds and methods of using the compounds or compositions to treat to treat cardiovascular disease, inflammatory disease, autoimmune disease, and/or cell proliferative disorder. The invention is also directed to methods of making the compounds described herein.

STATE OF THE ART

Protein kinases constitute a large family of structurally related enzymes that are responsible for the control of a variety of signal transduction processes within cells (see. e.g., Hardie and Hanks, The Protein Kinase Facts Book, I and II, Academic Press, San Diego, Calif., 1995). Protein kinases are thought to have evolved from a common ancestral gene due to the conservation of their structure and catalytic function. Almost all kinases contain a similar 250-300 amino acid catalytic domain. The kinases can be categorized into families by the substrates they phosphorylate (e.g., protein-tyrosine, protein-serine/threonine, lipids, etc.). Sequence motifs have been identified that generally correspond to each of these families (see, e.g., Hanks & Hunter, (1995), FASEB J. 9:576-596; Knighton et al., (1991), Science 253:407-414; Hiles et al., (1992), Cell 70:419-429; Kunz et al., (1993), Cell 73:585-596; Garcia-Bustos et al., (1994). EMBO J. 13:2352-2361).

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies, asthma, Alzheimer's disease and hormone-related diseases. As a consequence, there have been substantial efforts in medicinal chemistry to find inhibitors of protein kinases for use as therapeutic agents.

Immunoreceptor tyrosine activation motif (ITAM)-mediated signaling has emerged as a primary event in signaling pathways responsible for human pathologies. ITAM-mediated signaling is responsible for relaying activation signals initiated at classical immune receptors such as T-cell receptors, B-cell receptors, Fc receptors in immune cells and at GPVI and FcγRIIa in platelets to downstream intracellular molecules such as Syk and ZAP-70 (Underhill, D. M and Goodridge, H. S., Trends Immunol., 28:66-73, 2007).

The binding of a ligand to an ITAM-containing receptor triggers signaling events that allows for the recruitment of proteins from a family of nonreceptor tyrosine kinases called the Src family. These kinases phosphorylate tyrosine residues within the ITAM sequence, a region with which the tandem SH2 domains on either Syk or ZAP-70 interact.

Syk, along with Zap-70, is a member of the Syk family of protein tyrosine kinases. The interaction of Syk or ZAP-70 with diphosphorylated ITAM sequences induces a conformation change in the kinases that allows for tyrosine phosphorylation of the kinase itself. Phosphorylated Syk family members activate a multitude of downstream signaling pathway proteins, which include Src homology 2 (SH2) domain containing leukocyte-specific phosphoprotein of 76 kDa (SLP-76), Linker of Activation of T-cells (LAT) and PLC (phospholipase C)γ2.

Human pathologies attributed to dysfunctional ITAM-mediated signaling include autoimmune diseases such as rheumatoid arthritis, systemic lupus, multiple sclerosis, hemolytic anemia, immune-thrombocytopenia purpura, and heparin-induced thrombocytopenia and arteriosclerosis. Interestingly, many of the above mentioned diseases are thought to occur through crosslinking of Fc receptors by antibodies that, via Syk, activate a signaling cascade in mast, basophil and other immune cells that result in the release of cell mediators responsible for inflammatory reactions. The release of mediators and the production of cytokines in IgE stimulation-dependent allergic and inflammatory reactions from mast cells and basophiles can be controlled by inhibiting the tyrosine kinase activity of Syk (Rossi, A. B. et al., J Allergy Clin Immunol., 118:749-755, 2006). In immune-thrombocytopenia, antibody bound platelets are cleared by the spleen by an Fc receptor/ITAM/Syk-mediated process (Crow, A. R. et al., Blood, 106:abstract 2165, 2005). Drug-induced thrombocytopenia, caused by heparin-platelet factor 4 immune complexes that activate platelet FcγRIIa, also involve Syk signaling downstream of receptor engagement (Reilly, M. P., Blood, 98:2442-2447, 2001).

Platelet agonists induce inside-out integrin signaling resulting in fibrinogen binding and platelet aggregation. This initiates outside-in signaling, which produces further stimulation of platelets. Syk is activated during both phases of integrin signaling, and inhibition of Syk is shown to inhibit platelet adhesion to immobilized proteins (Law, D. A. et al., Blood, 93:2645-2652, 1999). Release of arachidonic acid and serotonin and platelet aggregation induced by collagen are markedly inhibited in platelets derived from Syk deficient mouse (Poole, A. et al., EMBO J., 16:2333-2341, 1997). Thus Syk inhibitors may also possess anticoagulation action.

Because of the role Syk plays in Ig-induced platelet activations, it is likely to be important in arteriosclerosis and restenosis. Arteriosclerosis is a class of diseases characterized by the thickening and hardening of the arterial walls of blood vessels. Although all blood vessels are susceptible to this serious degenerative condition, the aorta and the coronary arteries serving the heart are most often affected. Arteriosclerosis is of profound clinical importance since it can increase the risk of heart attacks, myocardial infarctions, strokes, and aneurysms.

The traditional treatment for arteriosclerosis includes vascular recanalization procedures for less-serious blockages and coronary bypass surgery for major blockages. A serious shortcoming of intravascular procedures is that, in a significant number of treated individuals, some or all of the treated vessels restenose (i.e., re-narrow). For example, restenosis of an atherosclerotic coronary artery after PTCA occurs in 10-50% of patients undergoing this procedure and subsequently requires either further angioplasty or a coronary artery bypass graft. Furthermore, restenosis of an atherosclerotic coronary artery after stenting occurs in 10-20% of patients undergoing this procedure and subsequently requires repeat treatments to maintain adequate blood flow through the affected artery. Restenosis generally occurs in a relatively brief time period, e.g., roughly less than six months, after treatment.

While the exact hormonal and cellular processes promoting restenosis have not been determined, restenosis is thought to be due in part to mechanical injury to the walls of the blood vessels caused by the balloon catheter or other intravascular device. For example, the process of PTCA, in addition to opening the obstructed artery, also injures resident coronary arterial smooth muscle cells (SMCs). In response to this injury, adhering platelets, infiltrating macrophages, leukocytes, or the smooth muscle cells themselves release cell-derived growth factors such as platelet-derived growth factor (PDGF), with subsequent proliferation and migration of medial SMCs through the internal elastic lamina to the area of the vessel intima. Further proliferation and hyperplasia of intimal SMCs and, most significantly, production of large amounts of extracellular matrix over a period of three to six months results in the filling-in and narrowing of the vascular space, which is sufficient to significantly obstruct blood flow.

In addition to the role Syk plays in Ig-induced platelet activations, Syk plays a very important role in collagen-mediated signaling. The primary adhesive protein responsible for platelet adhesion and activation is collagen. Collagen is a filamentous protein contained within the fibrotic caps of atheromas, and it becomes exposed to blood during plaque rupture. Collagen functions initially by binding von Willebrand factor, which tethers platelets through binding platelet membrane GPIb. Collagen functions secondarily by engaging the two collagen receptors on platelets, GPVI and integrin $\alpha 2\beta 1$.

GPVI exists in platelet membranes as a complex with FcRγ, an interaction required for the expression of GPVI. Activation of FcγRIIa on platelets results in platelet shape change, secretion and thrombosis. Signaling by the GPVI/FcRγ complex is initiated by tyrosine phosphorylation of the ITAM domain of FCRγ followed by the recruitment of Syk. Activation of GPVI leads to induction of multiple platelet functions including: activation of integrins $\alpha 2\beta 1$ to achieve firm platelet adhesion, and GP IIb-IIIa, which mediates platelet aggregation and thrombosis growth; platelet secretion, allowing for the delivery of inflammatory proteins such as CD40L, RANTES and TGFβ to the vessel wall; and the expression of P-selectin, which allows for the recruitment of leukocytes. Therefore, it is believed that Syk inhibitors can inhibit thrombotic events mediated by platelet adhesion, activation and aggregation.

It has been reported that the tyrosine phosphorylation of intracellular protein (activation) induced by stimulation of a receptor for IgG antibody, FcγR, and the phagocytosis mediated by FcγR are considerably inhibited in macrophages derived from Syk deficient mouse (Crowley. M. T. et al., *J. Exp. Med.*, 186:1027-1039, 1997). This suggests that Syk has a markedly important role in the FcγR-mediated phagocytosis of macrophages. Therefore, it is believed that Syk inhibitors can inhibit cell or tissue damage induced by antibody-dependent cellular cytotoxicity (ADCC).

It has also been reported that an antisense oligonucleotide of Syk suppresses the apoptosis inhibition of eosinophils induced by GM-CSF (Yousefi, S. et al., *J. E. Med.*, 183: 1407-1414, 1996), showing that Syk is essential for the life-extending signal of eosinophils caused by GM-CSF and the like. Since life extension of eosinophils is closely related to the transition of diseases into a chronic state in allergic disorders, such as asthma, Syk inhibitors can also serve as therapeutic agents for chronic eosinophilic inflammation.

Syk is important for the activation of B-cells via a B-cell antigen receptor and is involved in the phosphatidylinositol metabolism and increase in the intracellular calcium concentration caused by the antigen receptor stimulation (Hutchcroft, J E. et al., *J. Biol. Chem.*, 267:8613-8619, 1992; and Takata, M. et al., *EMBO J.*, 13:1341-1349, 1994). Thus, Syk inhibitors may be used to control the function of B-cells and are, therefore, expected to serve as therapeutic agents for antibody-related diseases.

Syk binds to a T-cell antigen receptor, quickly undergoes tyrosine phosphorylation through crosslinking of the receptor and synergistically acts upon intracellular signals mediated by Src tyrosine kinases such as Lck (Couture, C. et al., *Proc. Natl. Acad. Sci. USA,* 91:5301-5305, 1994; and Couture, C. et al., *Mol. Cell. Biol.*, 14:5249-5258, 1994). Syk is present in mature T-cell populations, such as intraepithelial γδ T-cells and naïve αβ T-cells, and has been reported to be capable of phosphorylation of multiple components of the TCR signaling cascade (Latour, S. et. al., *Mol Cell Biol.*, 17:4434-4441, 1997). As a consequence, Syk inhibitors may serve as agents for inhibiting cellular immunity mediated by T-cell antigen receptor.

Recent comparative genomic hybridization studies have identified Syk as another gene important in the pathogenesis of mantle cell lymphoma (MCL) (Chen, R. et al. *Journal of Clinical Oncology,* 2007 ASCO Annual Meeting Proceedings (Post-Meeting Edition). Vol 25, No 18S (June 20 Supplement), 2007: 8056). MCL represents 5-10% of all non-Hodgkins lymphomas, and it is a difficult form of lymphoma to treat. It has the worst prognosis among the B-cell lymphomas with a median survival of three years. It has been reported that Syk is overexpressed in MCL (Rinaldi, A, et. al. *Br. J. Haematol.*, 2006; 132:303-316) and that Syk mediates mTOR (mammalian target of Rapamycin) survival signals in follicular, mantel cell, Burkitt's, and diffuse large B-cell non-Hodgkin's lymphomas (Leseux, L. et. al, *Blood,* 2006; 108:4156-4162).

Several lines of evidence suggest that many B-cell lymphomas depend upon B-cell receptor (BCR)-mediated survival signals. BCR signaling induces receptor oligomerization and phosphorylation of Igα and β immunoreceptor tyrosine-based activated motifs by SRC family kinases. ITAM phosphorylation results in the recruitment and activation of Syk that initiates downstream events and amplifies the original BCR signal. Given the role of tonic BCR signaling in normal B-cell and Syk-dependent survival of non-Hodgkins lymphoma cell lines in vitro (Chen, L., et. al, *Blood,* 2006: 108:3428-3433), Syk inhibition is a promising rational treatment target for certain B-cell lymphomas and chronic lymphocytic leukemia (CLL) (Stefania Gobessi, Luca Laurenti, Pablo Longo, Laura Carsetti, Giuseppe Leone, Dimitar G. Efremov, Constitutive activation of the protein tyrosine kinase Syk in Chronic Lymphocytic Leukemia B-cells, Blood, 2007, 110, Abstract 1123)

The oncogenic potential of the spleen tyrosine kinase (Syk) has been described in a number of different settings. Clinically, Syk over-expression is reported in mantle cell lymphoma (Rinaldi, A, et. al, *Br. J. Haematol.*, 2006; 132:303-316) and the TEL-Syk fusion protein (Translocated ETS Leukemia) generated by a chromosomal translocation (t(9;12)(q22;p12)) leads to increased Syk activity and is associated with myelodysplastic syndrome (Kuno, Y., et. al, *Blood,* 2001; 97:1050-1055). Leukemia is induced in mice by adoptively transferring bone marrow cells that express human TEL-Syk (Wossning, T., JEM, 2006; 203:2829-2840). Further, in mouse primary bone marrow cells, over-expression of Syk results in IL-7 independent growth in culture (Wossning, T., et. al, JEM, 2006; 203:2829-2840).

Interestingly, Syk signaling appears to be required for B-cell development and survival in humans and mouse. Inducible loss of the B-cell receptor (Lam, K., et. al, Cell, 1997; 90:1073-1083) or Igα (Kraus, M., et. al, Cell, 2004; 117:787-800) results in loss of peripheral B-cells in mice. Over-expression of the protein tyrosine phosphatase PTP-RO, which is known to negatively regulate Syk activity, inhibits proliferation and induces apoptosis in cell lines derived from non-Hodgkin's lymphomas (Chen, L., et. al, Blood, 2006; 108:3428-3433). Finally, B-cell lymphomas rarely exhibit loss of BCR expression, and anti-idiotype therapy rarely leads to resistance (Kuppers, R. Nat Rev Cancer, 2005; 5:251-262).

Engagement of the antigen-specific B-cell receptor (BCR) activates multiple signaling pathways that ultimately regulate the cells activation status, promoting survival and clonal expansion. Signaling through the BCR is made possible by its association with two other members of the immunoglobulin super-family; Igα and Igβ, each bearing an immunotyrosine based activation motif (ITAM) (Jumaa, Hendriks et al. Annu Rev Immunol 23: 415-45 (2005). The ITAM domain is directly phosphorylated by Src family kinases in response to BCR engagement. The spleen tyrosine kinase (Syk) docks with and phosphorylates the ITAM, a process that enhances its kinase activity, resulting in Syk autophosphorylation and tyrosine phosphorylation of multiple downstream substrates (Rolli, Gallwitz et al. Mol Cell 10(5): 1057-69 (2002). This signaling pathway is active in B-cells beginning at the transition from pro- to pre-B-cell stage of development, when the newly formed pre-BCR is expressed. In fact, B-cell development arrests at the pro-B-cell stage in Syk knockout mice (Cheng, Rowley et al. 1995; Turner, Mee et al. Nature 378(6554): 303-6 (1995). Inducible loss of the B-cell receptor (Lam. Kuhn et al. Cell 90(6): 1073-83 (1997) or Igα (Kraus, Alimzhanov et al. Cell 117(6): 787-800 (2004) results in loss of peripheral B-cells in mice. Human B-cells also appear to require Syk for proliferation and survival. Over-expression of the protein tyrosine phosphatase PTP-RO, a negative regulator of Syk activity, inhibits proliferation and induces apoptosis in cell lines derived from non-Hodgkin's lymphomas (NHL) (Chen, Juszczynski et al. Blood 108(10): 3428-33 (2006). Knock down of Syk by siRNA in the NHL line SUDHL-4 led to a block in the G1/S transition of the cell cycle (Gururajan, Dasu et al. J Immunol 178(1): 111-21 (2007). Together, these data suggest that Syk signaling is required for the development, proliferation, and even survival of human and mouse B-cells.

Conversely, the oncogenic potential of Syk has been described in a number of different settings. Clinically, Syk over-expression is reported in mantle cell lymphoma (Rinaldi, Kwee et al. Br J Haematol 132(3): 303-16 (2006) and the TEL-Syk fusion protein (translocated ETS leukemia) generated by a chromosomal translocation (t(9;12)(q22;p12)) leads to increased Syk activity and is associated with myelodysplastic syndrome (Kuno, Abe et al. Blood 97(4): 1050-5 (2001). Leukemia is induced in mice by the adoptive transfer of bone marrow cells that express human TEL-Syk (Wossning. Herzog et al. J Exp Med 203(13): 2829-40 (2006). Further, in mouse primary bone marrow cells, over-expression of Syk results in IL-7 independent growth in culture (Wossning, Herzog et al. 2006). Consistently, Syk was reported to mediate mTOR (mammalian target of rapamycin) survival signals in follicular, mantle cell. Burkitt's, and diffuse large B-cell NHL (Leseux, Hamdi et al. Blood 108(13): 4156-62 (2006). Additional recent studies also suggest that Syk-dependant survival signals may play a role in B-cell malignancies, including diffuse large B-cell lymphoma (DLBCL), mantle cell lymphoma and follicular lymphoma (Gururajan, Jennings et al. 2006; Irish, Czerwinski et al. J Immunol 176(10): 5715-9 (2006). Given the role of tonic BCR signaling in normal B-cells and Syk-dependent survival of NHL cell lines in vitro, the specific inhibition of Syk may prove promising for the treatment of certain B-cell lymphomas.

Recently, R406 (Rigel Pharmaceuticals) was reported to inhibit ITAM signaling in response to various stimuli, including FcεR1 and BCR induced Syk activation (Braselmann, Taylor et al. J Pharmacol Exp Ther 319(3): 998-1008 (2006). Interestingly, this ATP-competitive inhibitor of Syk was also active against Flt3, cKit, and JAK kinases, but not against Src kinsase (Braselmann, Taylor et al. 2006). Activating mutations to Flt3 are associated with AML and inhibition of this kinase is currently under clinical development (Burnett and Knapper Hematology Am Soc Hematol Educ Program 2007: 429-34 (2007). Over-activation of the tyrosine kinase cKit is also associated with hematologic malignancies, and a target for cancer therapy (Heinrich, Griffith et al. Blood 96(3): 925-32 (2000). Similarly, JAK3 signaling is implicated in leukemias and lymphomas, and is currently exploited as a potential therapeutic target (Heinrich, Griffith et al. 2000). Importantly, the multi-kinase inhibitory activity of R406 attenuates BCR signaling in lymphoma cell lines and primary human lymphoma samples, resulting in apoptosis of the former (Chen, Monti et al. Blood 111(4): 2230-7 (2008). Further, a phase II clinical trial reported favorable results by this compound in refractory NHL and chronic lymphocytic leukemia. Although the precise mechanism of action is unclear for R406, the data suggest that inhibition of kinases that mediate survival signaling in lymphocytes is clinically beneficial.

Additional recent studies also suggest that Syk-dependant survival signals may play a role in B-cell malignancies, including DLBCL, mantle cell lymphoma and follicular lymphoma (see e.g., S. Linfengshen et al. Blood. February 2008; 111: 2230-2237; J. M. Irish et al. Blood, 2006: 108: 3135-3142; A. Renaldi et al. Brit J. Haematology, 2006; 132: 303-316; M. Guruoajan et al. J. Immunol, 2006; 176: 5715-5719; L. Laseux et al. Blood, 2006; 108: 4156-4162.

JAK kinases (Janus Kinases) are a family of cytoplasmic protein tyrosine kinases including JAK1, JAK2, JAK3 and TYK2. The JAKs play a crucial role in cytokine signaling. Each of the JAK kinases is selective for the receptors of certain cytokines, though multiple JAK kinases can be affected by particular cytokine or signaling pathways. Studies suggest that JAK3 associates with the common cytokine receptor gamma chain (Fcγ or γc) of the various cytokine receptors. JAK3 in particular selectively binds to receptors and is part of the cytokine signaling pathway for and activated by IL-2, IL-4, IL-7, IL-9, IL-15 and IL-21. JAK1 interacts with, among others, the receptors for cytokines IL-2, IL-4, IL-7, IL-9 and IL-21, while JAK2 interacts with, among others, the receptors for IL-9 and TNF-α. Upon the binding of certain cytokines to their receptors (e.g., IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

The downstream substrates of JAK family kinases include the signal transducer activator of transcription (STAT) proteins. Phosphorylated JAK kinases bind various STAT (Signal Transducer and Activator of Transcription) proteins. STAT proteins, which are DNA binding proteins activated by phosphorylation of tyrosine residues, function both as signaling molecules and transcription factors and ultimately bind to specific DNA sequences present in the promoters of cytokine-responsive genes (Leonard et al., (2000), J. Allergy Clin. Immunol. 105:877-888).

JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas. For a review of the pharmaceutical intervention of the JAK/STAT pathway, see Frank, (1999), Mol. Med. 5:432:456 and Seidel et al., (2000), Oncogene 19:2645-2656.

JAK3 in particular has been implicated in a variety of biological processes. For example, the proliferation and survival of murine mast cells induced by IL-4 and IL-9 have been shown to be dependent on JAK3- and gamma chain-signaling (Suzuki et al., (2000), *Blood* 96:2172-2180). JAK3 also plays a crucial role in IgE receptor-mediated mast cell degranulation responses (Malaviya et al., (1999). Biochem. Biophys. Res. Commun. 257:807-813), and inhibition of JAK3 kinase has been shown to prevent type I hypersensitivity reactions, including anaphylaxis (Malaviya et al., (1999), J. Biol. Chem. 274:27028-27038). JAK3 inhibition has also been shown to result in immune suppression for allograft rejection (Kirken, (2001), Transpl. Proc. 33:3268-3270). JAK3 kinases have also been implicated in the mechanism involved in early and late stages of rheumatoid arthritis (Muller-Ladner et al., (2000), J. Immunal. 164:3894-3901); familial amyotrophic lateral sclerosis (Trieu et al., (2000), Biochem Biophys. Res. Commun. 267:22-25); leukemia (Sudbeck et al., (1999), Clin. Cancer Res., 5:1569-1582); mycosis fungoides, a form of T-cell lymphoma (Nielsen et al., (1997), Prac. Natl. Acad. Sci. USA 94:6764-6769); and abnormal cell growth (Yu et al., (1997), J. Immunol. 159:5206-5210; Catlett-Falcone et al., (1999), Immunity 10:105-115).

JAK1, JAK2, and TYK2 are expressed ubiquitously, whereas JAK3 is expressed predominantly in hematopoietic cells. The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., (1996), Mol. Cell. Biol. 16:4710-6; Jurlander et al., (1997), Blood. 89:4146-52; Kaneko et al., (1997), Clin. Exp. Immun. 109:185-193; and Nakamura et al., (1996), J. Biol. Chem. 271: 19483-8). They are also known to be important for lymphocyte differentiation, function and survival. JAK-3 in particular plays an essential role in the function of lymphocytes, macrophages, and mast cells. Given the importance of this JAK kinase, compounds that modulate the JAK pathway, including those selective for JAK3, can be useful for treating diseases or conditions where the function of lymphocytes, macrophages, or mast cells is involved (Kudlacz et al., (2004) Am. J. Transplant 4:51-57; Changelian (2003) Science 302:875-878). Conditions in which targeting of the JAK pathway or modulation of the JAK kinases, particularly JAK3, are contemplated to be therapeutically useful include, leukemia, lymphoma, transplant rejection (e.g., pancreas islet transplant rejection, bone marrow transplant applications (e.g., graft-versus-host disease), autoimmune diseases (e.g., diabetes), and inflammation (e.g., asthma, allergic reactions). Conditions that can benefit from JAK3 inhibition are discussed in greater detail below.

In view of the numerous conditions that are contemplated to benefit by treatment involving modulation of the JAK pathway it is immediately apparent that new compounds that modulate JAK pathways and methods of using these compounds should provide substantial therapeutic benefits to a wide variety of patients. Provided herein are novel 2,4-pyrimidinediamine compounds for use in the treatment of conditions in which targeting of the JAK pathway or inhibition of JAK kinases, particularly JAK3, are therapeutically useful.

Patents and patent applications describing substituted pyrimidinediamine compounds include: U.S. application Ser. No. 10/355,543, filed Jan. 31, 2003 (US 2004/0029902 A1); international application Serial No. PCT/US03/03022, filed Jan. 31, 2003 (WO 03/063794), U.S. application Ser. No. 10/631,029, filed Jul. 29, 2003; international application Serial No. PCT/US03/24087 (WO 04/014382); U.S. application Ser. No. 10/903,263, filed Jul. 30, 2004; and international application Serial No. PCT/US2004/24716 (WO 05/016893), the disclosures of which are incorporated herein by reference. Substituted pyrimidinediamine compounds are also described in international patent application publication numbers: WO 02/059110, WO 03/074515, WO 03/106416, WO 03/066601, WO 03/063794, WO 04/046118, WO 05/016894, WO 05/122294, WO 05/066156, WO 03/002542, WO 03/030909, WO 00/39101, WO 05/037800, and U.S. Pat. Publ. No. 2003/0149064.

While progress has been made in this field, there remains a need in the art for compounds that inhibit Syk and/or JAK kinase, as well as for methods for treating conditions in a patient, such as restenosis, thrombosis, and/or inflammation that can benefit from such inhibition. Moreover, the availability of compounds that selectively inhibit one or both of these kinases as compared to other kinases would also be desirable. The present invention satisfies this and other needs.

BRIEF SUMMARY OF THE INVENTION

In one aspect, provided are compounds of Formula (I):

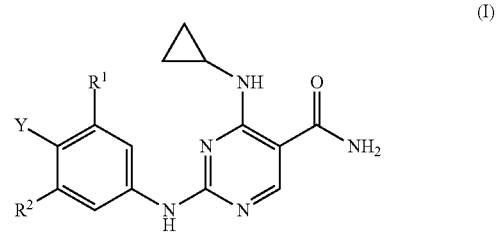

(I)

or a tautomer or a pharmaceutically acceptable salt thereof, wherein $R^1$ and $R^2$ are as described herein.

In another aspect, provided are pharmaceutical compositions comprising a therapeutically effective amount of one or more of such compounds, as well as methods for the use of the compounds in therapeutic applications. The compounds disclosed herein have utility over a wide range of therapeutic applications, and may be used to treat a variety of conditions such as those mediated at least in part by JAK and/or Syk kinase. For example, such conditions include, but are not limited to, those associated with cardiovascular disease, inflammatory disease, autoimmune disease, or a cell proliferative disorder.

These and other aspects and features of the invention will be apparent upon reference to the following detailed description.

DETAILED DESCRIPTION OF THE INVENTION

It is noted here that as used in this specification and the appended claims, the singular forms "a," "an," and "the" include plural reference unless the context clearly dictates otherwise.

"Alkoxy" refers to —O(alkyl) where alkyl is as defined herein. Representative examples of alkoxy groups include methoxy, ethoxy, t-butoxy, and the like.

"Alkyl," by itself or as part of another substituent, means, unless otherwise stated, a straight- or branched-chain, fully saturated aliphatic hydrocarbon radical having the number of carbon atoms designated. For example, "$C_{1-8}$alkyl" refers to a hydrocarbon radical, either straight- or branched-chain, that contains from 1 to 8 carbon atoms and that is derived by the removal of one hydrogen atom from a single carbon atom of a parent alkane. Alkyl includes branched-chain isomers of straight-chain alkyl groups, such as isopropyl, t-butyl, isobutyl, sec-butyl, and the like. Representative alkyl groups include straight- and branched-chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms.

"Alkylene" refers to a divalent alkyl group that is derived by the removal of two hydrogen atoms from a parent alkane. For example, alkylene includes methylene (—$CH_2$—), ethylmethylene ($CH_3CH_2CH$), ethylene (—$CH_2CH_2$—), 1,3-propylene, 1,2-propylene, and the like.

"Amino" refers to a monovalent radical —$NH_2$.

"Aryl" by itself or as part of another substituent refers to a polyunsaturated, aromatic, hydrocarbon group containing from 6 to 14 carbon atoms, which can be a single ring or multiple rings (up to three rings) that are fused together or linked covalently. Aryl groups include aromatic ring(s) fused to non-aromatic cycloalkyl groups and where the point of attachment to the remainder of the molecule can be through any suitable ring atom of any ring. Thus the phrase includes, but is not limited to, groups such as phenyl, anthracenyl, naphthyl by way of example. Non-limiting examples of aryl groups include phenyl, 1-naphthyl, 2-naphthyl and 4-biphenyl.

"Cycloalkyl" refers to a saturated or partially saturated cyclic group of from 3 to 14 carbon atoms and no ring heteroatoms and having a single ring or multiple rings including fused, bridged, and spiro ring systems. Examples of cycloalkyl groups include, for instance, adamantyl, cyclopropyl, cyclobutyl, cyclopentyl, cyclooctyl, and cyclohexenyl. "$C_{u'-v'}$cycloalkyl" refers to cycloalkyl groups having u' to v' carbon atoms as ring members.

"Halo" or "halogen" by themselves or as part of another substituent, mean, unless otherwise stated, a fluorine, chlorine, bromine, or iodine atom. Additionally, terms such as "haloalkyl", are meant to include an alkyl in which one or more hydrogen is replaced by halogen atoms that can be the same or different, in a number ranging from one up to the maximum number of halogens permitted e.g. for alkyl, (2m'+1), where m' is the total number of carbon atoms in the alkyl group. For example, the term "halo$C_{1-8}$ alkyl" is meant to include difluoromethyl, trifluoromethyl, 2,2,2-trifluoroethyl, 4-chlorobutyl, 3-bromopropyl, and the like. Additionally, term "haloalkoxy" refers to an alkoxy radical substituted with one or more halogen atoms. In one group of embodiments, the haloalkyl and haloalkoxy groups have from one to five or from one to three halogen atoms. Examples of haloalkoxy groups include difluoromethoxy and trifluoromethoxy.

"Heteroaryl" refers to a cyclic or polycyclic radical having at least one aromatic ring and from one to five ring heteroatom selected from N, O, and S, and optionally one or more oxo (=O) substituents attached to one or more carbon ring atoms, and wherein the nitrogen and sulfur ring atoms are optionally oxidized. A heteroaryl group can be attached to the remainder of the molecule through a heteroatom or through a carbon atom and can contain 5 to 10 carbon atoms. Heteroaryl groups include polycyclic aromatic ring(s) fused to non-aromatic cycloalkyl or heterocyclyl groups, and where the point of attachment to the remainder of the molecule can be through any suitable ring atom of any ring. In a polycyclic heteroaryl group, the ring heteroatom(s) can be in either an aromatic or non-aromatic ring or both. The term "aromatic ring" include any ring having at least one planar resonance structure where 2n+2 pi electrons are delocalized about the ring. Non-limiting examples of heteroaryl groups include xanthine, hypoxanthine, 5-benzothiazolyl, purinyl, 2-benzimidazolyl, benzopyrazolyl, 5-indolyl, azaindole, 1-isoquinolyl, 5-isoquinolyl, 2-quinoxalinyl, 5-quinoxalinyl, 3-quinolyl, 6-quinolyl 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl and 4-pyrimidyl. "Bicyclic heteroaryl" refers to a heteroaryl radical that contains two fused rings.

The terms "optional" or "optionally" as used throughout the specification means that the subsequently described event or circumstance may but need not occur, and that the description includes instances where the event or circumstance occurs and instances in which it does not. For example, "alkyl group optionally substituted with an halo group" means that the halogen may but need not be present, and the description includes situations where the alkyl group is substituted with a halo group and situations where the alkyl group is not substituted with a halo group.

In each of the above embodiments designating a number of atoms e.g. "$C_{1-8}$" is meant to include all possible embodiments that have one fewer atom. Non-limiting examples include $C_{1-4}$, $C_{1-5}$, $C_{1-6}$, $C_{1-7}$, $C_{2-8}$, $C_{2-7}$, $C_{3-8}$, $C_{3-7}$ and the like.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M. et al., "Pharmaceutical Salts," *Journal of Pharmaceutical Science*, 66:1-19, 1977). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

The terms "pharmaceutically effective amount", "therapeutically effective amount" or "therapeutically effective dose" refer to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disorder or condition and its severity and the age, weight, etc., of the mammal to be treated.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, Protective Groups in Organic Chemistry, 3$^{rd}$ Ed., 1999, John Wiley & Sons, NY and Harrison et al., Compendium of Synthetic Organic Methods, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl and trityl ethers, as well as alkyl ethers, tetrahydropyranyl ethers, trialkylsilyl ethers (e.g., TMS or TIPPS groups) and allyl ethers.

"Tautomer" refers to alternate forms of a molecule that differ in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring atom arrangements are possible.

The terms "treat", "treating", "treatment" and grammatical variations thereof as used herein, includes partially or completely delaying, alleviating, mitigating or reducing the intensity, progression, or worsening of one or more attendant symptoms of a disorder or condition and/or alleviating, mitigating or impeding one or more causes of a disorder or condition. Treatments according to the invention may be applied preventively, prophylactically, palliatively or remedially.

The term "wavy line" signifies the point of attachment of the substituent to the remainder of the molecule. When the wavy line is not depicted as being specifically appended to a specific ring atom, the point of attachment can be to any suitable atom of the substituent. For example, the wavy line in the following structure:

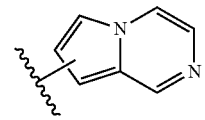

is intended to include, as the point of attachment, any of the six substitutable carbon atoms.

Compounds that have the same molecular formula but differ in the nature or sequence of bonding of their atoms or the arrangement of their atoms in space are termed "isomers". Isomers that differ in the arrangement of their atoms in space are termed "stereoisomers". "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 4th edition J. March, John Wiley and Sons, New York, 1992) differ in the chirality of one or more stereocenters.

The compounds of the present invention may also contain unnatural proportions of atomic isotopes at one or more of the atoms that constitute such compounds. For example, the compounds may be radiolabeled with isotopes, such as for example deuterium ($^2H$), tritium ($^3H$), iodine-125 ($^{125}I$) or carbon-14 ($^{14}C$). All isotopic variations of the compounds of the present invention, whether radioactive or not, are intended to be encompassed within the scope of the present invention.

Unless indicated otherwise, the nomenclature of substituents that are not explicitly defined herein are arrived at by naming the terminal portion of the functionality followed by the adjacent functionality toward the point of attachment. For example, the substituent "alkoxyalkyl" refers to an alkyl group that is substituted with alkoxy, "hydroxyalkyl" refers to an alkyl group that is substituted with hydroxyl, and (phenyl)$C_{1-8}$alkyl refers to a $C_{1-8}$alkyl group that is substituted with phenyl. For these substituents, the point of attachment is at the alkyl group.

It is understood that the definitions and formulas provided herein are not intended to include chemically impermissible substitution patterns (e.g., methyl substituted with five fluoro groups). Such impermissible substitution patterns are well known to the skilled artisan.

An "antagonist" or "inhibitor" refers to an agent or molecule that inhibits or binds to, partially or totally blocks stimulation or activity, decreases, closes, prevents, delays activation or enzymatic activity, inactivates, desensitizes, or down regulates the activity of a receptor of the invention. As used herein, "antagonist" also includes a reverse or inverse agonist.

As used herein, the term "condition or disorder responsive to modulation of JAK" and related terms and phrases refer to a condition or disorder associated with inappropriate, e.g., less than or greater than normal, activity of JAK and at least partially responsive to or affected by modulation of JAK (e.g., JAK antagonist or agonist results in some improvement in patient well-being in at least some patients). Inappropriate functional activity of JAK might arise as the result of expression of JAK in cells that normally do not express the receptor, greater than normal production of JAK, or slower than normal metabolic inactivation or elimination of JAK or its active metabolites, increased expression of JAK or degree of intracellular activation (leading to, e.g., inflammatory and immune-related disorders and conditions) or decreased expression of JAK. A condition or disorder associated with JAK may include a "JAK-mediated condition or disorder".

As used herein, the phrases "a condition or disorder mediated at least in part by JAK kinase activity", and related phrases and terms refer to a condition or disorder characterized by inappropriate, e.g., greater than normal, JAK activity. Inappropriate JAK functional activity might arise as the result of JAK expression in cells that normally do not express JAK or increased JAK expression or degree of intracellular activation (leading to, e.g., inflammatory and immune-related disorders and conditions). A condition or disorder mediated at least in part by Syk or JAK kinase activity may be completely or partially mediated by inappropriate JAK functional activity. However, a condition or disorder mediated at least in part by JAK kinase activity is one in which modulation of JAK results in some effect on the underlying condition or disorder (e.g., an JAK antagonist results in some improvement in patient well-being in at least some patients).

As used herein, the term "condition or disorder responsive to modulation of Syk" and related terms and phrases refer to a condition or disorder associated with inappropriate, e.g., less than or greater than normal, activity of Syk and at least partially responsive to or affected by modulation of Syk (e.g., Syk antagonist or agonist results in some improvement in patient well-being in at least some patients). Inappropriate functional activity of Syk might arise as the result of expression of Syk in cells that normally do not express the receptor, greater than normal production of Syk, or slower than normal metabolic inactivation or elimination of Syk or its active metabolites, increased expression of Syk or degree of intracellular activation (leading to, e.g., inflammatory and immune-related disorders and conditions) or decreased expression of Syk. A condition or disorder associated with Syk may include a "Syk-mediated condition or disorder".

As used herein, the phrases "a condition or disorder mediated at least in part by Syk kinase activity", and related phrases and terms refer to a condition or disorder characterized by inappropriate, e.g., greater than normal, Syk activity. Inappropriate Syk functional activity might arise as the result of Syk expression in cells that normally do not express Syk or increased Syk expression or degree of intracellular activation (leading to, e.g., inflammatory and immune-related disorders and conditions). A condition or disorder mediated at least in part by Syk or JAK kinase activity may be completely or partially mediated by inappropriate Syk functional activity. However, a condition or disorder mediated at least in part by Syk kinase activity is one in which modulation of Syk results in some effect on the underlying condition or disorder (e.g., an Syk antagonist results in some improvement in patient well-being in at least some patients).

As used herein, the phrases "Syk or JAK kinase," "JAK and/or Syk kinase." and related phrases and terms refer to Syk kinase, to JAK kinase, or to both Syk and JAK kinase. For example, a method for inhibiting Syk or JAK kinase would comprise groups of embodiments for inhibiting a Syk kinase, a JAK kinase, or both a Syk and a JAK kinase.

The term "intervention" refers to an action that produces an effect or that is intended to alter the course of a disease process. For example, "vascular intervention" refers to the use of an intravascular procedure such as angioplasty or a stent to open an obstructed blood vessel.

The term "intravascular device" refers to a device useful for a vascular recanalization procedure to restore blood flow through an obstructed blood vessel. Examples of intravascular devices include, without limitation, stents, balloon catheters, autologous venous/arterial grafts, prosthetic venous/arterial grafts, vascular catheters, and vascular shunts.

The terms "modulate", "modulation" and the like refer to the ability of a compound to increase or decrease the function and/or expression of Syk, JAK, or both, where such function may include transcription regulatory activity and/or protein-binding. Modulation may occur in vitro or in vivo. Modulation, as described herein, includes the inhibition, antagonism, partial antagonism, activation, agonism or partial agonism of a function or characteristic associated with Syk, JAK, or both, either directly or indirectly, and/or the upregulation or downregulation of the expression of Syk, JAK, or both, either directly or indirectly. In a preferred embodiment, the modulation is direct. Inhibitors or antagonists are compounds that, e.g., bind to, partially or totally block stimulation, decrease, prevent, inhibit, delay activation, inactivate, desensitize, or downregulate signal transduction. Activators or agonists are compounds that, e.g., bind to, stimulate, increase, open, activate, facilitate, enhance activation, activate, sensitize or upregulate signal transduction. The ability of a compound to inhibit the function of Syk, JAK, or both can be demonstrated in a biochemical assay, e.g., binding assay, or a cell-based assay. e.g., a transient transfection assay.

"Modulators" of activity are used to refer to "ligands", "antagonists" and "agonists" identified using in vitro and in vivo assays for activity and their homologs and mimetics. Modulators include naturally occurring and synthetic ligands, antagonists, agonists, molecules and the like. Assays to identify antagonists and agonists include, e.g., applying putative modulator compounds to cells, in the presence or absence of a receptor of the invention and then determining the functional effects on a receptor of the invention activity. Samples or assays comprising a receptor of the invention that are treated with a potential activator, inhibitor, or modulator are compared to control samples without the inhibitor, activator, or modulator to examine the extent of effect. Control samples (untreated with modulators) are assigned a relative activity value of 100%. Inhibition is achieved when the activity value of a receptor of the invention relative to the control is about 80%, optionally 50% or 25-1%. Activation is achieved when the activity value of a receptor of the invention relative to the control is 110%, optionally 150%, optionally 200-500%, or 1000-3000% higher.

"Subject" refers to human and non-human animals, especially mammals. Examples of subjects include, but are not limited to, humans, cows, dogs, cats, goats, sheep, pigs and rabbits.

In one group of embodiments, provided is a compound of Formula (I):

(I)

or a tautomer or a pharmaceutically acceptable salt thereof, wherein $R^1$ is selected from the group consisting of H, halo, $C_{1-4}$ alkoxy, and cyano;

$R^2$ is selected from the group consisting of H, halo, and $C_{1-4}$ alkyl;

Y is selected from the group consisting of ethyl, isopropyl, trifluoromethyl, fluoro, cyclopropyl, 1,2,3,6-tetrahydropyridin-4-yl, 4-(1-ethylsulfonyl)-1,2,3,6-tetrahydropyridin-4-yl, N-morpholino, piperidin-4-yl, 4-(vinylsulfonyl)piperazin-1-yl and T and W are independently N or C provided that at least one of T and W is N;

$R^3$ is selected from the group consisting of $C_{1-5}$ alkyl, haloC$_{1-4}$ alkyl, cyanoC$_{1-4}$ alkylene, $C_{3-6}$cycloalkyl, oxetan-3-yl, 1-cyclopropylpiperidin-4-yl, tetrahydropyran-4-yl, phenyl, pyridin-2-yl, 3-fluoropyridin-2-yl, pyridin-3-yl, HC(O), $R^{3a}$C(O), $R^{3b}$S(O)$_2$, and $R^{3c}$S(O)$_2$;

$R^{3a}$ is selected from the group consisting of ethyl, cyanoC$_{1-4}$ alkylene, $C_{1-4}$ alkoxy, $C_{1-4}$ alkoxyC$_{1-4}$ alkyl, N-morpholino, tetrahydropyran-4-yl, pyridin-3-yl, $C_{3-6}$ cycloalkyl, 1-cyanocyclopropyl, pyrrolidin-1-yl, and $(R^{3c})_2$N;

$R^{3b}$ is selected from the group consisting of cyclopropyl, pyridin-3-yl, 1-methyl-imidazol-4-yl, 1-methyl-pyrazol-4-yl, ethenyl, and $(R^{3c})_2$N;

$R^{3c}$ is independently $C_{1-4}$ alkyl;

the subscript n is 1 or 2;

the subscript m is 1 or 2;

the wavy line signifies the point of attachment to the remainder of the molecule;

the dashed line signifies that the bond between W and (CH$_p$) can be a single or double bond provided that when the dashed line is a double pond, the subscript p is 1 and when the dashed line signifies that the bond between W and (CH$_p$) is a single bond, the subscript p is 2;

provided that when T is N and W is C and $R^3$ is $R^{3c}$S(O)$_2$, then $R^{3c}$ is ethyl or isopropyl;

provided that when that when T and W are both N, then $R^3$ is $R^{3c}$S(O)$_2$ and $R^1$ and $R^2$ are not both H; and provided that when T is C and W is N and n and m are 2, $R^1$ and $R^2$ are not both H.

In one group of embodiments, n is 1. In another group of embodiments, n is 2. In one group of embodiments, m is 1. In another group of embodiments, n is 2.

In one group of embodiments, provided is a compound wherein Y has the formula:

In one group of embodiments, provided is a compound wherein Y has the formula:

In one group of embodiments, provided is a compound of Formula (Ia):

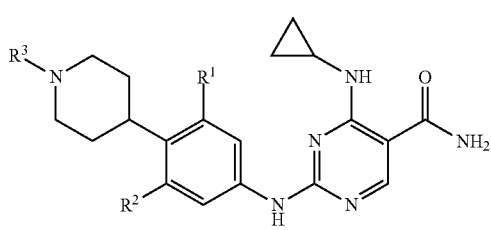

or a tautomer or a pharmaceutically acceptable salt thereof; wherein the other variables and provisos are as defined for the group of embodiments of Formula (I) above.

In one group of embodiments, provided is a compound of Formula (Ia), wherein $R^3$ is selected from the group consisting of $C_{1-5}$alkyl, halo$C_{1-4}$alkyl, cyano$C_{1-4}$alkylene, $C_{3-6}$cycloalkyl, oxetan-3-yl, 1-cyclopropylpiperidin-4-yl, tetrahydropyran-4-yl, phenyl, HC(O), $R^{3a}$C(O), $R^{3b}$S(O)$_2$, $R^{3c}$S(O)$_2$, pyridin-2-yl, 3-fluoropyridin-2-yl, and pyridin-3-yl; and wherein the other variables and provisos are as defined for the group of embodiments of Formula (Ia) above.

In one group of embodiments, provided is a compound of Formula (Ia), wherein $R^3$ is selected from the group consisting of methyl, ethyl, isopropyl, pentan-3-yl, 2,2,2,-trifluoroethyl, 2-fluoroethyl, 2,2,-difluoroethyl, 1,3,-difluoropropan-2-yl, cyclobutyl, cyclopenyl, and cyclohexyl; and wherein the other variables and provisos are as defined for any one of the groups of embodiments of Formula (Ia) above.

In one group of embodiments, provided is a compound of Formula (Ia), wherein $R^3$ is $R^{3b}$S(O)$_2$, wherein $R^{3b}$ is selected from the group consisting of cyclopropyl, pyridin-3-yl, 1-methyl-imidazol-4-yl, 1-methyl-pyrazol-4-yl, ethenyl, and dimethylamino; and wherein the other variables and provisos are as defined for any one of the groups of the embodiments of Formula (Ia) above.

In one group of embodiments, provided is a compound of Formula (Ia), wherein $R^{3b}$ is cyclopropyl; and wherein the other variables and provisos are as defined for any one of the groups of embodiments of Formula (Ia) above.

In one group of embodiments, provided is a compound of Formula (Ia), wherein $R^3$ is $R^{3c}$S(O)$_2$; wherein $R^{3c}$ is ethyl or isopropyl; and wherein the other variables and provisos are as defined for any one of the groups of the embodiments of Formula (Ia) above.

In one group of embodiments, provided is a compound of Formula (Ia), wherein $R^3$ is $R^{3a}$ C(O); and wherein the other variables and provisos are as defined for any one of the groups of embodiments of Formula (Ia) above.

In one group of embodiments, provided is a compound of Formula (Ia), wherein $R^{3a}$ is selected from the group consisting of ethyl, N-morpholino, tetrahydropyran-4-yl, pyridin-3-yl, ethoxymethyl, cyclopropyl, methoxy, ethoxy, pyrrolidin-1-yl, 1-cyanocyclopropyl, and dimethylamino; and wherein the other variables and provisos are as defined for any one of the groups of embodiments of Formula (Ia) above.

In one group of embodiments, provided is a compound of Formula (Ia), wherein $R^{3a}$ is ethyl; and wherein the other variables and provisos are as defined for any one of the groups of embodiments of Formula (Ia) above.

In one group of embodiments, provided is a compound of Formula (Ia), wherein $R^{3a}$ is cyano$C_{1-4}$alkylene; and wherein the other variables and provisos are as defined for any one of the groups of embodiments of Formula (Ia) above.

In one group of embodiments, provided is a compound of Formula (Ia), wherein $R^{3a}$ is cyanomethyl; and wherein the other variables and provisos are as defined for any one of the groups of embodiments of Formula (Ia) above.

In one group of embodiments, provided is a compound of Formula (Ia), wherein $R^1$ and $R^2$ are H; and wherein the other variables and provisos are as defined for any one of the groups of embodiments of Formula (Ia) above.

In one group of embodiments, provided is a compound of Formula (Ib):

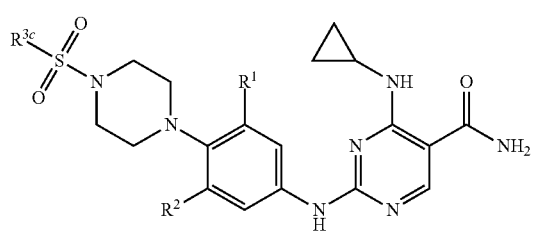

or a tautomer or a pharmaceutically acceptable salt thereof; wherein the other variables and provisos are as defined for the group of embodiments of Formula (I) above.

In one group of embodiments, provided is a compound of Formula (Ib), wherein $R^1$ is selected from the group consisting fluoro, chloro, and methoxy; and wherein the other variables and provisos are as defined for the group of embodiments of Formula (Ib) above.

In one group of embodiments, provided is a compound of Formula (Ib), wherein $R^2$ is selected from the group consisting fluoro and methyl; and wherein the other variables and provisos are as defined for any one of the groups of embodiments of Formula (Ib) above.

In one group of embodiments, provided is a compound of Formula (Ib), wherein $R^3$ is methyl; and wherein the other variables and provisos are as defined for any one of the groups of embodiments of Formula (Ib) above.

In one group of embodiments, provided is a compound of Formula (Ib), wherein $R^3$ is ethyl; and wherein the other variables and provisos are as defined for any one of the groups of embodiments of Formula (Ib) above.

In one group of embodiments, provided is a compound of Formula (Ic):

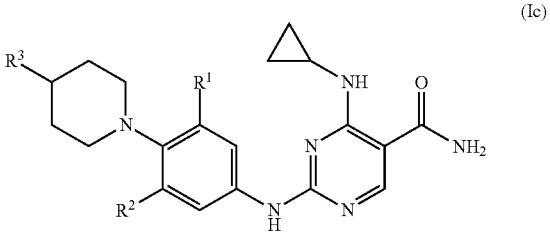

or a tautomer or a pharmaceutically acceptable salt thereof; wherein the other variables and provisos are as defined for the group of embodiments of Formula (I) above.

In one group of embodiments, provided is a compound of Formula (Ic), wherein $R^3$ is $R^{3a}$C(O); and wherein the other variables and provisos are as defined for the group of embodiments of Formula (Ic) above.

In one group of embodiments, provided is a compound of Formula (Ic), wherein $R^{3a}$ is dimethylamino; and wherein the other variables and provisos are as defined for any one of the groups of embodiments of Formula (Ic) above.

In one group of embodiments, provided is a compound of Formula (Ic), wherein $R^1$ is halo or alkoxy; and wherein the other variables and provisos are as defined for any one of the groups of embodiments of Formula (Ic) above.

In one group of embodiments, provided is a compound of Formula (Ic), wherein $R^2$ is H; and wherein the other variables and provisos are as defined for any one of the groups of embodiments of Formula (Ic) above.

In one group of embodiments, provided is a compound of Formula (Ia) that is selected from the group consisting of:

| Example No. | Structure | Compound Name |
|---|---|---|
| 1 | 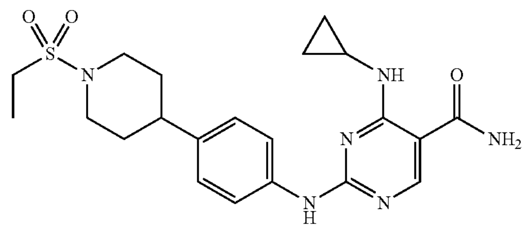 [SMILES: CCS(=O)(=O)N1CCC(c2ccc(Nc3ncc(C(N)=O)c(NC4CC4)n3)cc2)CC1] | 4-(cyclopropylamino)-2-((4-(1-(ethylsulfonyl)piperidin-4-yl)phenyl)amino)pyrimidine-5-carboxamide |
| 2 | 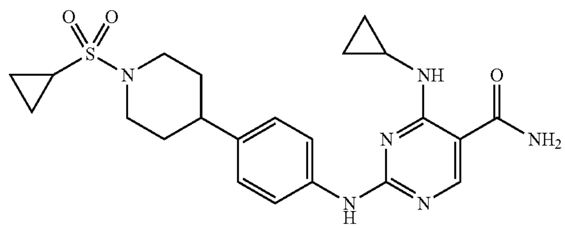 [SMILES: NC(=O)c1cnc(Nc2ccc(C3CCN(S(=O)(=O)C4CC4)CC3)cc2)nc1NC1CC1] | 4-(cyclopropylamino)-2-((4-(1-(cyclopropylsulfonyl)piperidin-4-yl)phenyl)amino)pyrimidine-5-carboxamide |
| 3 | 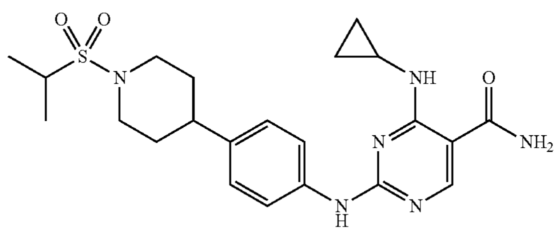 | 4-(cyclopropylamino)-2-((4-(1-(isopropylsulfonyl)piperidin-4-yl)phenyl)amino)pyrimidine-5-carboxamide |
| 4 | 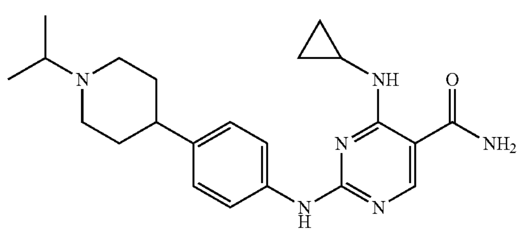 [SMILES: CC(C)N1CCC(c2ccc(Nc3ncc(C(N)=O)c(NC4CC4)n3)cc2)CC1] | 4-(cyclopropylamino)-2-((4-(1-isopropylpiperidin-4-yl)phenyl)amino)pyrimidine-5-carboxamide |
| 5 | 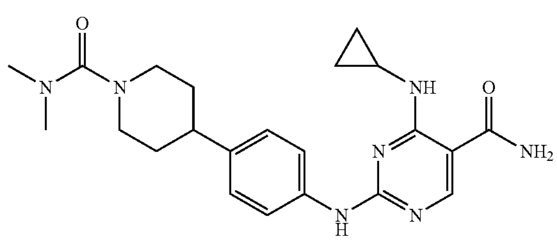 [SMILES: CN(C)C(=O)N1CCC(c2ccc(Nc3ncc(C(N)=O)c(NC4CC4)n3)cc2)CC1] | 4-(cyclopropylamino)-2-((4-(1-(dimethylcarbamoyl)piperidin-4-yl)phenyl)amino)pyrimidine-5-carboxamide |

-continued

| Example No. | Structure | Compound Name |
|---|---|---|
| 6 | 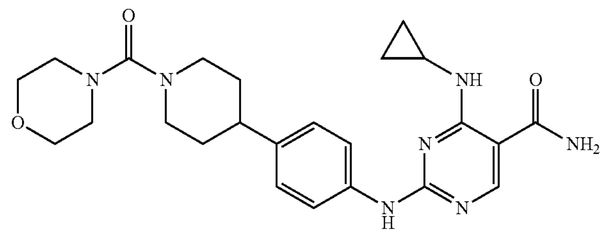 [SMILES: NC(=O)c1cnc(Nc2ccc(C3CCN(C(=O)N4CCOCC4)CC3)cc2)nc1NC1CC1] | 4-(cyclopropylamino)-2-((4-(1-(morpholine-4-carbonyl)piperidin-4-yl)phenyl)amino)pyrimidine-5-carboxamide |
| 7 | 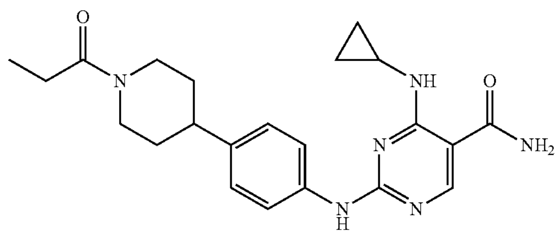 [SMILES: CCC(=O)N1CCC(c2ccc(Nc3ncc(C(N)=O)c(NC4CC4)n3)cc2)CC1] | 4-(cyclopropylamino)-2-((4-(1-propionylpiperidin-4-yl)phenyl)amino)pyrimidine-5-carboxamide |
| 8 | 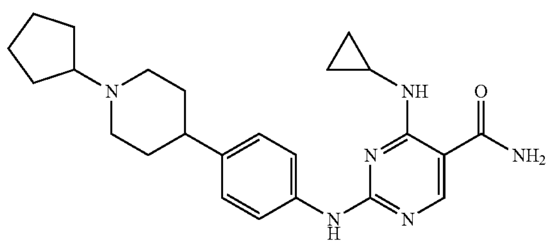 [SMILES: NC(=O)c1cnc(Nc2ccc(C3CCN(C4CCCC4)CC3)cc2)nc1NC1CC1] | 2-((4-(1-cyclopentylpiperidin-4-yl)phenyl)amino)-4-(cyclopropylamino)pyrimidine-5-carboxamide |
| 9 | 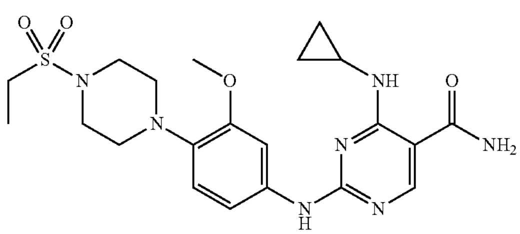 | 4-(cyclopropylamino)-2-((4-(4-(ethylsulfonyl)piperazin-1-yl)-3-methoxyphenyl)amino)pyrimidine-5-carboxamide |
| 10 | 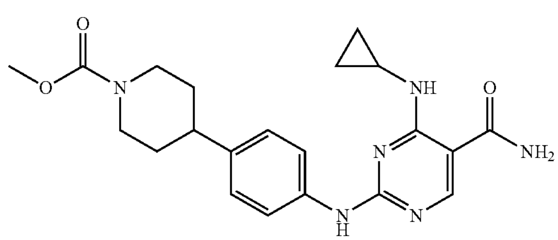 | methyl 4-(4-((5-carbamoyl-4-(cyclopropylamino)pyrimidin-2-yl)amino)phenyl)piperidine-1-carboxylate |
| 11 | 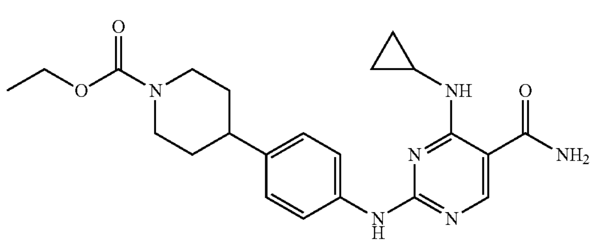 [SMILES: CCOC(=O)N1CCC(c2ccc(Nc3ncc(C(N)=O)c(NC4CC4)n3)cc2)CC1] | ethyl 4-(4-((5-carbamoyl-4-(cyclopropylamino)pyrimidin-2-yl)amino)phenyl)piperidine-1-carboxylate |

-continued

| Example No. | Structure | Compound Name |
|---|---|---|
| 12 | 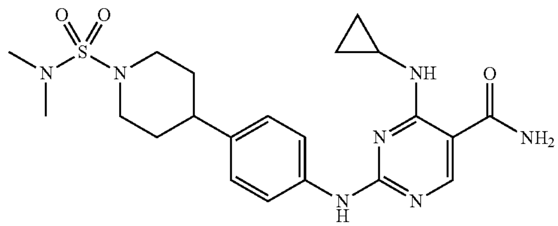 [SMILES: CN(C)S(=O)(=O)N1CCC(c2ccc(Nc3ncc(C(N)=O)c(NC4CC4)n3)cc2)CC1] | 4-(cyclopropylamino)-2-((4-(1-(N,N-dimethylsulfamoyl)piperidin-4-yl)phenyl)amino)pyrimidine-5-carboxamide |
| 13 | 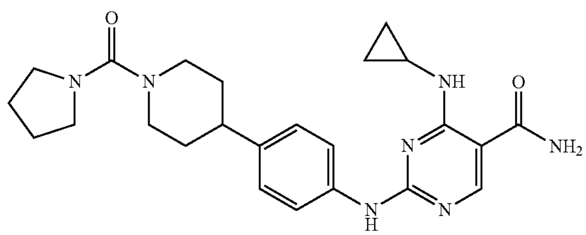 [SMILES: NC(=O)c1cnc(Nc2ccc(C3CCN(C(=O)N4CCCC4)CC3)cc2)nc1NC1CC1] | 4-(cyclopropylamino)-2-((4-(1-(pyrrolidine-1-carbonyl)piperidin-4-yl)phenyl)amino)pyrimidine-5-carboxamide |
| 14 | 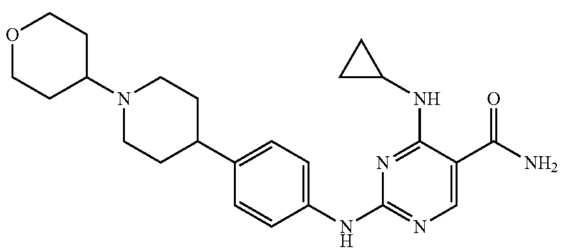 [SMILES: NC(=O)c1cnc(Nc2ccc(C3CCN(C4CCOCC4)CC3)cc2)nc1NC1CC1] | 4-(cyclopropylamino)-2-((4-(1-(tetrahydro-2H-pyran-4-yl)piperidin-4-yl)phenyl)amino)pyrimidine-5-carboxamide |
| 15 | 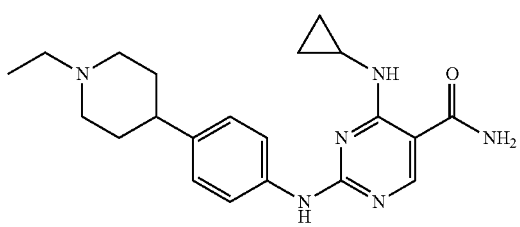 [SMILES: CCN1CCC(c2ccc(Nc3ncc(C(N)=O)c(NC4CC4)n3)cc2)CC1] | 4-(cyclopropylamino)-2-((4-(1-ethylpiperidin-4-yl)phenyl)amino)pyrimidine-5-carboxamide |
| 16 | 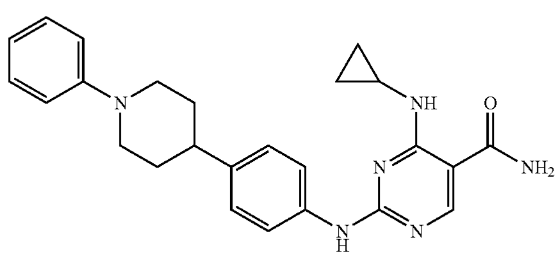 | 4-(cyclopropylamino)-2-((4-(1-phenylpiperidin-4-yl)phenyl)amino)pyrimidine-5-carboxamide |
| 17 | 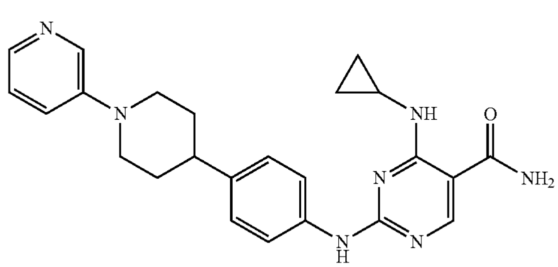 [SMILES: NC(=O)c1cnc(Nc2ccc(C3CCN(c4cccnc4)CC3)cc2)nc1NC1CC1] | 4-(cyclopropylamino)-2-((4-(1-(pyridin-3-yl)piperidin-4-yl)phenyl)amino)pyrimidine-5-carboxamide |

| Example No. | Structure | Compound Name |
|---|---|---|
| 18 | 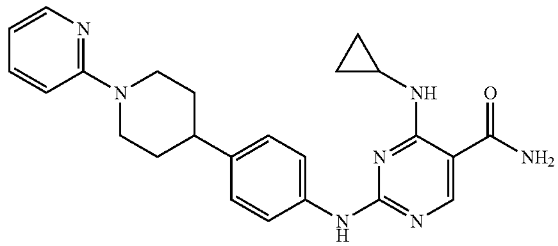 | 4-(cyclopropylamino)-2-((4-(1-(pyridin-2-yl)piperidin-4-yl)phenyl)amino)pyrimidine-5-carboxamide |
| 19 | 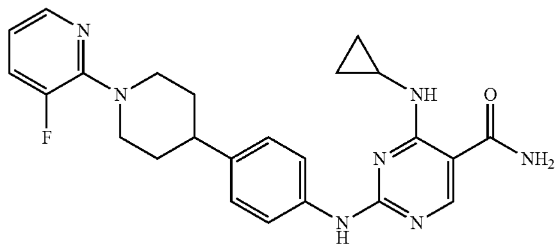 [SMILES: NC(=O)c1cnc(Nc2ccc(C3CCN(c4ncccc4F)CC3)cc2)nc1NC1CC1] | 4-(cyclopropylamino)-2-((4-(1-(3-fluoropyridin-2-yl)piperidin-4-yl)phenyl)amino)pyrimidine-5-carboxamide |
| 20 | 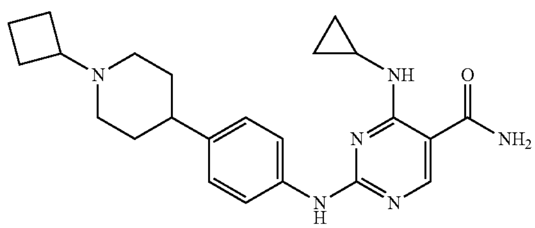 [SMILES: NC(=O)c1cnc(Nc2ccc(C3CCN(C4CCC4)CC3)cc2)nc1NC1CC1] | 2-((4-(1-cyclobutylpiperidin-4-yl)phenyl)amino)-4-(cyclopropylamino)pyrimidine-5-carboxamide |
| 21 | 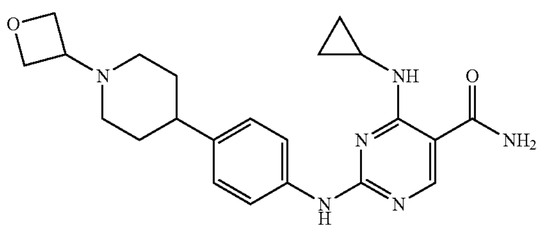 [SMILES: NC(=O)c1cnc(Nc2ccc(C3CCN(C4COC4)CC3)cc2)nc1NC1CC1] | 4-(cyclopropylamino)-2-((4-(1-(oxetan-3-yl)piperidin-4-yl)phenyl)amino)pyrimidine-5-carboxamide |
| 22 | 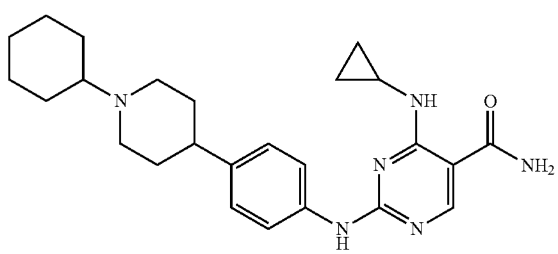 [SMILES: NC(=O)c1cnc(Nc2ccc(C3CCN(C4CCCCC4)CC3)cc2)nc1NC1CC1] | 2-((4-(1-cyclohexylpiperidin-4-yl)phenyl)amino)-4-(cyclopropylamino)pyrimidine-5-carboxamide |
| 23 | 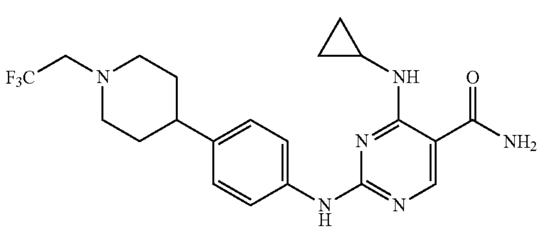 [SMILES: NC(=O)c1cnc(Nc2ccc(C3CCN(CC(F)(F)F)CC3)cc2)nc1NC1CC1] | 4-(cyclopropylamino)-2-((4-(1-(2,2,2-trifluoroethyl)piperidin-4-yl)phenyl)amino)pyrimidine-5-carboxamide |

| Example No. | Structure | Compound Name |
|---|---|---|
| 24 | 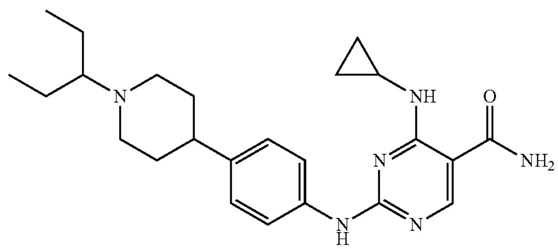 [SMILES: CCC(CC)N1CCC(c2ccc(Nc3ncc(C(N)=O)c(NC4CC4)n3)cc2)CC1] | 4-(cyclopropylamino)-2-((4-(1-(pentan-3-yl)piperidin-4-yl)phenyl)amino)pyrimidine-5-carboxamide |
| 25 | 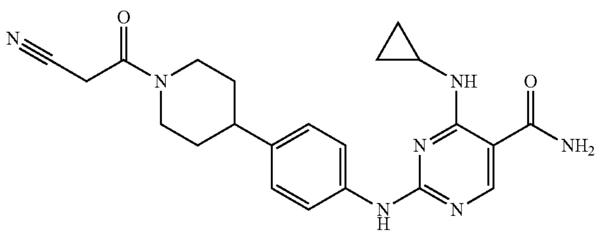 [SMILES: N#CCC(=O)N1CCC(c2ccc(Nc3ncc(C(N)=O)c(NC4CC4)n3)cc2)CC1] | 2-((4-(1-(2-cyanoacetyl)piperidin-4-yl)phenyl)amino)-4-(cyclopropylamino)pyrimidine-5-carboxamide |
| 26 | 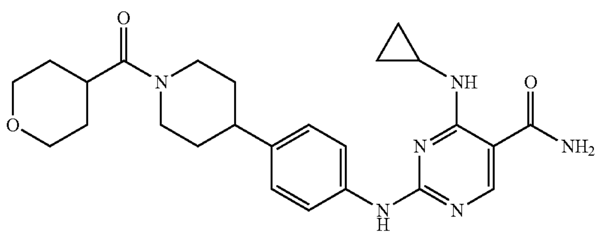 | 4-(cyclopropylamino)-2-((4-(1-(tetrahydro-2H-pyran-4-carbonyl)piperidin-4-yl)phenyl)amino)pyrimidine-5-carboxamide |
| 27 | 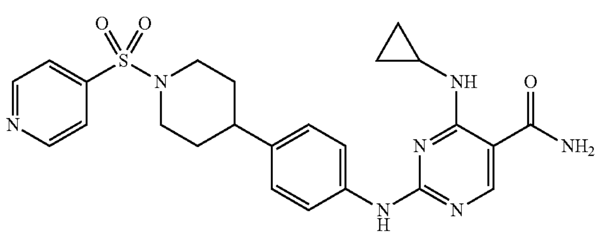 [SMILES: NC(=O)c1cnc(Nc2ccc(C3CCN(S(=O)(=O)c4ccncc4)CC3)cc2)nc1NC1CC1] | 4-(cyclopropylamino)-2-((4-(1-(pyridin-3-ylsulfonyl)piperidin-4-yl)phenyl)amino)pyrimidine-5-carboxamide |
| 28 | 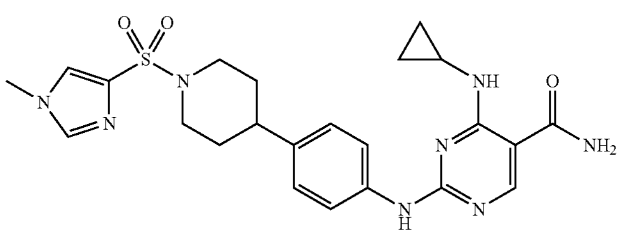 [SMILES: Cn1cnc(S(=O)(=O)N2CCC(c3ccc(Nc4ncc(C(N)=O)c(NC5CC5)n4)cc3)CC2)c1] | 4-(cyclopropylamino)-2-((4-(1-((1-methyl-1H-imidazol-4-yl)sulfonyl)piperidin-4-yl)phenyl)amino)pyrimidine-5-carboxamide |
| 29 | 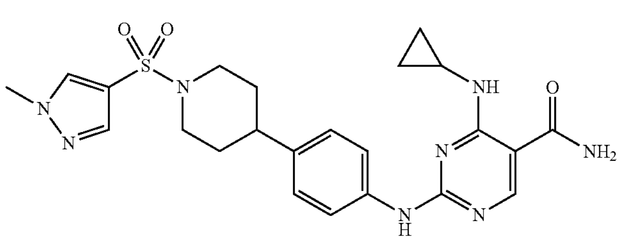 [SMILES: Cn1cc(S(=O)(=O)N2CCC(c3ccc(Nc4ncc(C(N)=O)c(NC5CC5)n4)cc3)CC2)cn1] | 4-(cyclopropylamino)-2-((4-(1-((1-methyl-1H-pyrazol-4-yl)sulfonyl)piperidin-4-yl)phenyl)amino)pyrimidine-5-carboxamide |

| Example No. | Structure | Compound Name |
|---|---|---|
| 30 | 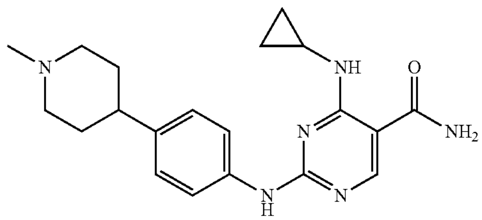 [SMILES: CN1CCC(c2ccc(Nc3ncc(C(N)=O)c(NC4CC4)n3)cc2)CC1] | 4-(cyclopropylamino)-2-((4-(1-methylpiperidin-4-yl)phenyl)amino)pyrimidine-5-carboxamide |
| 31 | 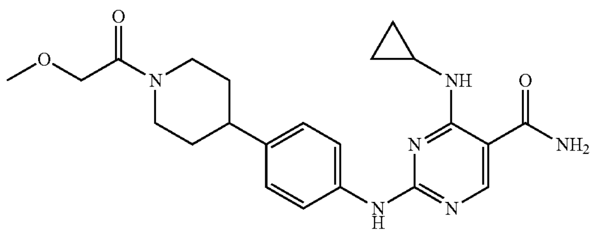 [SMILES: COCC(=O)N1CCC(c2ccc(Nc3ncc(C(N)=O)c(NC4CC4)n3)cc2)CC1] | 4-(cyclopropylamino)-2-((4-(1-(2-methoxyacetyl)piperidin-4-yl)phenyl)amino)pyrimidine-5-carboxamide |
| 32 | 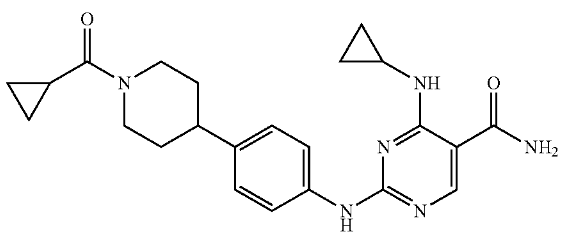 [SMILES: NC(=O)c1cnc(Nc2ccc(C3CCN(C(=O)C4CC4)CC3)cc2)nc1NC1CC1] | 2-((4-(1-(cyclopropanecarbonyl)piperidin-4-yl)phenyl)amino)-4-(cyclopropylamino)pyrimidine-5-carboxamide |
| 33 | 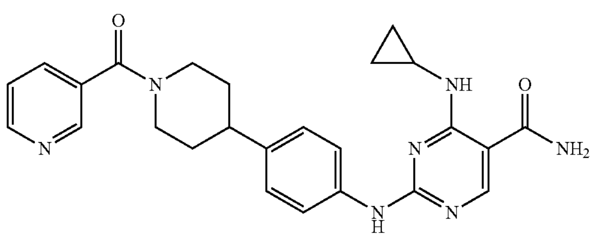 [SMILES: NC(=O)c1cnc(Nc2ccc(C3CCN(C(=O)c4cccnc4)CC3)cc2)nc1NC1CC1] | 4-(cyclopropylamino)-2-((4-(1-nicotinoylpiperidin-4-yl)phenyl)amino)pyrimidine-5-carboxamide |
| 34 | 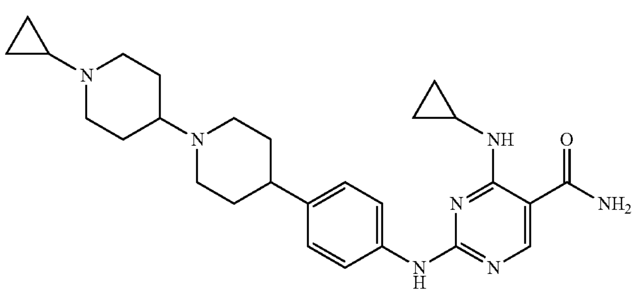 [SMILES: NC(=O)c1cnc(Nc2ccc(C3CCN(C4CCN(C5CC5)CC4)CC3)cc2)nc1NC1CC1] | 2-((4-(1'-cyclopropyl-[1,4'-bipiperidin]-4-yl)phenyl)amino)-4-(cyclopropylamino)pyrimidine-5-carboxamide |
| 35 | 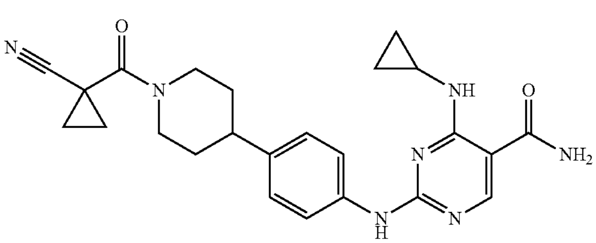 [SMILES: N#CC1(C(=O)N2CCC(c3ccc(Nc4ncc(C(N)=O)c(NC5CC5)n4)cc3)CC2)CC1] | 2-((4-(1-(1-cyanocyclopropanecarbonyl)piperidin-4-yl)phenyl)amino)-4-(cyclopropylamino)pyrimidine-5-carboxamide |

-continued

| Example No. | Structure | Compound Name |
|---|---|---|
| 36 | 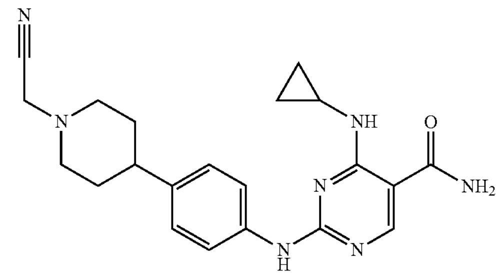 [SMILES: N#CCN1CCC(c2ccc(Nc3ncc(C(N)=O)c(NC4CC4)n3)cc2)CC1] | 2-((4-(1-(cyanomethyl)piperidin-4-yl)phenyl)amino)-4-(cyclopropylamino)pyrimidine-5-carboxamide |
| 37 | 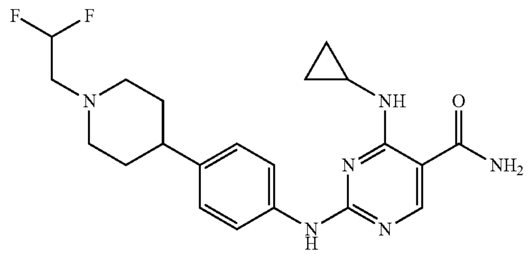 [SMILES: NC(=O)c1cnc(Nc2ccc(C3CCN(CC(F)F)CC3)cc2)nc1NC1CC1] | 4-(cyclopropylamino)-2-((4-(1-(2,2-difluoroethyl)piperidin-4-yl)phenyl)amino)pyrimidine-5-carboxamide |
| 38 | 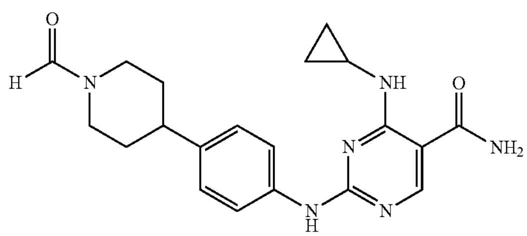 [SMILES: NC(=O)c1cnc(Nc2ccc(C3CCN(C=O)CC3)cc2)nc1NC1CC1] | 4-(cyclopropylamino)-2-((4-(1-formylpiperidin-4-yl)phenyl)amino)pyrimidine-5-carboxamide |
| 39 | 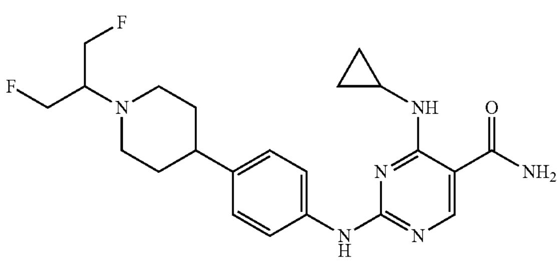 [SMILES: NC(=O)c1cnc(Nc2ccc(C3CCN(C(CF)CF)CC3)cc2)nc1NC1CC1] | 4-(cyclopropylamino)-2-((4-(1-(1,3-difluoropropan-2-yl)piperidin-4-yl)phenyl)amino)pyrimidine-5-carboxamide |
| 40 | | 4-(cyclopropylamino)-2-((4-(1-(2-fluoroethyl)piperidin-4-yl)phenyl)amino)pyrimidine-5-carboxamide | or a tautomer or a pharmaceutically acceptable salt thereof.

In one group of embodiments, provided is a compound of Formula (Ib) that is selected from the group consisting of:

| Example No. | Structure | Compound Name |
|---|---|---|
| 41 | 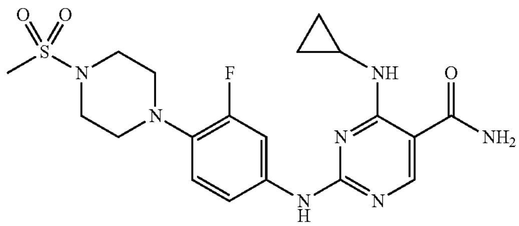 [SMILES: CS(=O)(=O)N1CCN(c2ccc(Nc3ncc(C(N)=O)c(NC4CC4)n3)cc2F)CC1] | 4-(cyclopropylamino)-2-((3-fluoro-4-(4-(methylsulfonyl)piperazin-1-yl)phenyl)amino)pyrimidine-5-carboxamide |
| 42 | 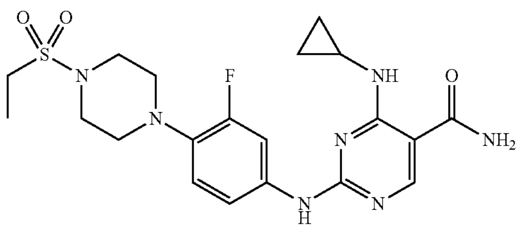 [SMILES: CCS(=O)(=O)N1CCN(c2ccc(Nc3ncc(C(N)=O)c(NC4CC4)n3)cc2F)CC1] | 4-(cyclopropylamino)-2-((4-(4-(ethylsulfonyl)piperazin-1-yl)-3-fluorophenyl)amino)pyrimidine-5-carboxamide |
| 43 | 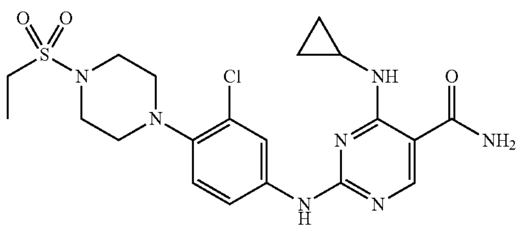 [SMILES: CCS(=O)(=O)N1CCN(c2ccc(Nc3ncc(C(N)=O)c(NC4CC4)n3)cc2Cl)CC1] | 2-((3-chloro-4-(4-(ethylsulfonyl)piperazin-1-yl)phenyl)amino)-4-(cyclopropylamino)pyrimidine-5-carboxamide |
| 44 | 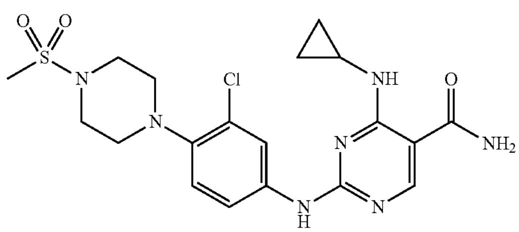 [SMILES: CS(=O)(=O)N1CCN(c2ccc(Nc3ncc(C(N)=O)c(NC4CC4)n3)cc2Cl)CC1] | 2-((3-chloro-4-(4-(methylsulfonyl)piperazin-1-yl)phenyl)amino)-4-(cyclopropylamino)pyrimidine-5-carboxamide |
| 45 | 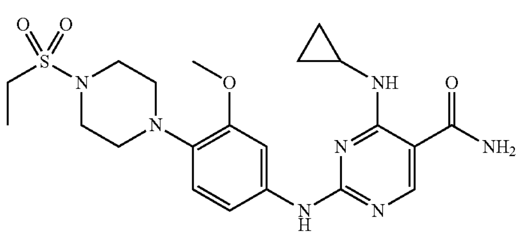 [SMILES: CCS(=O)(=O)N1CCN(c2ccc(Nc3ncc(C(N)=O)c(NC4CC4)n3)cc2OC)CC1] | 4-(cyclopropylamino)-2-((4-(4-(ethylsulfonyl)piperazin-1-yl)-3-methoxyphenyl)amino)pyrimidine-5-carboxamide |
| 46 | 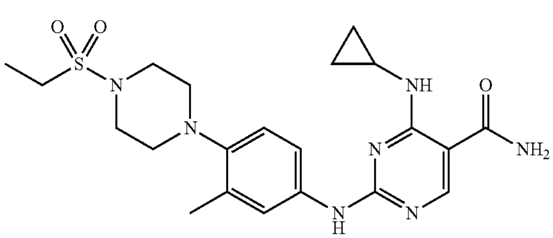 [SMILES: CCS(=O)(=O)N1CCN(c2ccc(Nc3ncc(C(N)=O)c(NC4CC4)n3)cc2C)CC1] | 4-(cyclopropylamino)-2-((4-(4-(ethylsulfonyl)piperazin-1-yl)-3-methylphenyl)amino)pyrimidine-5-carboxamide |

| Example No. | Structure | Compound Name |
|---|---|---|
| 47 | 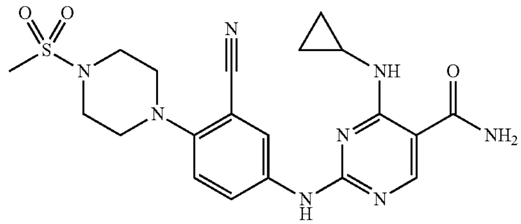 [SMILES: CS(=O)(=O)N1CCN(c2ccc(Nc3ncc(C(N)=O)c(NC4CC4)n3)cc2C#N)CC1] | 2-((3-cyano-4-(4-(methylsulfonyl)piperazin-1-yl)phenyl)amino)-4-(cyclopropylamino)pyrimidine-5-carboxamide |
| 48 | 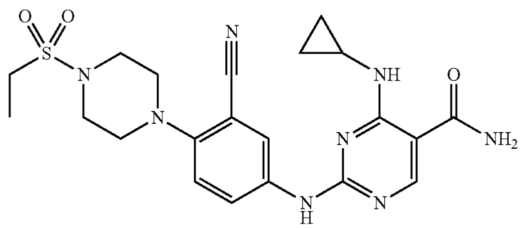 | 2-((3-cyano-4-(4-(ethylsulfonyl)piperazin-1-yl)phenyl)amino)-4-(cyclopropylamino)pyrimidine-5-carboxamide |
| 49 | 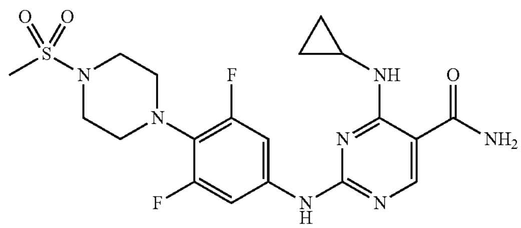 [SMILES: CS(=O)(=O)N1CCN(c2c(F)cc(Nc3ncc(C(N)=O)c(NC4CC4)n3)cc2F)CC1] | 4-(cyclopropylamino)-2-((3,5-difluoro-4-(4-(methylsulfonyl)piperazin-1-yl)phenyl)amino)pyrimidine-5-carboxamide |
| 50 | | 4-(cyclopropylamino)-2-((4-(4-(ethylsulfonyl)piperazin-1-yl)-3,5-difluorophenyl)amino)pyrimidine-5-carboxamide | or a tautomer or a pharmaceutically acceptable salt thereof.

In one group of embodiments, provided is a compound of Formula (Ic) that is selected from the group consisting of:

| Example No. | Structure | Compound Name |
|---|---|---|
| 51 | 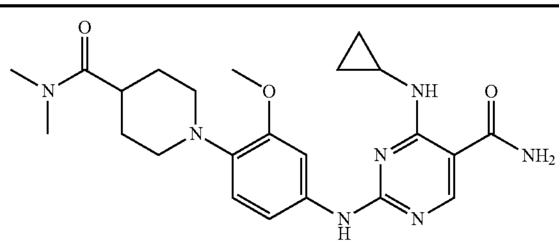 | 4-(cyclopropylamino)-2-((4-(4-(dimethylcarbamoyl)piperidin-1-yl)-3-methoxyphenyl)amino)pyrimidine-5-carboxamide |

| Example No. | Structure | Compound Name |
|---|---|---|
| 52 | 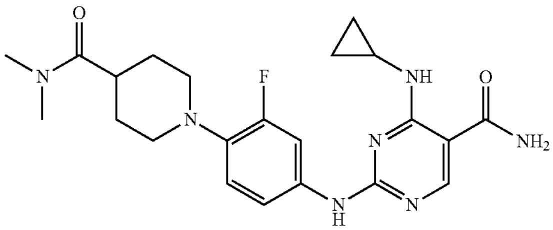 [SMILES: CN(C)C(=O)C1CCN(c2ccc(Nc3ncc(C(N)=O)c(NC4CC4)n3)cc2F)CC1] | 4-(cyclopropylamino)-2-((4-(4-(dimethylcarbamoyl)piperidin-1-yl)-3-fluorophenyl)amino)pyrimidine-5-carboxamide |
| 53 | | 2-((3-chloro-4-(4-(dimethylcarbamoyl)piperidin-1-yl)phenyl)amino)-4-(cyclopropylamino)pyrimidine-5-carboxamide | or a tautomer or a pharmaceutically acceptable salt thereof.

In one group of embodiments, provided is a compound of Formula (I) that is selected from the group consisting of:

| Example No. | Structure | Compound Name |
|---|---|---|
| 54 | 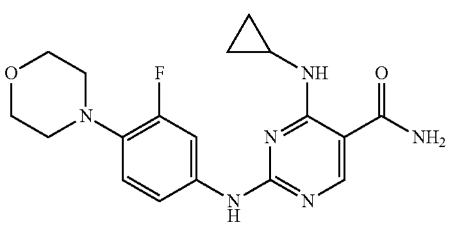 [SMILES: NC(=O)c1cnc(Nc2ccc(N3CCOCC3)c(F)c2)nc1NC1CC1] | 4-(cyclopropylamino)-2-((3-fluoro-4-morpholinophenyl)amino)pyrimidine-5-carboxamide |
| 55 | 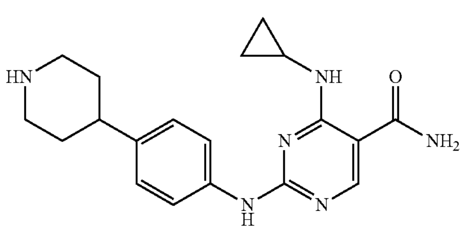 [SMILES: NC(=O)c1cnc(Nc2ccc(C3CCNCC3)cc2)nc1NC1CC1] | 4-(cyclopropylamino)-2-((4-(piperidin-4-yl)phenyl)amino)pyrimidine-5-carboxamide |
| 56 | 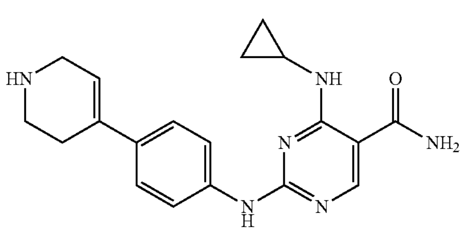 [SMILES: NC(=O)c1cnc(Nc2ccc(C3=CCNCC3)cc2)nc1NC1CC1] | 4-(cyclopropylamino)-2-((4-(1,2,3,6-tetrahydropyridin-4-yl)phenyl)amino)pyrimidine-5-carboxamide |

-continued

| Example No. | Structure | Compound Name |
|---|---|---|
| 57 | 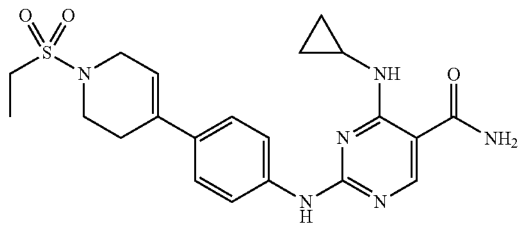 | 4-(cyclopropylamino)-2-((4-(1-(ethylsulfonyl)-1,2,3,6-tetrahydropyridin-4-yl)phenyl)amino)pyrimidine-5-carboxamide |
| 58 | 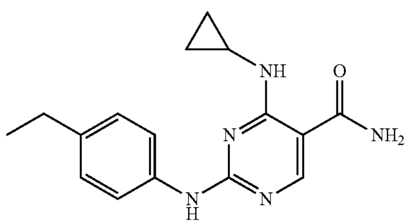 [SMILES: CCc1ccc(Nc2ncc(C(N)=O)c(NC3CC3)n2)cc1] | 4-(cyclopropylamino)-2-((4-isopropylphenyl)amino)pyrimidine-5-carboxamide |
| 59 | 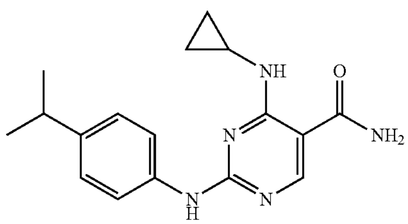 [SMILES: CC(C)c1ccc(Nc2ncc(C(N)=O)c(NC3CC3)n2)cc1] | 4-(cyclopropylamino)-2-((4-isopropylphenyl)amino)pyrimidine-5-carboxamide |
| 60 | 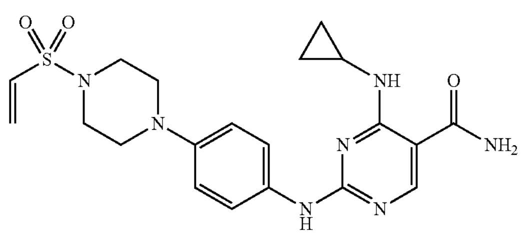 [SMILES: C=CS(=O)(=O)N1CCN(c2ccc(Nc3ncc(C(N)=O)c(NC4CC4)n3)cc2)CC1] | 4-(cyclopropylamino)-2-((4-(4-(vinylsulfonyl)piperazin-1-yl)phenyl)amino)pyrimidine-5-carboxamide |
| 61 | 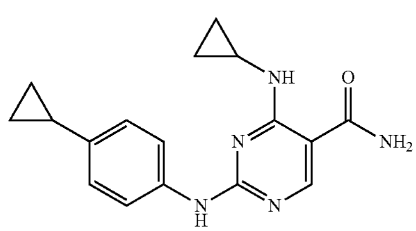 [SMILES: NC(=O)c1cnc(Nc2ccc(C3CC3)cc2)nc1NC1CC1] | 4-(cyclopropylamino)-2-((4-cyclopropylphenyl)amino)pyrimidine-5-carboxamide |
| 62 | | 4-(cyclopropylamino)-2-((4-(trifluoromethyl)phenyl)amino)pyrimidine-5-carboxamide | or a tautomer or a pharmaceutically acceptable salt thereof.

In one group of embodiments, provided is a compound of Formula (II):

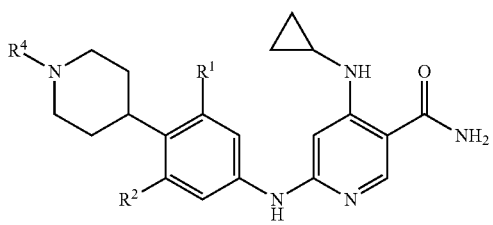

(II)

or a tautomer or a pharmaceutically acceptable salt thereof, wherein

R¹ is selected from the group consisting of H, halo, $C_{1-4}$alkoxy, and cyano;

R² is selected from the group consisting of H, halo, and $C_{1-4}$alkyl;

R⁴ is selected from the group consisting of H and $C_{1-4}$alkylS(O)$_2$.

In one group of embodiments, provided is a compound of Formula (II), wherein R⁴ is ethylS(O)$_2$; and wherein the other variables and provisos are as defined for any one of the groups of embodiments of Formula (II) above.

In one group of embodiments, provided is a compound of Formula (II), wherein R¹ and R² are H; and wherein the other variables and provisos are as defined for any one of the groups of embodiments of Formula (II) above.

In one group of embodiments, provided is a compound of Formula (II) that is selected from the group consisting of:

or a tautomer or a pharmaceutically acceptable salt thereof.

In one group of embodiments, provided is a compound of Formula (III):

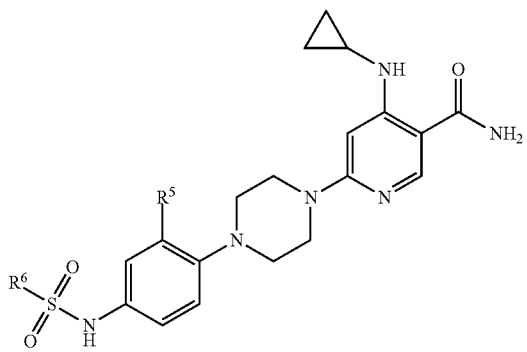

(III)

or a tautomer or a pharmaceutically acceptable salt thereof, wherein

R⁵ is selected from the group consisting of H and $C_{1-4}$alkoxy; and

R⁶ is $C_{1-4}$alkyl.

In one group of embodiments, provided is a compound of Formula (III), wherein R⁶ is methylS(O)$_2$ or ethylS(O)$_2$; and wherein the other variables and provisos are as defined for the group of embodiments of Formula (III) above.

In one group of embodiments, provided is a compound of Formula (III), wherein R⁵ is methoxy; and wherein the other variables and provisos are as defined for any one of the groups of embodiments of Formula (III) above.

| Example No. | Structure | Compound Name |
|---|---|---|
| 63 | 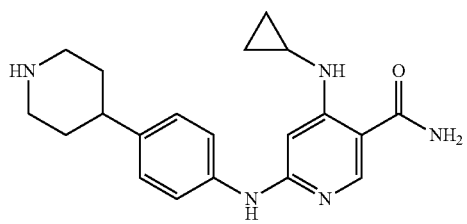 [SMILES: NC(=O)c1cnc(Nc2ccc(C3CCNCC3)cc2)cc1NC1CC1] | 4-(cyclopropylamino)-6-((4-(piperidin-4-yl)phenyl)amino)nicotinamide |
| 64 | 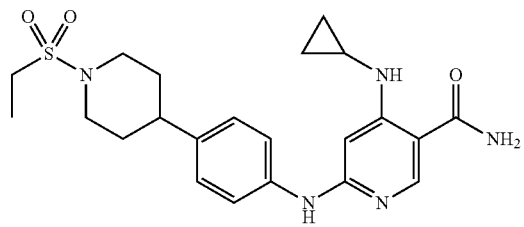 [SMILES: CCS(=O)(=O)N1CCC(c2ccc(Nc3cc(NC4CC4)c(C(N)=O)cn3)cc2)CC1] | 4-(cyclopropylamino)-6-((4-(1-(ethylsulfonyl)piperidin-4-yl)phenyl)amino)nicotinamide |

In one group of embodiments, provided is a compound of Formula (III) that is selected from the group consisting of

| Example No. | Structure | Compound Name |
| --- | --- | --- |
| 65 | 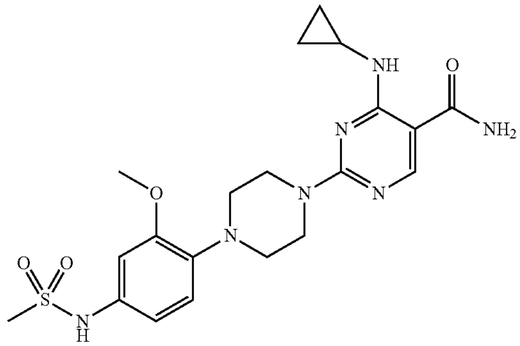 [SMILES: COc1cc(NS(C)(=O)=O)ccc1N1CCN(c2ncc(C(N)=O)c(NC3CC3)n2)CC1] | 4-(cyclopropylamino)-2-(4-(2-methoxy-4-(methylsulfonamido)phenyl)piperazin-1-yl)pyrimidine-5-carboxamide |
| 66 | | 4-(cyclopropylamino)-2-(4-(4-(ethylsulfonamido)-2-methoxyphenyl)piperazin-1-yl)pyrimidine-5-carboxamide | or a tautomer or a pharmaceutically acceptable salt thereof.

In one group of embodiments, provided is a compound selected from the group consisting of

| Example No. | Structure | Compound Name |
| --- | --- | --- |
| 67 | 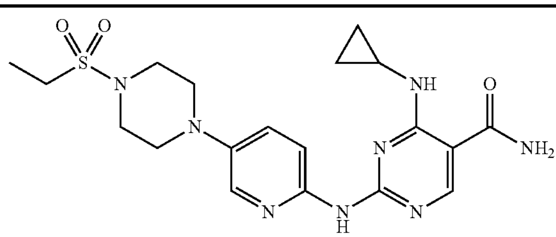 | 4-(cyclopropylamino)-2-((5-(4-(ethylsulfonyl)piperazin-1-yl)pyridin-2-yl)amino)pyrimidine-5-carboxamide |
| 68 | | 6-(cyclopropylamino)-4-((4-(piperidin-4-yl)phenyl)amino)nicotinamide | or a tautomer or a pharmaceutically acceptable salt thereof.

In one group of embodiments, provided is a compound selected from the group consisting of

| Example No. | Structure | Compound Name |
|---|---|---|
| 69 | 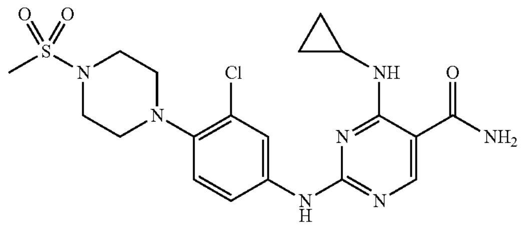 | 2-((3-chloro-4-(4-(methylsulfonyl)piperazin-1-yl)phenyl)amino)-4-(cyclopropylamino)pyrimidine-5-carboxamide |
| 70 | | 4-(cyclopropylamino)-2-((4-fluorophenyl)amino)pyrimidine-5-carboxamide | or a tautomer or a pharmaceutically acceptable salt thereof.

In one group of embodiments, provided is a compound of Formula (IVa):

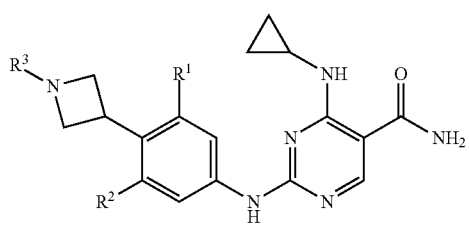

(IVa)

or a tautomer or a pharmaceutically acceptable salt thereof.

In one group of embodiments, provided is a compound wherein $R^3$ is selected from the group consisting of $C_{1-5}$alkyl, halo$C_{1-4}$alkyl, cyano$C_{1-4}$alkylene, $C_{3-6}$cycloalkyl, oxetan-3-yl, 1-cyclopropylpiperidin-4-yl, tetrahydropyran-4-yl, phenyl, HC(O), $R^{3a}C(O)$, $R^{3b}S(O)_2$, $R^{3c}S(O)_2$, pyridin-2-yl, 3-fluoropyridin-2-yl, and pyridin-3-yl.

In one group of embodiments, provided is a compound wherein $R^3$ is $R^{3b}S(O)_2$; and wherein $R^{3b}$ is selected from the group consisting of methyl, ethenyl and dimethylamino.

In one group of embodiments, provided is a compound wherein R is $R^{3a}C(O)$.

In one group of embodiments, provided is a compound wherein $R^{3a}$ is selected from the group consisting of methyl, methoxymethyl, and dimethylamino.

In one group of embodiments, provided is a compound wherein $R^1$ is H or F; and $R^2$ is H.

In one group of embodiments, provided is a compound is of Formula (IVb):

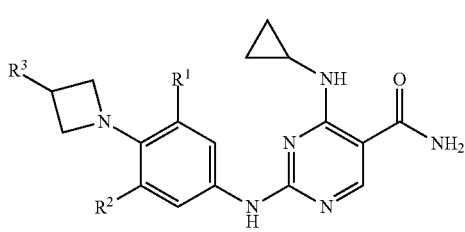

(IVb)

or a tautomer or a pharmaceutically acceptable salt thereof.

In one group of embodiments, provided is a compound wherein $R^3$ is $R^{3a}C(O)$.

In one group of embodiments, provided is a compound wherein $R^{3a}$ is dimethylamino.

In one group of embodiments, provided is a compound, wherein $R^1$ is H or F; and $R^2$ is H.

In one group of embodiments, provided is a compound selected from the group consisting of the following compounds:

| Example No. | Structure | Compounds Name |
|---|---|---|
| 71 | 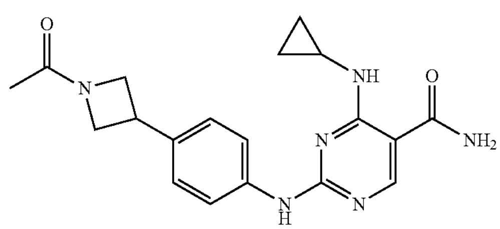 [SMILES: CC(=O)N1CC(c2ccc(Nc3ncc(C(N)=O)c(NC4CC4)n3)cc2)C1] | 2-(4-(1-acetylazetidin-3-yl)phenylamino)-4-(cyclopropylamino)pyrimidine-5-carboxamide |

-continued

| Example No. | Structure | Compounds Name |
|---|---|---|
| 72 | 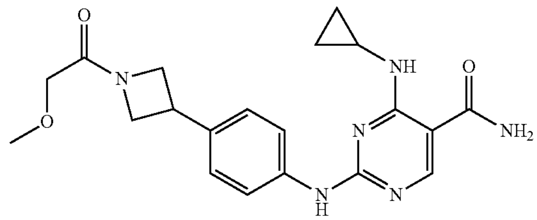 [SMILES: COCC(=O)N1CC(c2ccc(Nc3ncc(C(N)=O)c(NC4CC4)n3)cc2)C1] | 4-(cyclopropylamino)-2-(4-(1-(2-methoxyacetyl)azetidin-3-yl)phenylamino)pyrimidine-5-carboxamide |
| 73 | 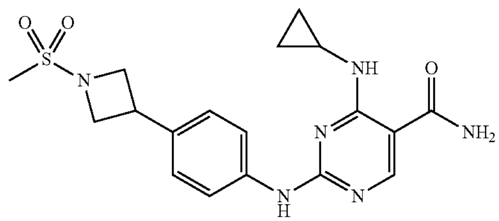 [SMILES: CS(=O)(=O)N1CC(c2ccc(Nc3ncc(C(N)=O)c(NC4CC4)n3)cc2)C1] | 4-(cyclopropylamino)-2-(4-(1-(methylsulfonyl)azetidin-3-yl)phenylamino)pyrimidine-5-carboxamide |
| 74 | 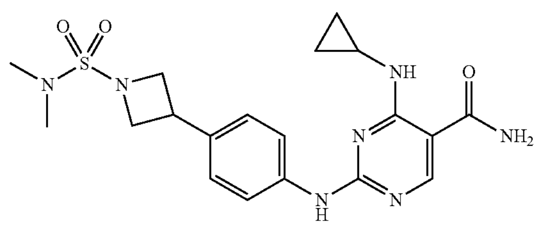 [SMILES: CN(C)S(=O)(=O)N1CC(c2ccc(Nc3ncc(C(N)=O)c(NC4CC4)n3)cc2)C1] | 4-(cyclopropylamino)-2-(4-(1-(N,N-dimethylsulfamoyl)azetidin-3-yl)phenylamino)pyrimidine-5-carboxamide |
| 75 | 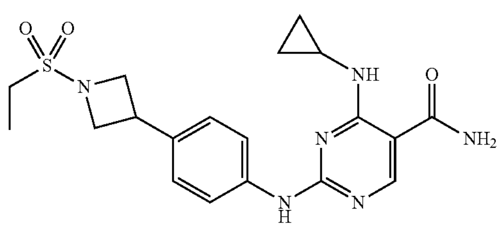 [SMILES: CCS(=O)(=O)N1CC(c2ccc(Nc3ncc(C(N)=O)c(NC4CC4)n3)cc2)C1] | 4-(cyclopropylamino)-2-(4-(1-(ethylsulfonyl)azetidin-3-yl)phenylamino)pyrimidine-5-carboxamide |
| 76 | 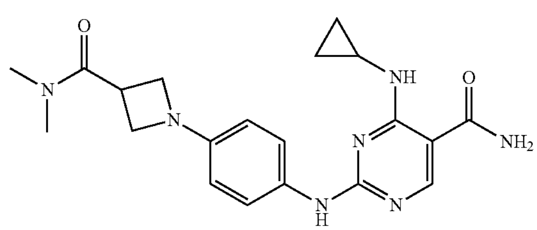 [SMILES: CN(C)C(=O)C1CN(c2ccc(Nc3ncc(C(N)=O)c(NC4CC4)n3)cc2)C1] | 4-(cyclopropylamino)-2-(4-(3-(dimethylcarbamoyl)azetidin-1-yl)phenylamino)pyrimidine-5-carboxamide |
| 77 | | 4-(cyclopropylamino)-2-(4-(3-(dimethylcarbamoyl)azetidin-1-yl)-3-fluorophenylamino)pyrimidine-5-carboxamide | or a tautomer or a pharmaceutically acceptable salt thereof.

In one group of embodiments, the compounds, tautomers thereof, or salts thereof provided herein are in purified forms.

The compounds of the present invention may be prepared by known organic synthesis techniques, including the methods described in more detail in the Examples.

In one group of embodiments, provided is an intermediate compound used in the preparation of the compounds disclosed herein.

In one group of embodiments, provided are methods for preparing the compounds disclosed herein.

In one group of embodiments, certain of the compounds disclosed herein may generally be utilized as the free base. Alternatively, certain of the compounds may be used in the form of acid addition salts.

It is understood that in another group of embodiments, for any of the above embodiments (e.g., a specific substituent at a site, e.g., selected from a particular embodiment or the Markush group described in a group of embodiments herein), a specific element may also be combined with other embodiments listed herein, to form other embodiments of the invention.

Similarly, it is understood that in other embodiments, listing of groups includes embodiments wherein one or more of the elements of those groups is not included. For example, if a group of embodiments includes a Markush group composed of a list of x elements, there are other embodiments presenting a group of (x–n) elements taken from the list, where n is any integer from 1 to (x–1).

It is understood that in another group of embodiments, any of the above embodiments (e.g., a specific substituent at a site, e.g., selected from a particular embodiment or the Markush group described in a group of embodiments herein); a specific element may also be combined with other embodiments listed herein, to form other embodiments of the invention. Similarly, it is understood that in other embodiments, listing of groups includes embodiments wherein one or more of the compounds of those groups is not included. For example, if a group of embodiments includes a Markush group composed of a list of x compounds, there are embodiments presenting a group of (x–n) compounds taken from the list, where n is any integer from 1 to (x–1).

Compositions and Methods of Administration

In one group of embodiments, provided is a composition (e.g., a pharmaceutical composition) comprising a compound of any one of the embodiments or groups of embodiments herein, or a tautomer or a pharmaceutically acceptable salt thereof, in combination with a pharmaceutically acceptable carrier or diluent.

Depending on the intended mode of administration, the pharmaceutical compositions may be in the form of solid, semi-solid or liquid dosage forms, preferably in unit dosage form suitable for single administration of a precise dosage. In addition to an effective amount of the active compound(s), the compositions may contain suitable pharmaceutically-acceptable excipients, including adjuvants that facilitate processing of the active compounds into preparations that can be used pharmaceutically.

For solid compositions, conventional excipients include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by dissolving, dispersing, etc., an active compound as described herein and optional pharmaceutical adjuvants in water or an aqueous excipient, such as, for example, water, saline, aqueous dextrose, and the like, to form a solution or suspension. If desired, the pharmaceutical composition to be administered may also contain minor amounts of nontoxic auxiliary excipients such as wetting or emulsifying agents, pH buffering agents and the like, for example, sodium acetate, sorbitan monolaurate, triethanolamine sodium acetate, triethanolamine oleate, etc.

The term "administering" refers to administration by any route, including parenteral and transmucosal (e.g., buccal, sublingual, palatal, gingival, nasal, vaginal, rectal, or transdermal).

For oral administration, the composition will generally take the form of a tablet or capsule, or it may be an aqueous or nonaqueous solution, suspension, or syrup. Tablets and capsules are preferred oral administration forms. Tablets and capsules for oral use will generally include one or more commonly used excipients such as lactose and corn starch. Lubricating agents, such as magnesium stearate, are also typically added. When liquid suspensions are used, the active agent may be combined with emulsifying and suspending excipients. If desired, flavoring, coloring and/or sweetening agents may be added as well. Other optional excipients for incorporation into an oral formulation include preservatives, suspending agents, thickening agents, and the like.

Injectable formulations can be prepared in conventional forms, either as liquid solutions or suspensions, solid forms suitable for solubilization or suspension in liquid prior to injection, or as emulsions or liposomal formulations. The sterile injectable formulation may also be a sterile injectable solution or a suspension in a nontoxic parenterally acceptable diluent or solvent. Among the acceptable vehicles and solvents that may be employed are water, Ringer's solution, and isotonic sodium chloride solution. In addition, sterile, fixed oils, fatty esters or polyols are conventionally employed as solvents or suspending media.

The pharmaceutical compositions of this invention may also be formulated in lyophilized form for parenteral administration. Lyophilized formulations may be reconstituted by addition of water or other aqueous medium and then further diluted with a suitable diluent prior to use. The liquid formulation is generally a buffered, isotonic, aqueous solution. Examples of suitable diluents are isotonic saline solution, 5% dextrose in water, and buffered sodium or ammonium acetate solution. Pharmaceutically acceptable solid or liquid excipients may be added to enhance or stabilize the composition, or to facilitate preparation of the composition.

Typically, a pharmaceutical composition of the present invention is packaged in a container with a label, or instructions, or both, indicating use of the pharmaceutical composition in the treatment of the indicated disease.

The pharmaceutical composition may additionally contain one or more other pharmacologically active agents in addition to a compound of this invention.

Dosage forms containing effective amounts of the modulators are within the bounds of routine experimentation and within the scope of the invention. A therapeutically effective dose may vary depending upon the route of administration and dosage form. The representative compound or compounds of the invention is a formulation that exhibits a high therapeutic index.

The therapeutic index is the dose ratio between toxic and therapeutic effects, which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals. It should be understood that a specific dosage and treatment regimen for any particular patient will depend upon a variety of factors, including the activity of the specific compound employed, the age, body weight, general health, sex and diet of the patient, and the time of administration, rate of excretion, drug combination, judgment of the treating physician and severity of the particular disease being treated. The amount of active ingredient(s) will also depend upon the particular compound and other therapeutic agent, if present, in the composition.

The compounds disclosed herein have utility over a wide range of therapeutic applications, and may be used to treat a variety of conditions, mediated at least in part by JAK and/or Syk kinase. For example, such conditions include, but are not limited to, those associated with cardiovascular disease, inflammatory disease, autoimmune disease, or a cell proliferative disorder.

Cardiovascular diseases are include but are not limited to restenosis, thrombosis, immune thrombocytopenic purpura, heparin induced thrombocytopenia, dilated cardiomyopathy, sickle cell disease, atherosclerosis, myocardial infarction, vascular inflammation, unstable angina, and acute coronary syndromes.

Inflammatory diseases include but are not limited to allergy, asthma, rheumatoid arthritis. B-cell mediated diseases, non-Hodgkin's lymphoma, anti-phospholipid syndrome, lupus, psoriasis, multiple sclerosis, and end stage renal disease.

Autoimmune disease include but are not limited to hemolytic anemia, immune thrombocytopenic purpura, multiple sclerosis. Sjogren's syndrome, diabetes, rheumatoid arthritis, lupus, and psoriasis.

Cell proliferative disorders include but are not limited to leukemia, a lymphoma, myeloproliferative disorders, hematological malignancies, and chronic idiopathic myelofibrosis.

In one group of embodiments, provided is a method for inhibiting the JAK and/or Syk activity of a blood sample comprising contacting said sample with a compound or a pharmaceutically acceptable salt thereof as disclosed herein.

In one group of embodiments, provided is a method for inhibiting Syk or JAK kinase comprising contacting a cell with a compound of any one of the embodiments or groups of embodiments herein.

In one group of embodiments, provided is a method for treating a condition or disorder mediated at least in part by Syk or JAK kinase activity comprising administering to a subject in need of such treatment a therapeutically effective amount of a composition of an embodiment or group of embodiments as disclosed herein.

In one group of embodiments, provided is a method as disclosed in any embodiment or group of embodiments herein, wherein the condition or disorder is selected from the group consisting of cardiovascular disease, inflammatory disease, autoimmune disease, and cell proliferative disorder.

In one group of embodiments, provided is a method as disclosed in any embodiment or group of embodiments herein, wherein said cardiovascular disease is selected from the group consisting of restenosis, thrombosis, immune thrombocytopenic purpura, heparin induced thrombocytopenia, dilated cardiomyopathy, sickle cell disease, atherosclerosis, myocardial infarction, vascular inflammation, unstable angina, and acute coronary syndromes;

said inflammatory disease is selected from the group consisting of allergy, asthma, rheumatoid arthritis, B-cell mediated diseases, non-Hodgkin's lymphoma, anti-phospholipid syndrome, lupus, psoriasis, multiple sclerosis, and end stage renal disease;

said autoimmune disease is selected from the group consisting of hemolytic anemia, immune thrombocytopenic purpura, multiple sclerosis, Sjogren's syndrome, diabetes, rheumatoid arthritis, lupus, and psoriasis; and said cell proliferative disorder is selected from the group consisting of leukemia, a lymphoma, myeloproliferative disorders, hematological malignancies, and chronic idiopathic myelofibrosis.

In one group of embodiments, provided is a method as disclosed in any embodiment or group of embodiments herein, wherein said B-cell mediated disease is a B-cell malignancy.

In one group of embodiments, provided is a method as disclosed in any embodiment or group of embodiments herein, wherein said B-cell malignancy is selected from the group consisting of chronic lymphocytic leukemia, diffuse large B-cell lymphoma, mantle cell lymphoma and follicular lymphoma.

EXAMPLES

The following examples are offered to illustrate, but not to limit, the claimed invention.

Preparative Examples

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1967-2004, Volumes 1-22; *Rodd's Chemistry of Carbon Compounds*. Elsevier Science Publishers, 1989, Volumes 1-5 and Supplemental; and Organic Reactions, Wiley & Sons: New York, 2005, Volumes 1-65.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C. to about 75° C.

Scheme 1: General Method of Synthetic Preparation:

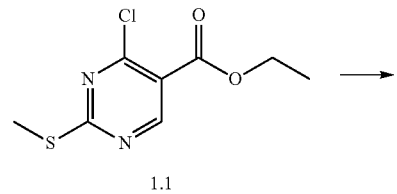

1.1

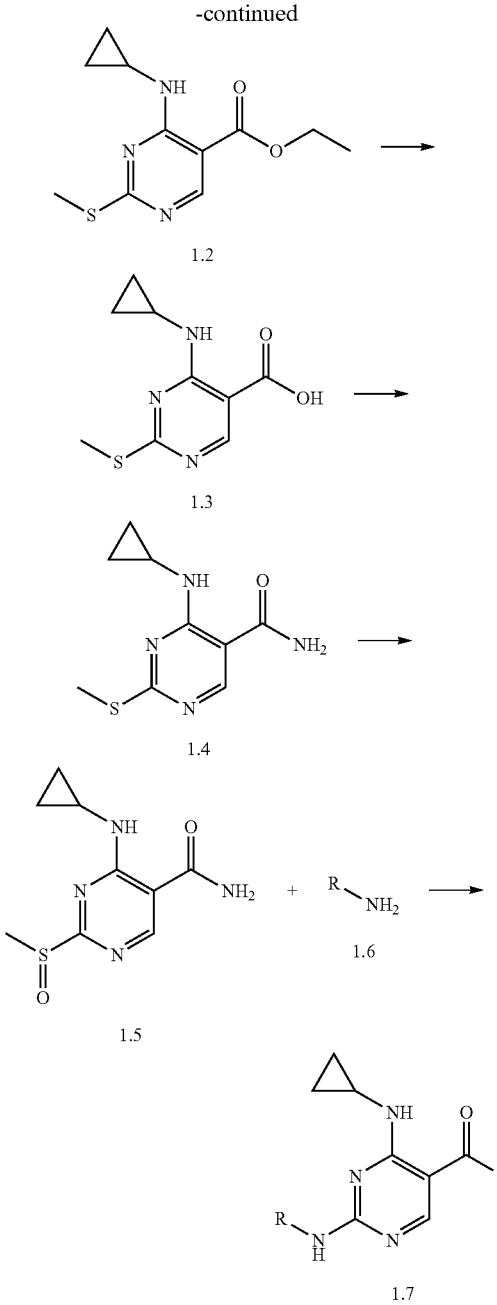

Step 1:

To a suspension of 1.1 (100 g, 430 mmol) in 200 mL of acetonitrile was added diisopropyl ethyl amine (DIEA) (81 mL, 470 mmol) as a steady stream (no change in temperature, reaction mixture still a suspension), followed by slow addition of cyclopropylamine (32.6 mL, 470 mmol) over about 5 min, during which time the reaction became warm. As the addition progressed, the rate of addition was changed to maintain a gentle reflux at the top of the flask. During the addition of the amine, the suspension began to dissolve and eventually the reaction was a pale yellow solution. The reaction was checked after all the amine had been added and a small amount of starting material was found to be present. 2 mL of cyclopropylamine was added; the reaction was rechecked and found to be complete. The reaction mixture was concentrated to remove the acetonitrile, then diluted with water to ca. 700 mL total volume. After vigorous stirring, an oil was present. This mixture was acidified to pH=3 with 3 M HCl and stirred vigorously, resulting in no change. Swirling or slow stirring gave no filterable precipitate. After adjusting the pH to 5 with saturated $Na_2CO_3$ (the mixture was now approximately 800-900 mL total volume), the reaction was allowed to stir slowly, and after 30 min, a precipitate formed. Vigorous stirring was then resumed, and after 1 hr, the precipitate was isolated by filtration as a granular chunky solid. The solid was broken down with a spatula, and the solids washed with water affording the desired product as a slightly off-white solid, which was >95% pure by UPLC. This material contains water, so it is carried into the next step using the theoretical yield as the basis for calculating the equivalents.

Step 2:

The crude solid from Step 1 was suspended in 400 mL of dioxane and 400 mL of water. To this suspension was added solid LiOH (15.5 g, 645 mmol, 1.5 eq), and the reaction was stirred at rt. After ca. 30 min, the LiOH dissolved, and the reaction mixture became a cloudy yellow solution. After 1 hr, UPLC revealed the reaction had progressed 50%; the appearance was still a light yellow opaque solution. The following morning, the reaction was checked and determined to be complete. The mixture was then diluted with water to 1.6 L total volume and acidified to pH=2 with 6 M HCl, then stirred until the solid became homogeneous and flowed as a suspension. It was then collected by filtration and washed with portions of water (the solid was collected in three filter funnels, then combined into one after drying for a few hours, the water washes being used to assist in the transfer of the solid). The solids were aspirated to remove most of the water, then dried over the weekend (58.53 g, 60% for two steps).

Step 3:

Carboxylic acid 1.3 (21 g, 93 mmol) was dissolved in 133 mL of DMF, and then treated with HOBt (14 g, 103 mmol) and EDC (21 g, 112 mmol). After stirring 30 min, the reaction was checked by UPLC, which showed complete formation of the activated intermediate. Ammonia (aq) (11 mL, 186 mmol) was then added slowly to the stirred solution, and the resulting mixture was stirred until the reaction was determined to be complete by UPLC (20-120 min). The reaction mixture was then diluted with water to 900 mL total volume, stirred, and then the solid was isolated by filtration and dried by aspiration, affording 19.83 g (95%) of the desired amide as a white solid.

Step 4:

Thioether 1.4 (34 g, 152 mmol) was suspended in 500 mL of ACN, then treated with 36 mL (213 mmol) of peroxyacetic acid in acetic acid (added over ca. 15 seconds), which resulted in a slight increase in temperature and no significant dissolution of the insoluble starting material. After being stirred for 1 hr. the reaction was checked by UPLC, which showed a small amount of the starting thioether. The reaction was treated with 3.6 mL of the oxidant and stirred for an additional 1 hr. UPLC analysis showed a trace of starting material and a small amount of sulfone. The solid was then collected by filtration, washed with small portions of acetonitrile and aspirated to dryness. The combined yield of two batches (20 g and 34 g, 241 mmol total) was 37.91 g (158 mmol, 66%) that was >95% pure by UPLC, containing only a trace of starting material and the sulfone.

Step 5:

Sulfoxide 1.5 (16.61 g, 69 mmol) was treated with aniline 1.6 (19 g, 83 mmol) and TsOH—$H_2O$ (15.8 g, 83 mmol), then diluted with 70 mL of NMP and heated to 100° C. The reaction changed from a dark orange suspension (the aniline had some color) to a solution. After heating for 40 min, a precipitate formed. The reaction was checked by UPLC, which showed complete conversion to the desired product. The reaction was cooled to room temperature, during which time more precipitate formed. Water was then added to the stirring mixture to a total volume of 200 mL, during which time a light beige precipitate formed. The precipitate was then isolated by filtration and washed with small portions of water until the filtrate was colorless. The solid was then dried overnight by aspiration affording 34.82 g (87%) of the desired product as a toluenesulfonic acid salt. Alternatively, the crude reaction mixture can be immediately purified by preparative HPLC using acetonitrile/water as a solvent and either trifluoroacetic acid or hydrochloric acid as a modifier.

Example 1: 4-(Cyclopropylamino)-2-((3-fluoro-4-morpholinophenyl)amino)pyrimidine-5-carboxamide

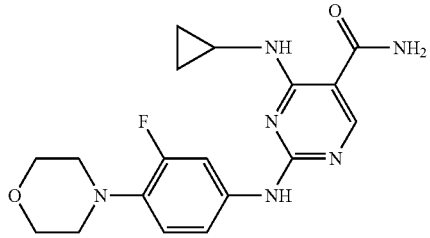 [SMILES: NC(=O)c1cnc(Nc2ccc(N3CCOCC3)c(F)c2)nc1NC1CC1]

The title compound was synthesized with 3-fluoro-4-morpholinoaniline in a manner similar to that described in Scheme 1 using commercially morpholinoaniline. MS found for $C_{18}H_{21}FN_6O_2$ as $(M+H)^+=373.4$. UV: λ 226, 287 nm.

Example 2: 4-(Cyclopropylamino)-2-((4-(piperidin-4-yl)phenyl)amino)pyrimidine-5-carboxamide

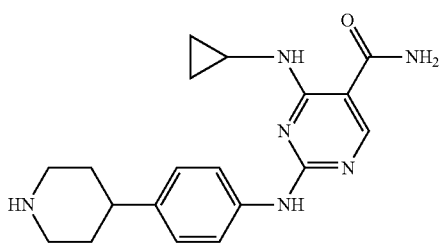 [SMILES: NC(=O)c1cnc(Nc2ccc(C3CCNCC3)cc2)nc1NC1CC1]

Compound tert-butyl 4-(4-((5-carbamoyl-4-(cyclopropylamino)pyrimidin-2-yl)amino)phenyl)piperidine-1-carboxylate was synthesized with tert-butyl 4-(4-aminophenyl)piperidine-1-carboxylate in a manner similar to that described in Scheme 1. It was treated with TFA at 60° C. to afford the title compound, which was isolated by reverse-phase prep HPLC. MS found for $C_{19}H_{24}N_6O$ as $(M+H)^+=353.3$. UV: λ 268 nm.

Example 3: 4-(Cyclopropylamino)-2-((4-(1-(ethylsulfonyl)piperidin-4-yl)phenyl)amino)pyrimidine-5-carboxamide

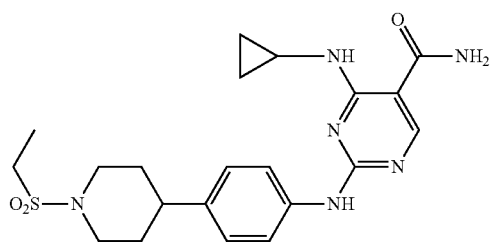 [SMILES: CCS(=O)(=O)N1CCC(c2ccc(Nc3ncc(C(N)=O)c(NC4CC4)n3)cc2)CC1]

The compound 4-(cyclopropylamino)-2-((4-(piperidin-4-yl)phenyl)amino)pyrimidine-5-carboxamide (220 mg, 0.42 mmol) was dissolved in 10 mL DMSO and stirred at room temperature. To the mixture were added diisopropyl ethyl amine (DIEA, 220 µL, 1.26 mmol) and then ethanesulfonyl chloride (80 µL, 0.84 mmol). The mixture was stirred for 30 m and quenched with water. The mixture was acidified with TFA and subjected to reverse-phase prep HPLC to isolate the title compound. MS found for $C_{21}H_{28}N_6O_3S$ as $(M+H)^+$ M+H=445.3. UV: λ 273 nm.

Example 4: 4-(Cyclopropylamino)-2-(3-fluoro-4-(4-(methylsulfonyl)piperazin-1-yl)phenylamino)pyrimidine-5-carboxamide

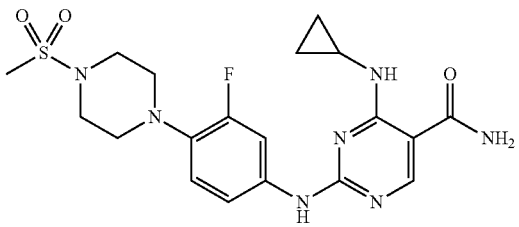 [SMILES: CS(=O)(=O)N1CCN(c2ccc(Nc3ncc(C(N)=O)c(NC4CC4)n3)cc2F)CC1]

The title compound was synthesized in a manner similar to that described in Scheme 1 using an aniline synthesized from 3,4-difluoronitrobenzene and Boc-piperazine, followed by Boc deprotection and subsequent reaction with methanesulfonyl chloride. Finally, the nitro group was reduced using Pd/C in methanol under an atmosphere of hydrogen. MS found for $C_{19}H_2FN_7O_3S$ as $(M+H)^+=450.1$. UV: λ 202, 239, 293. $^1$H NMR: (CD$_3$OD) δ 8.39 (s, 1H), 7.84 (m, 1H), 7.37 (d, 1H), 7.13 (t, 1H), 3.38 (m, 4H), 3.23 (m, 4H), 3.02 (m, 1H), 2.92 (s, 3H), 0.98 (m, 2H), 0.76 (m, 2H).

Example 5: 4-(Cyclopropylamino)-2-(4-(4-(ethylsulfonyl)piperazin-1-yl)-3-fluorophenylamino)pyrimidine-5-carboxamide

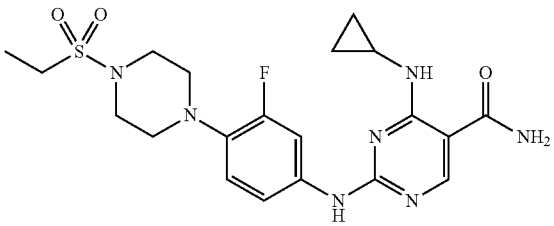 [SMILES: CCS(=O)(=O)N1CCN(c2ccc(Nc3ncc(C(N)=O)c(NC4CC4)n3)cc2F)CC1]

The title compound was synthesized in a manner similar to that described in Scheme 1. MS found for $C_{20}H_{26}FN_7O_3S$ as $(M+H)^+=464.2$. UV: λ 202, 229, 293. $^1$H NMR: (CD$_3$OD) δ 8.38 (s, 1H), 7.82 (m, 1H), 7.33 (d, 1H), 7.10 (t, 1H), 3.45 (m, 4H), 3.14 (m, 4H), 3.10 (q, 2H), 3.00 (m, 1H), 1.38 (t, 3H), 0.97 (m, 2H), 0.73 (m, 2H).

Example 6: 2-(3-Chloro-4-(4-(ethylsulfonyl)piperazin-1-yl)phenylamino)-4-(cyclopropylamino)pyrimidine-5-carboxamide

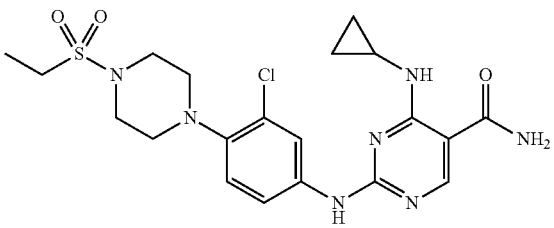 [SMILES: CCS(=O)(=O)N1CCN(c2ccc(Nc3ncc(C(N)=O)c(NC4CC4)n3)cc2Cl)CC1]

The title compound was synthesized in a manner similar to that described in Scheme 1, using an aniline prepared from 3-chloro-4-fluoronitrobenzene and Boc piperazine. MS found for $C_{20}H_{26}ClN_7O_3S$ as $(M+H)^+$ M+H=480. UV: λ 209, 290. $^1$H NMR: ($CD_3OD$) δ 8.42 (s, 1H), 8.26 (m, 1H), 7.47 (dd, 1H), 7.19 (d, 1H), 3.51 (m, 4H), 3.15 (m, 6H), 2.98 (m, 1H), 1.38 (t, 3H), 1.01 (m, 2H), 0.76 (m, 2H).

Example 7: 4-(Cyclopropylamino)-2-(4-(2-methoxy-4-(methylsulfonamido)phenyl)piperazin-1-yl)pyrimidine-5-carboxamide

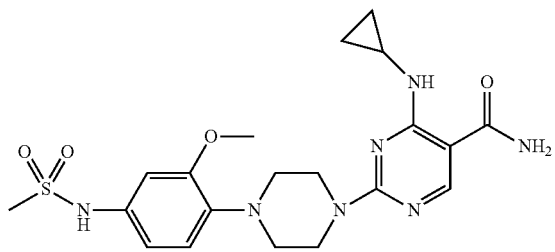 [SMILES: COc1cc(NS(C)(=O)=O)ccc1N1CCN(c2ncc(C(N)=O)c(NC3CC3)n2)CC1]

The title compound was synthesized with N-(3-methoxy-4-(piperazin-1-yl)phenyl)methanesulfonamide in a manner similar to that described in Scheme 1. MS found for $C_{20}H_{27}N_7O_4S$ as $(M+H)^+$=462.3. UV: λ 207.1, 246.1 nm.

Example 8: 4-(Cyclopropylamino)-2-(4-(4-(ethylsulfonamido)-2-methoxyphenyl)piperazin-1-yl)pyrimidine-5-carboxamide

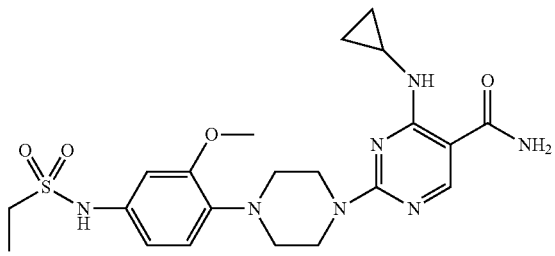 [SMILES: CCS(=O)(=O)Nc1ccc(N2CCN(c3ncc(C(N)=O)c(NC4CC4)n3)CC2)c(OC)c1]

The title compound was synthesized with N-(3-methoxy-4-(piperazin-1-yl)phenyl)ethanesulfonamide in a manner similar to that described in Scheme 1. MS found for $C_{21}H_{29}N_7O_4S$ as $(M+H)^+$=476.3. UV: λ 209.5, 246.1 nm.

Example 9: 4-(Cyclopropylamino)-2-((4-(1,2,3,6-tetrahydropyridin-4-yl)phenyl)amino)pyrimidine-5-carboxamide

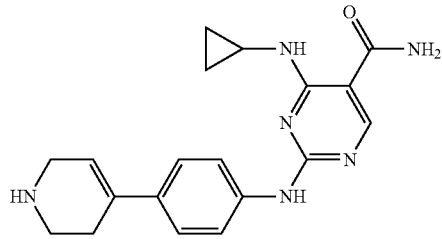 [SMILES: NC(=O)c1cnc(Nc2ccc(C3=CCNCC3)cc2)nc1NC1CC1]

The compound tert-butyl 4-(4-((5-carbamoyl-4-(cyclopropylamino)pyrimidin-2-yl)amino)phenyl)-5,6-dihydropyridine-1(2H)-carboxylate was synthesized with tert-butyl 4-(4-aminophenyl)-5,6-dihydropyridine-1(2H)-carboxylate in a manner similar to that described in Scheme 1. It was treated with TFA at 50° C. to afford the title compound, which was isolated by reverse-phase prep HPLC. MS found for $C_{19}H_{22}N_6O$ as $(M+H)^+$=351.2. UV: λ=292 nm.

Example 10: 4-(Cyclopropylamino)-2-(4-(4-(dimethylcarbamoyl)piperidin-1-yl)-3-methoxyphenylamino)pyrimidine-5-carboxamide

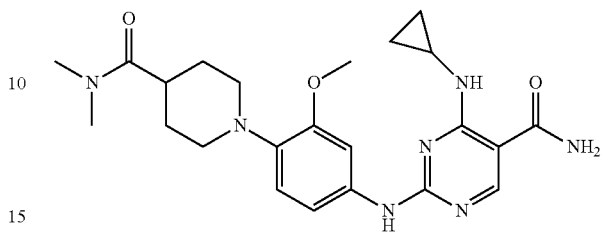

The title compound was synthesized with 1-(4-amino-2-methoxyphenyl)-N,N-dimethylpiperidine-4-carboxamide in a manner similar to that described in Scheme 1. MS found for $C_{23}H_{31}N_7O_3$ as $(M+H)^+$=454.3. UV: λ=204.7, 265.7 nm.

Example 11: 2-(3-Chloro-4-(4-(methylsulfonyl)piperazin-1-yl)phenylamino)-4-(cyclopropylamino)pyrimidine-5-carboxamide

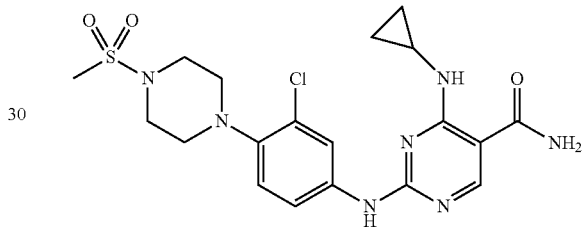

The title compound was synthesized in a manner similar to that described in Scheme 1 using an aniline similar to that described previously. MS found for $C_{19}H_{24}ClN_7O_3S$ as $(M+H)^+$ M+H=466. UV: λ=209, 289 nm. $^1$H NMR: (DMSO-d6) δ 9.67 (s, 1H), 9.14 (d, 1H, 2.4 Hz) 8.50 (s, 1H), 8.35 (broad s, 1H), 7.79 (broad s, 1H), 7.63 (dd, 1H, 2 Hz, 8.8 Hz), 7.15 (broad s, 1H), 7.13 (d, 1H, 8.8 Hz), 3.25 (m, 4H), 3.00 (m, 4H), 2.93 (s, 3H), 2.81 (m, 1H), 0.89 (m, 2H), 0.56 (m, 2H).

Example 12: 4-(Cyclopropylamino)-2-(4-(4-(dimethylcarbamoyl)piperidin-1-yl)-3-fluorophenylamino)pyrimidine-5-carboxamide

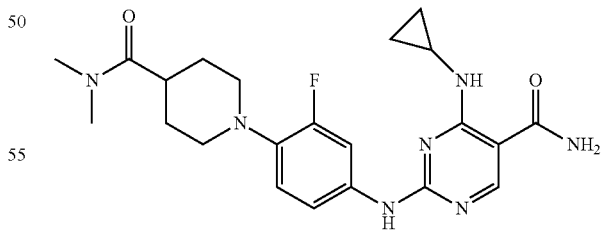

The title compound was synthesized in a manner similar to that described in Scheme 1 using an aniline prepared from 3,4-difluoronitrobenzene and ethyl isonipecotate, followed by saponification of the ethyl ester using LiOH/water/dioxane and amidation of the resulting carboxylic acid using dimethylamine using EDC and HOBt. Reduction of the nitro group was accomplished using hydrogen and Pd/C. MS found for $C_{22}H_{28}FN_7O_2$ as $(M+H)^+$=442.4. $^1$H NMR:

(DMSO-d6) δ 10.05 (broad s, 1H), 9.43 (broad s, 1H), 8.43 (s, 1H), 7.97 (broad s, 2H), 7.38 (d, 2H), 7.03 (t, 1H), 3.31 (m, 2H), 3.03 (s, 3H), 2.68-2.91 (m, 6H), 2.82 (s, 3H), 1.70 (m, 4H), 0.83 (m, 2H), 0.64 (m, 2H).

Example 13: 2-(3-Chloro-4-(4-(dimethylcarbamoyl)piperidin-1-yl)phenylamino)-4-(cyclopropylamino)pyrimidine-5-carboxamide

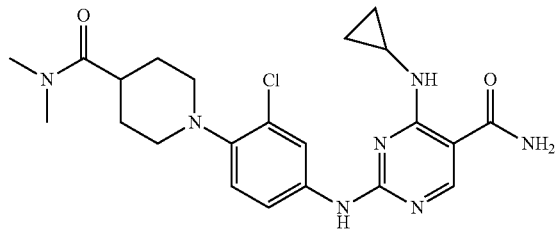 [SMILES: COc1cc(Nc2ncc(C(N)=O)c(NC3CC3)n2)ccc1N1CCC(C(=O)N(C)C)CC1]

The title compound was synthesized in a manner similar to that described in Scheme 1 using an aniline synthesized in a manner of that previously described. MS found for $C_{22}H_{28}ClN_7O_2$ as $(M+H)^+=458.3$. $^1$H NMR: (DMSO-d6) δ 10.03 (broad s, 1H), 9.43 (broad s, 1H), 8.44 (s, 1H), 8.20 (broad s, 1H), 7.96 (broad s, 2H), 7.54 (d, 1H), 7.39 (broad s, 1H), 7.09 (d, 1H), 3.22 (m, 2H), 3.03 (s, 3H), 2.83 (m, 1H), 2.82 (s, 3H), 2.79 (m, 5H), 1.71 (m, 4H), 0.88 (m, 2H), 0.60 (m, 2H).

Example 14: 4-(Cyclopropylamino)-2-((4-(1-(ethylsulfonyl)-1,2,3,6-tetrahydropyridin-4-yl)phenyl)amino)pyrimidine-5-carboxamide

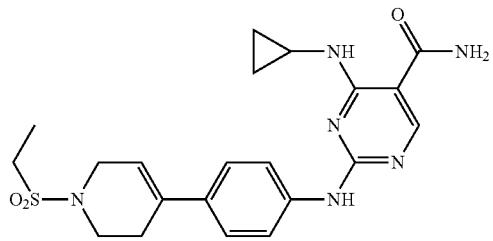 [SMILES: CCS(=O)(=O)N1CC=C(c2ccc(Nc3ncc(C(N)=O)c(NC4CC4)n3)cc2)CC1]

The title compound was synthesized in a manner similar to that described in Example 3 (i.e., 4-(cyclopropylamino)-2-((4-(1-(ethylsulfonyl)piperidin-4-yl)phenyl)amino)pyrimidine-5-carboxamide), but using 4-(cyclopropylamino)-2-((4-(1,2,3,6-tetrahydropyridin-4-yl)phenyl)amino)pyrimidine-5-carboxamide. MS found for $C_{21}H_{26}N_6O_3S$ as $(M+H)^+$ 443.2. UV: λ=297 nm.

Example 15: 4-(Cyclopropylamino)-2-((4-(1-(cyclopropylsulfonyl)piperidin-4-yl)phenyl)amino)pyrimidine-5-carboxamide

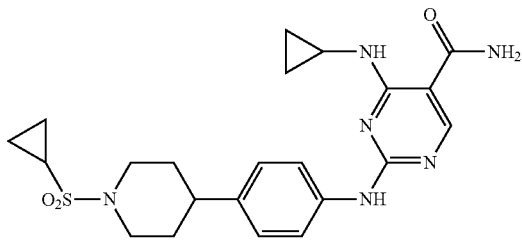 [SMILES: NC(=O)c1cnc(Nc2ccc(C3CCN(S(=O)(=O)C4CC4)CC3)cc2)nc1NC1CC1]

The title compound was synthesized in a manner similar to that described in Example 3 (i.e., 4-(cyclopropylamino)-2-((4-(1-(ethylsulfonyl)piperidin-4-yl)phenyl)amino)pyrimidine-5-carboxamide), but using cyclopropanesulfonyl chloride. MS found for $C_{22}H_{28}N_6)_3S$ as $(M+H)^+$ M+H=457.2. UV: λ=273 nm.

Example 16: 4-(Cyclopropylamino)-2-((4-(1-(isopropylsulfonyl)piperidin-4-yl)phenyl)amino)pyrimidine-5-carboxamide

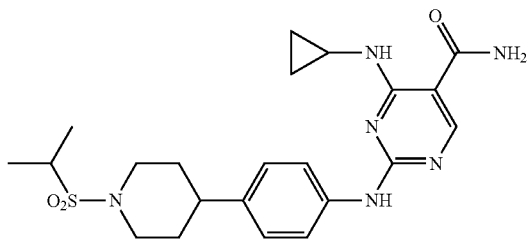

The title compound was synthesized in a manner similar to that described in Example 3 (i.e., 4-(cyclopropylamino)-2-((4-(1-(ethylsulfonyl)piperidin-4-yl)phenyl)amino)pyrimidine-5-carboxamide), but using propane-2-sulfonyl chloride. MS found for $C_{22}H_{30}N_6O_3S$ as $(M+H)^+=459.3$. UV: λ=273 nm.

Example 17: 4-(Cyclopropylamino)-2-((4-(1-isopropylpiperidin-4-yl)phenyl)amino)pyrimidine-5-carboxamide

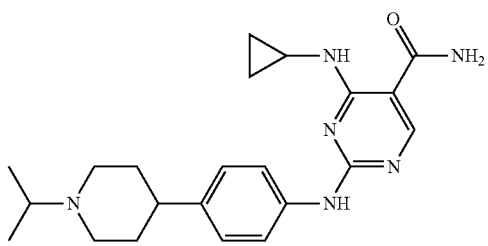 [SMILES: CC(C)N1CCC(c2ccc(Nc3ncc(C(N)=O)c(NC4CC4)n3)cc2)CC1]

4-(Cyclopropylamino)-2-((4-(piperidin-4-yl)phenyl)amino)pyrimidine-5-carboxamide (120 mg, 0.23 mmol) was dissolved in the mixture of 5 mL DCE, 5 mL dioxane and DIEA (200 μL, 1.15 mmol). To the stirred solution was added acetone (170 μL, 2.3 mmol), and the mixture was stirred for 1 h. Then acetic acid (300 μL) and NaBH(OAc)$_3$ (245 mg, 1.15 mmol) were added. The mixture was stirred overnight. The reaction was then quenched with water, concentrated in vacuo to dryness, dissolved in methanol, and subjected to reverse-phase prep HPLC to isolate the title compound. MS found for $C_{22}H_{30}N_6O$ as $(M+H)^+=395.3$. UV: λ=273 nm.

Example 18: 4-(Cyclopropylamino)-2-((4-(1-(dimethylcarbamoyl)piperidin-4-yl)phenyl)amino)pyrimidine-5-carboxamide

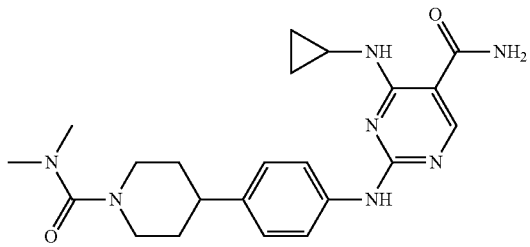 [SMILES: CN(C)C(=O)N1CCC(c2ccc(Nc3ncc(C(N)=O)c(NC4CC4)n3)cc2)CC1]

4-(Cyclopropylamino)-2-((4-(piperidin-4-yl)phenyl) amino)pyrimidine-5-carboxamide (32 mg, 0.08 mmol) was dissolved in 3 mL DMSO. To the mixture were added DIEA (56 µL, 0.32 mmol) and then dimethylcarbamylchloride (15 µL, 0.16 mmol). The mixture was stirred at room temperature for 15 min, quenched with water, acidified with TFA and subjected to reverse-phase prep HPLC to isolate the title compound. MS found for $C_{22}H_{29}N_7O_2$ as $(M+H)^+$ M+H=424.3. UV: $\lambda$=273 nm.

Example 19: 4-(Cyclopropylamino)-2-((4-(1-(morpholine-4-carbonyl)piperidin-4-yl)phenyl)amino) pyrimidine-5-carboxamide

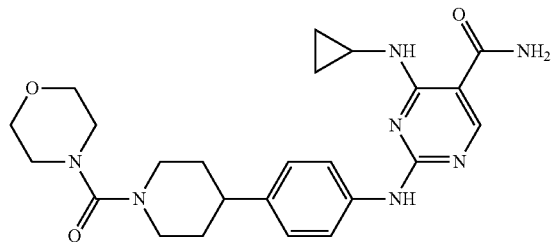 [SMILES: NC(=O)c1cnc(Nc2ccc(C3CCN(C(=O)N4CCOCC4)CC3)cc2)nc1NC1CC1]

The title compound was synthesized in a manner similar to that described in Example 18 (i.e., 4-(cyclopropylamino)-2-((4-(1-(dimethylcarbamoyl)piperidin-4-yl)phenyl)amino) pyrimidine-5-carboxamide), but using morpholine-4-carbonyl chloride. MS found for $C_{24}H_{31}N_7O_3$ as $(M+H)^+$=466.4. UV: $\lambda$=273 nm.

Example 20: 4-(Cyclopropylamino)-2-((4-(1-propionylpiperidin-4-yl)phenyl amino)pyrimidine-5-carboxamide

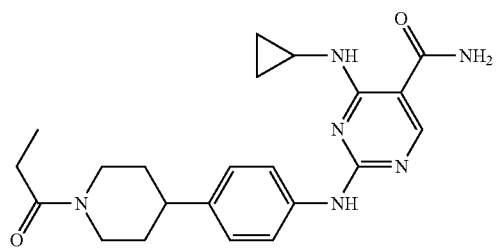 [SMILES: CCC(=O)N1CCC(c2ccc(Nc3ncc(C(N)=O)c(NC4CC4)n3)cc2)CC1]

4-(Cyclopropylamino)-2-((4-(piperidin-4-yl)phenyl) amino)pyrimidine-5-carboxamide (70 mg, 0.18 mmol) was dissolved in 6 mL DMSO. To the mixture were added DIEA (160 µL, 0.90 mmol) and then propionyl chloride (47 µL, 0.54 mmol). The mixture was stirred at room temperature for 1 h. quenched with water, acidified with TFA and subjected to reverse-phase prep HPLC to isolate the title compound. MS found for $C_{22}H_{28}N_6O_2$ as $(M+H)^+$ M=H=409.3. UV: $\lambda$=273 nm.

Example 21: 2-((4-(1-Cyclopentylpiperidin-4-yl) phenyl)amino)-4-(cyclopropylamino)pyrimidine-5-carboxamide

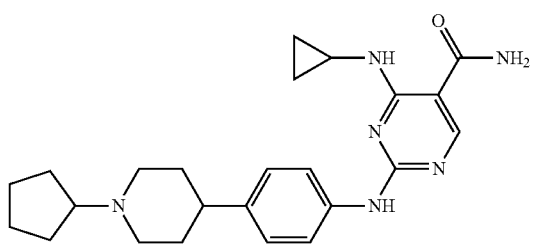 [SMILES: NC(=O)c1cnc(Nc2ccc(C3CCN(C4CCCC4)CC3)cc2)nc1NC1CC1]

The title compound was synthesized in a manner similar to that described in Example 17 (i.e., 4-(cyclopropylamino)-2-((4-(1-isopropylpiperidin-4-yl)phenyl)amino)pyrimidine-5-carboxamide), but using cyclopentanone. MS found for $C_{24}H_{32}N_6O$ as $(M+H)^+$=421.4. UV: $\lambda$=273 nm.

Example 22: 4-(Cyclopropylamino)-2-(4-(4-(ethylsulfonyl)piperazin-1-yl)-3-methoxyphenylamino) pyrimidine-5-carboxamide

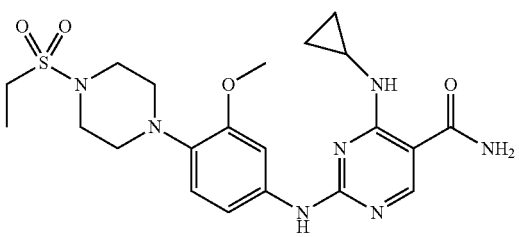 [SMILES: CCS(=O)(=O)N1CCN(c2ccc(Nc3ncc(C(N)=O)c(NC4CC4)n3)cc2OC)CC1]

The title compound was synthesized with 4-(4-(ethylsulfonyl)piperazin-1-yl)-3-methoxyaniline in a manner similar to that described in Scheme 1. MS found for $C_{21}H_{29}N_7O_4S$ as $(M+H)^+$=MS 476.4; UV 202.2, 265.7 nm.

Example 23: Methyl 4-(4-((5-Carbamoyl-4-(cyclopropylamino)pyrimidin-2-yl)amino)phenyl)piperidine-1-carboxylate

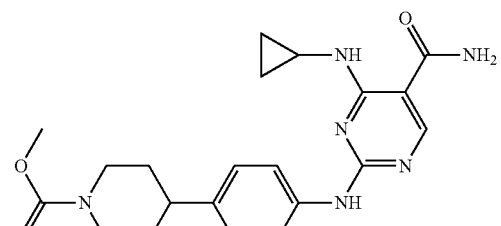

The title compound was synthesized in a manner similar to that described in Example 18 (i.e., 4-(cyclopropylamino)-2-((4-(1-(dimethylcarbamoyl)piperidin-4-yl)phenyl)amino) pyrimidine-5-carboxamide), but using methyl chloroformate. MS found for $C_{21}H_{26}N_6O_3$ as $(M+H)^+$=411.3. UV: $\lambda$=273 nm.

Example 24: Ethyl 4-(4-((5-Carbamoyl-4-(cyclopropylamino)pyrimidin-2-yl amino)phenyl)piperidine-1-carboxylate

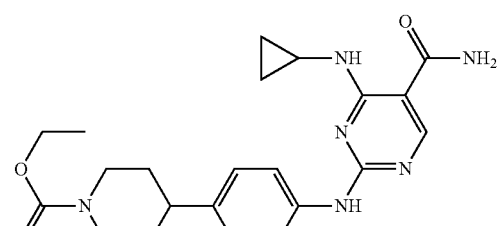

The title compound was synthesized in a manner similar to that described in Example 18 (i.e., 4-(cyclopropylamino)-2-((4-(1-(dimethylcarbamoyl)piperidin-4-yl)phenyl)amino) pyrimidine-5-carboxamide), but using ethyl chloroformate. MS found for $C_{22}H_{28}N_6O_3$ as $(M+H)^+$=425.3. UV: $\lambda$=273 nm.

Example 25: 4-(Cyclopropylamino)-2-((4-(1-(N,N-dimethylsulfamoyl)piperidin-4-yl)phenyl)amino)pyrimidine-5-carboxamide

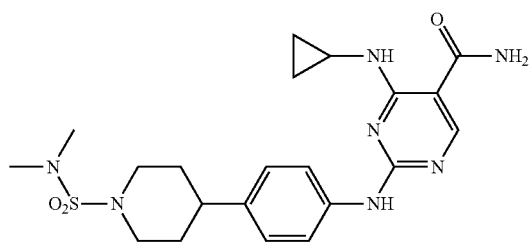

The title compound was synthesized in a manner similar to that described in Example 18 (i.e., 4-(cyclopropylamino)-2-((4-(1-(dimethylcarbamoyl)piperidin-4-yl)phenyl)amino)pyrimidine-5-carboxamide), but using dimethylsulfamoyl chloride. MS found for $C_{21}H_{29}N_7O_3S$ as $(M+H)^+=460.3$. UV: $\lambda=278$ nm.

Example 26: 4-(Cyclopropylamino)-2-((4-(1-(pyrrolidine-1-carbonyl)piperidin-4-yl)phenyl)amino)pyrimidine-5-carboxamide

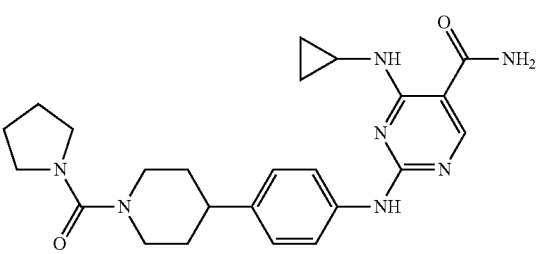 [SMILES: NC(=O)c1cnc(Nc2ccc(C3CCN(C(=O)N4CCCC4)CC3)cc2)nc1NC1CC1]

The title compound was synthesized in a manner similar to that described in Example 18 (i.e., 4-(cyclopropylamino)-2-((4-(1-(dimethylcarbamoyl)piperidin-4-yl)phenyl)amino)pyrimidine-5-carboxamide), but using 1-pyrrolidinecarbonyl chloride. MS found for $C_{24}H_{31}N_7O_2$ as $(M+H)^+=450.4$. UV: $\lambda=273$ nm.

Example 27: 4-(Cyclopropylamino)-2-((4-(1-(tetrahydro-2H-pyran-4-yl)piperidin-4-yl)phenyl)amino)pyrimidine-5-carboxamide

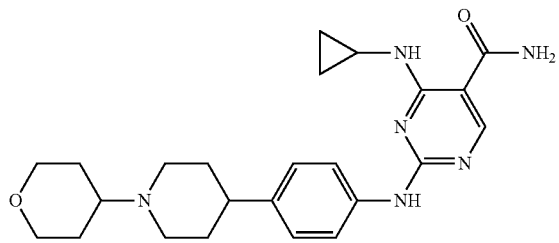 [SMILES: NC(=O)c1cnc(Nc2ccc(C3CCN(C4CCOCC4)CC3)cc2)nc1NC1CC1]

The title compound was synthesized in a manner similar to that described in Example 17 (i.e., 4-(cyclopropylamino)-2-((4-(1-isopropylpiperidin-4-yl)phenyl)amino)pyrimidine-5-carboxamide), but using tetrahydro-4H-pyran-4-one. MS found for $C?_4H?_2N_6O_2$ as $(M+H)^+=437.4$. UV: $\lambda=273$ nm.

Example 28: 4-(Cyclopropylamino)-2-(5-(4-(ethylsulfonyl)piperazin-1-yl)pyridin-2-ylamino)pyrimidine-5-carboxamide

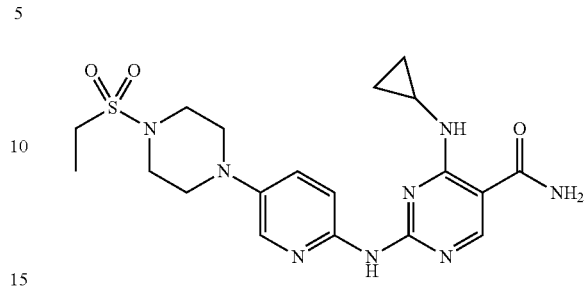

The title compound was synthesized with 5-(4-(ethylsulfonyl)piperazin-1-yl)pyridin-2-amine in a manner similar to that described in Scheme 1. MS found for $C_{19}H_{26}N_8O_3S$ as $(M+H)^+=MS$ 447.3; UV 275.5 nm.

Example 29: 4-(Cyclopropylamino)-2-(4-(4-(ethylsulfonyl)piperazin-1-yl)-3-methylphenylamino)pyrimidine-5-carboxamide

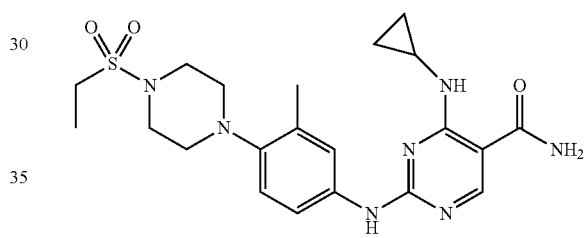

The title compound was synthesized in a manner similar to that described in Scheme 1 using an aniline prepared from 4-fluoro-3-methylnitrobenzene by a method similar to that described previously. MS found for $C_{21}H_{29}N_7O_3S$ as $(M+H)^+=460.4$.

Example 30: 2-(3-Cyano-4-(4-(methylsulfonyl)piperazin-1-yl)phenylamino)-4-(cyclopropylamino)pyrimidine-5-carboxamide

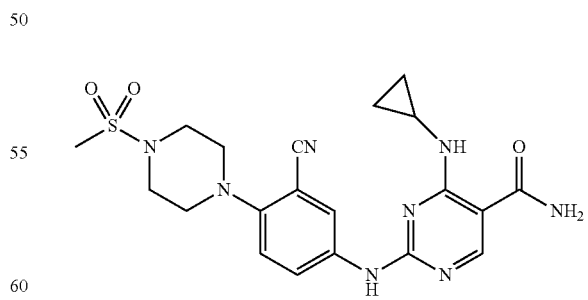

The title compound was synthesized in a manner similar to that described in Scheme 1, using an aniline prepared from 2-fluoro-5-nitrobenzonitrile and Boc-protected piperazine in a manner similar to that described above. MS found for $C_{20}H_{24}N_8O_3S$ as $(M+H)^+=457.3$. UV: $\lambda=222$, 293 nm.

Example 31: 2-(3-Cyano-4-(4-(ethylsulfonyl)piper-azin-1-yl)phenylamino)-4-(cyclopropylamino)py-rimidine-5-carboxamide

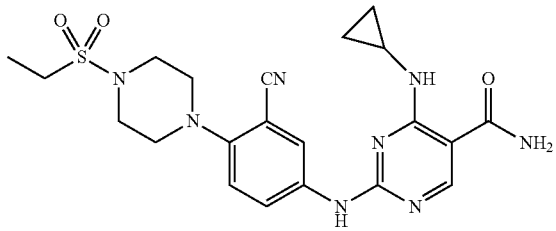 [SMILES: CCS(=O)(=O)N1CCN(c2ccc(Nc3ncc(C(N)=O)c(NC4CC4)n3)cc2C#N)CC1]

The title compound was synthesized in a manner similar to that described in Scheme 1 using a procedure and reagents similar to that described above. MS found for $C_{21}H_{26}N_8O_3S$ as M+H)$^+$=471.3. UV: λ=222, 293 nm.

Example 32: 4-(Cyclopropylamino)-2-((4-(1-ethyl-piperidin-4-yl)phenyl)amino)pyrimidine-5-carbox-amide

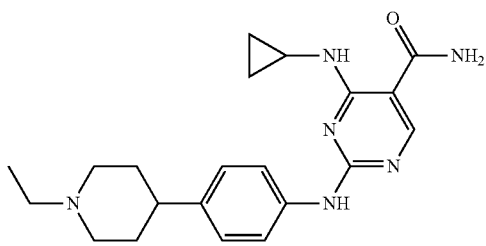

The title compound was synthesized in a manner similar to that described in Example 17 (i.e., 4-(cyclopropylamino)-2-((4-(1-isopropylpiperidin-4-yl)phenyl)amino)pyrimidine-5-carboxamide), but using acetaldehyde. MS found for $C_{21}H_{28}N_6O$ as (M+H)$^+$=381.3. UV: λ=268 nm.

Example 33: 4-(Cyclopropylamino)-2-((4-ethylphe-nyl)amino)pyrimidine-5-carboxamide

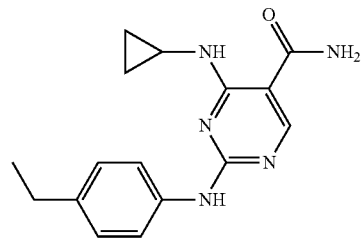 [SMILES: CCc1ccc(Nc2ncc(C(N)=O)c(NC3CC3)n2)cc1]

The title compound was synthesized with 4-ethylaniline in a manner similar to that described in Scheme 1. MS found for $C_{16}H_{19}N_5O$ as (M+H)$^+$=298.4. UV: λ=273 nm.

Example 34: 4-(Cyclopropylamino)-2-((4-isopropyl-phenyl)amino)pyrimidine-5-carboxamide

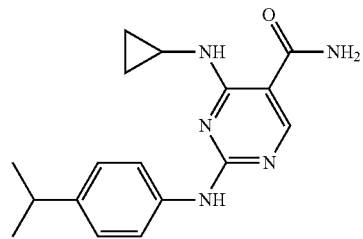 [SMILES: CC(C)c1ccc(Nc2ncc(C(N)=O)c(NC3CC3)n2)cc1]

The title compound was synthesized with 4-isopropylaniline in a manner similar to that described in Scheme 1. MS found for $C_{17}H_{21}N_5O$ as (M+H)$^+$=312.3. UV: λ=273 nm.

Example 35: 4-(Cyclopropylamino)-2-(3,5-difluoro-4-(4-(methylsulfonyl)piperazin-1-yl)phenylamino)pyrimidine-5-carboxamide

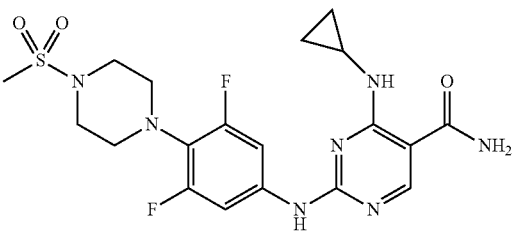 [SMILES: CS(=O)(=O)N1CCN(c2c(F)cc(Nc3ncc(C(N)=O)c(NC4CC4)n3)cc2F)CC1]

The title compound was synthesized in a manner similar to that described in Scheme 1, using an aniline prepared from 3,4,5-trifluoronitrobenzene with a method similar to that described above. MS found for $C_{19}H_{23}F_2N_7O_3S$ as (M+H)$^+$=468.3. UV: λ=207, 278, 295.

Example 36: 4-(Cyclopropylamino)-2-(4-(4-(ethyl-sulfonyl)piperazin-1-yl)-3,5-difluorophenylamino)pyrimidine-5-carboxamide

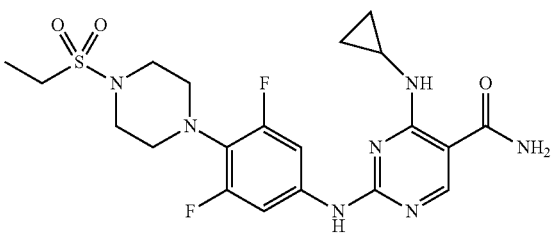 [SMILES: CCS(=O)(=O)N1CCN(c2c(F)cc(Nc3ncc(C(N)=O)c(NC4CC4)n3)cc2F)CC1]

The title compound was synthesized in a manner similar to that described in Scheme 1 using an aniline similar to that described previously. MS found for $C_{20}H_{25}F_2N_7O_3S$ as (M+H)$^+$=482.3. UV: λ=204, 293.

Example 37: 6-(Cyclopropylamino)-4-((4-(piperi-din-4-yl)phenyl)amino)nicotinamide

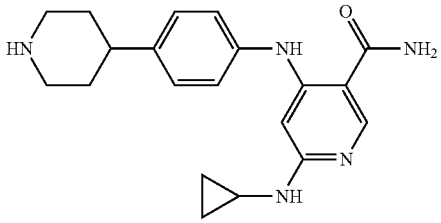 [SMILES: NC(=O)c1cnc(NC2CC2)cc1Nc1ccc(C2CCNCC2)cc1]

The mixture of 4,6-dichloronicotinitrile (2.00 g, 11.56 mmol), cyclopropylamine (1.60 mL, 23.12 mmol), and DIEA (4.02 mL, 23.12 mmol) in 30 mL NMP was stirred in a sealed tube at 80° C. for 2.5 h and poured into water. The solid was isolated by filtration, washed with water and dried in vacuum oven to afford a mixture of 4-chloro-6-(cyclo-propylamino)nicotinonitrile and 6-chloro-4-(cyclopropy-lamino)nicotinonitrile (1.81 g). This mixture (500 mg, 2.6 mmol) was dissolved in 40 mL dioxane. To this solution were added tert-butyl 4-(4-aminophenyl)piperidine-1-car-boxylate (1.44 g, 5.2 mmol), cesium carbonate (2.54 g, 7.8 mmol), BINAP (325 mg, 0.52 mmol), and Pd(OAc)$_2$ (120 mg, 0.52 mmol). The mixture was degassed with an argon stream and stirred under argon at 105° C. overnight. The mixture was cooled and diluted with EtOAc, filtered through Celite, concentrated in vacuo and subjected to flash column chromatography with 10%-40% ethyl acetate in hexanes to isolate tert-butyl 4-(4-((5-cyano-4-(cyclopropylamino)pyridin-2-yl)amino)phenyl)piperidine-1-carboxylate and tert-butyl 4-(4-((5-cyano-2-(cyclopropylamino)pyridin-4-yl)amino)phenyl)piperidine-1-carboxylate.

Tert-butyl 4-(4-((5-cyano-2-(cyclopropylamino)pyridin-4-yl)amino)phenyl)piperidine-1-carboxylate was treated with 6 mL TFA and 1 mL conc. H$_2$SO$_4$ at 80° C. for 1 h. The messy mixture was cooled to room temperature, diluted with water and subjected to reverse-phase prep HPLC to isolate the title compound. MS found for C$_{20}$H$_{25}$N$_5$O as (M+H)$^+$=352.3. UV: λ=263 nm.

Example 38: 4-(Cyclopropylamino)-2-(4-(4-(vinylsulfonyl)piperazin-1-yl)phenylamino)pyrimidine-5-carboxamide

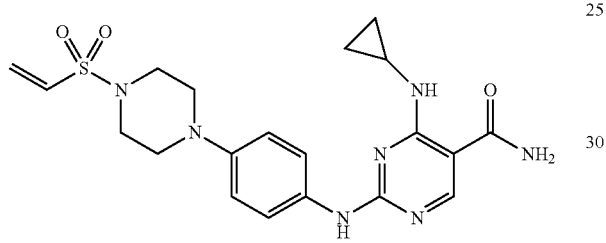

The title compound was synthesized in a manner similar to that described in Scheme 1, using an aniline prepared from 2-chloroethylsulfonyl chloride. The chloroethyl moiety eliminated to form the desired material upon a basic workup. MS found for C$_{20}$H$_{25}$N$_7$O$_3$S as (M+H)$^+$=444.5. UV: λ=229, 288.

Example 39: 4-(Cyclopropylamino)-2-((4-(1-phenylpiperidin-4-yl)phenyl)amino)pyrimidine-5-carboxamide

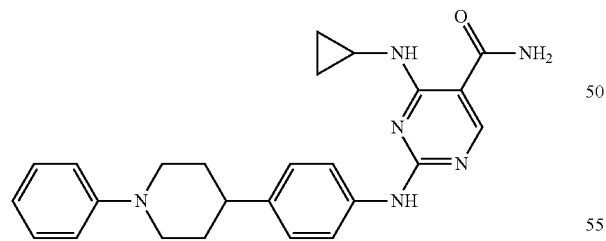

The mixture of 4-(cyclopropylamino)-2-((4-(piperidin-4-yl)phenyl)amino)pyrimidine-5-carboxamide (100 mg, 0.19 mmol), phenylboronic acid (240 mg, 1.9 mmol) and Cu(OAc)$_2$ (182 mg, 1.0 mmol) in 1 mL pyridine and 5 mL DCM was stirred at room temperature for 5 days. The mixture was diluted with EtOAc and washed with brine three times. It was dried, concentrated in vacuo and subjected to reverse-phase prep HPLC to isolate the title compound. MS found for C$_{25}$H$_{28}$N$_6$O as (M+H)$^+$=429.3. UV: λ=273 nm.

Example 40: 4-(Cyclopropylamino)-2-((4-(1-(pyridin-3-yl)piperidin-4-yl)phenyl)amino)pyrimidine-5-carboxamide

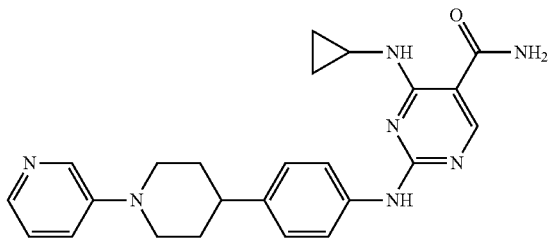 [SMILES: NC(=O)c1cnc(Nc2ccc(C3CCN(c4cccnc4)CC3)cc2)nc1NC1CC1]

The title compound was synthesized in a manner similar to that described in Example 39 (i.e., 4-(cyclopropylamino)-2-((4-(1-phenylpiperidin-4-yl)phenyl)amino)pyrimidine-5-carboxamide), but using pyridine-3-boronic acid. MS found for C$_{24}$H$_{27}$N$_7$O as (M+H)$^+$=430.3. UV: λ=273 nm.

Example 41: 4-(Cyclopropylamino)-6-((4-(piperidin-4-yl)phenyl)amino)nicotinamide

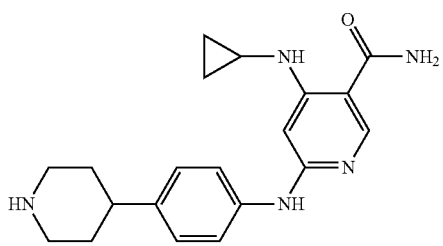 [SMILES: NC(=O)c1cnc(Nc2ccc(C3CCNCC3)cc2)cc1NC1CC1]

The compound tert-butyl 4-(4-((5-cyano-4-(cyclopropylamino)pyridin-2-yl)amino)phenyl)piperidine-1-carboxylate was treated with TFA at room temperature (see, e.g., the method of Example 37 for 6-(cyclopropylamino)-4-((4-(piperidin-4-yl)phenyl)amino)nicotinamide). The reaction mixture was diluted with water, filtered and subjected to reverse-phase prep HPLC to isolate the title compound. MS found for C$_{20}$H$_{25}$N$_5$O as (M+H)$^+$=352.3. UV: λ=259 nm.

Example 42: 4-(Cyclopropylamino)-2-((4-fluorophenyl)amino)pyrimidine-5-carboxamide

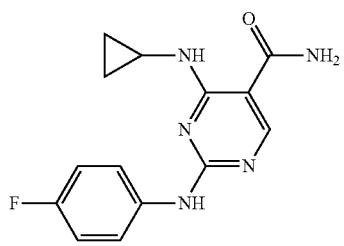 [SMILES: NC(=O)c1cnc(Nc2ccc(F)cc2)nc1NC1CC1]

The title compound was synthesized with 4-fluoroaniline in a manner similar to that described in Scheme 1. MS found for C$_{14}$H$_{14}$FN$_5$O as (M+H)$^+$=288.2. UV: λ=263 nm.

Example 43: 4-(Cyclopropylamino)-6-((4-(1-(ethyl-sulfonyl)piperidin-4-yl)phenyl)amino)nicotinamide

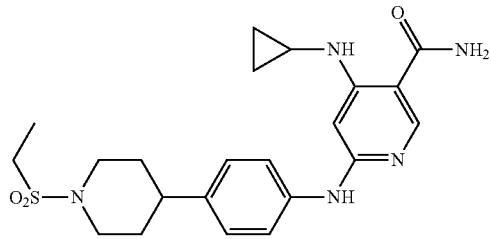 [SMILES: CCS(=O)(=O)N1CCC(c2ccc(Nc3cc(NC4CC4)c(C(N)=O)cn3)cc2)CC1]

4-(Cyclopropylamino)-6-((4-(piperidin-4-yl)phenyl) amino)nicotinamide (70 mg, 0.18 mmol) was dissolved in 4 mL DMSO. To the mixture were added DIEA (94 μL, 0.54 mmol) and ethanesulfonyl chloride (52 μL, 0.54 mmol), and the mixture was stirred at room temperature for 30 min. It was diluted with water, acidified with TFA, filtered and subjected to reverse-phase prep HPLC to isolate the title compound. MS found for $C_{22}H_{29}N_5O_3S$ as $(M+H)^+=444.3$. UV: $\lambda=259$ nm.

Example 44: 4-(Cyclopropylamino)-2-((4-(1-(pyridin-2-yl)piperidin-4-yl)phenyl)amino)pyrimidine-5-carboxamide

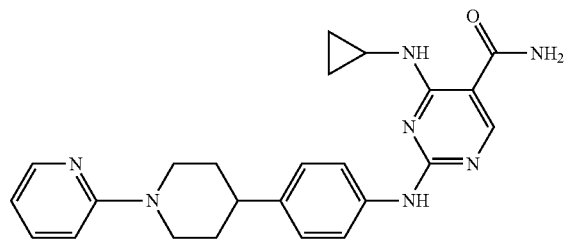 [SMILES: NC(=O)c1cnc(Nc2ccc(C3CCN(c4ccccn4)CC3)cc2)nc1NC1CC1]

4-(Cyclopropylamino)-2-((4-(piperidin-4-yl)phenyl) amino)pyrimidine-5-carboxamide (90 mg, 0.23 mmol) was dissolved in 2 mL NMP. To the mixture were added DIEA (200 μL, 1.15 mmol) and 2-fluoropyridine (200 μL, 2.30 mmol). The mixture was stirred in a sealed tube at 125° C. overnight. It was acidified with TFA and subjected to reverse-phase prep HPLC to isolate the title compound. MS found for $C_{24}H_{27}N_7O$ as $(M+H)^+=430.3$. UV: $\lambda=249$ nm.

Example 45: 4-(Cyclopropylamino)-2-((4-(1-(3-fluoropyridin-2-yl)piperidin-4-yl)phenyl)amino) pyrimidine-5-carboxamide

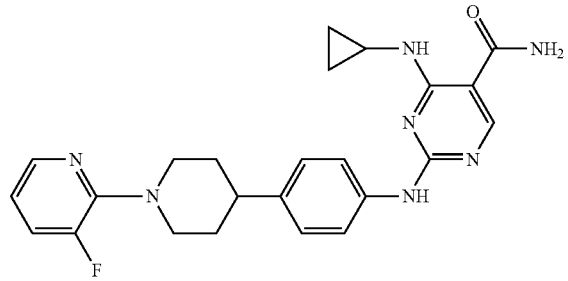 [SMILES: NC(=O)c1cnc(Nc2ccc(C3CCN(c4ncccc4F)CC3)cc2)nc1NC1CC1]

4-(Cyclopropylamino)-2-((4-(piperidin-4-yl)phenyl) amino)pyrimidine-5-carboxamide (90 mg, 0.23 mmol) was dissolved in 2 mL NMP. To the mixture were added DIEA (200 μL, 1.15 mmol) and 2,3-difluoropyridine (265 mg, 2.30 mmol). The mixture was stirred in a sealed tube at 125° C. overnight. It was acidified with TFA and subjected to reverse-phase prep HPLC to isolate the title compound. MS found for $C_{24}H_{26}FN_7O$ as $(M+H)^+=448.3$. UV: $\lambda=254$ nm.

Example 46: 2-((4-(1-Cyclobutylpiperidin-4-yl)phenyl)amino)-4-(cyclopropylamino)pyrimidine-5-carboxamide

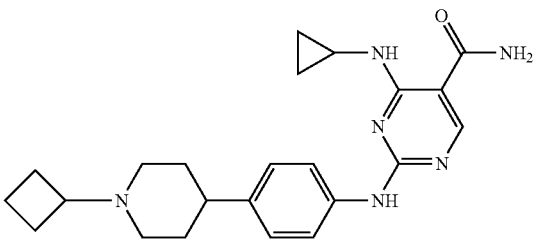 [SMILES: NC(=O)c1cnc(Nc2ccc(C3CCN(C4CCC4)CC3)cc2)nc1NC1CC1]

The title compound was synthesized in a manner similar to that described in Example 17 (i.e., 4-(cyclopropylamino)-2-((4-(1-isopropylpiperidin-4-yl)phenyl)amino)pyrimidine-5-carboxamide), but using cyclobutanone. MS found for $C_{23}H_{30}N_6O$ as $(M+H)^+=407.3$. UV: $\lambda=273$ nm.

Example 47: 4-(Cyclopropylamino)-2-((4-(1-(oxetan-3-yl)piperidin-4-yl)phenyl)amino)pyrimidine-5-carboxamide

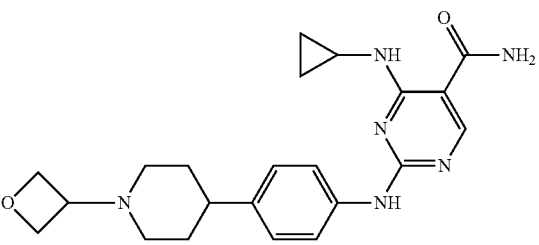 [SMILES: NC(=O)c1cnc(Nc2ccc(C3CCN(C4COC4)CC3)cc2)nc1NC1CC1]

The title compound was synthesized in a manner similar to that described in Example 17 (i.e., 4-(cyclopropylamino)-2-((4-(1-isopropylpiperidin-4-yl)phenyl)amino)pyrimidine-5-carboxamide), but using 3-oxetanone. MS found for $C_{22}H_{28}N_6O_2$ as $(M+H)^+=409.3$. UV: $\lambda=273$ nm.

Example 48: 2-((4-(1-Cyclohexylpiperidin-4-yl) phenyl)amino)-4-(cyclopropylamino)pyrimidine-5-carboxamide

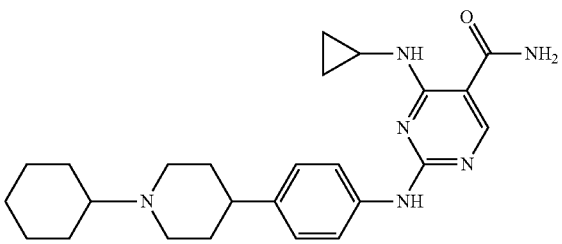 [SMILES: NC(=O)c1cnc(Nc2ccc(C3CCN(C4CCCCC4)CC3)cc2)nc1NC1CC1]

The title compound was synthesized in a manner similar to that described in Example 17 (i.e., 4-(cyclopropylamino)-2-((4-(1-isopropylpiperidin-4-yl)phenyl)amino)pyrimidine-5-carboxamide), but using cyclohexanone. MS found for $C_{25}H_{34}N_6O$ as $(M+H)^+=435.4$. UV: $\lambda=273$ nm.

Example 49: 4-(Cyclopropylamino)-2-((4-(1-(2,2,2-trifluoroethyl)piperidin-4-yl)phenyl)amino)pyrimidine-5-carboxamide

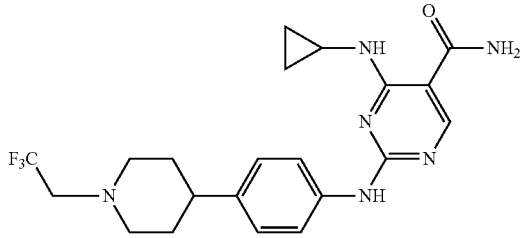 [SMILES: NC(=O)c1cnc(Nc2ccc(C3CCN(CC(F)(F)F)CC3)cc2)nc1NC1CC1]

4-(Cyclopropylamino)-2-((4-(piperidin-4-yl)phenyl)amino)pyrimidine-5-carboxamide (50 mg, 0.13 mmol) was dissolved in 2 mL NMP. To the mixture were added DIEA (90 μL, 0.52 mmol) and 2,2,2-trifluoroiodoethane (0.5 mL). The mixture was stirred in a sealed tube at 80° C. for 2 days. It was concentrated in vacuo, acidified with TFA and subjected to reverse-phase prep HPLC to isolate the title compound. MS found for $C_{21}H_{25}F_3N_6$ as $(M+H)^+=435.5$. UV: $\lambda=273$ nm.

Example 50: 4-(Cyclopropylamino)-2-((4-cyclopropylphenyl)amino)pyrimidine-5-carboxamide

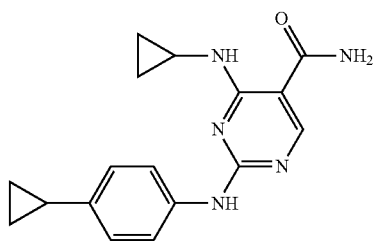 [SMILES: NC(=O)c1cnc(Nc2ccc(C3CC3)cc2)nc1NC1CC1]

The title compound was synthesized with 4-cyclopropylaniline in a manner similar to that described in Scheme 1. MS found for $C_{17}H_{19}N_5O$ as $(M+H)^+=310.3$. UV: $\lambda=280$ nm.

Example 51: 4-(Cyclopropylamino)-2-((4-(1-(pentan-3-yl)piperidin-4-yl)phenyl amino)pyrimidine-5-carboxamide

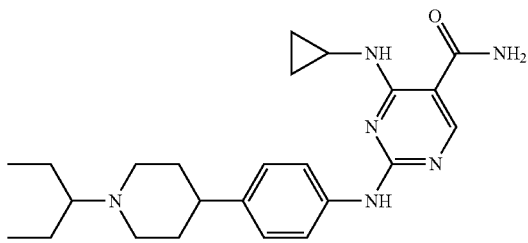 [SMILES: CCC(CC)N1CCC(c2ccc(Nc3ncc(C(N)=O)c(NC4CC4)n3)cc2)CC1]

The title compound was synthesized in a manner similar to that described in Example 17 (i.e., 4-(cyclopropylamino)-2-((4-(1-isopropylpiperidin-4-yl)phenyl)amino)pyrimidine-5-carboxamide), but using 3-pentanone. MS found for $C_{24}H_{34}N_6O$ as $(M+H)^+=423.4$. UV: $\lambda=273$ nm.

Example 52: 2-((4-(1-(2-Cyanoacetyl)piperidin-4-yl)phenyl)amino)-4-(cyclopropylamino)pyrimidine-5-carboxamide

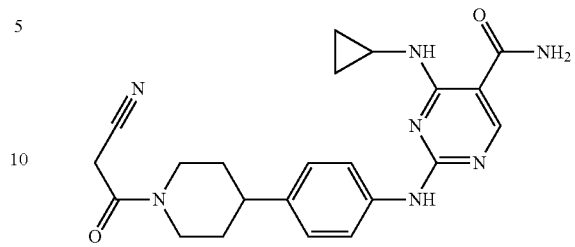

4-(Cyclopropylamino)-2-((4-(piperidin-4-yl)phenyl)amino)pyrimidine-5-carboxamide (60 mg, 0.15 mmol) was dissolved in 3 mL DMF. To the mixture were added cyanoacetic acid (64 mg, 0.75 mmol). DIEA (260 μL, 1.5 mmol) and then BOP (284 mg, 0.75 mmol). The mixture was stirred at room temperature for 2 h and quenched with TFA. It was diluted with water and subjected to reverse-phase prep HPLC to isolate the title compound. MS found for $C_{22}H_{25}N_7O_2$ as $(M+H)^+$ M+H=420.3. UV: $\lambda=272$ nm.

Example 53: 4-(Cyclopropylamino)-2-((4-(1-(tetrahydro-2H-pyran-4-carbonyl)piperidin-4-yl)phenyl)amino)pyrimidine-5-carboxamide

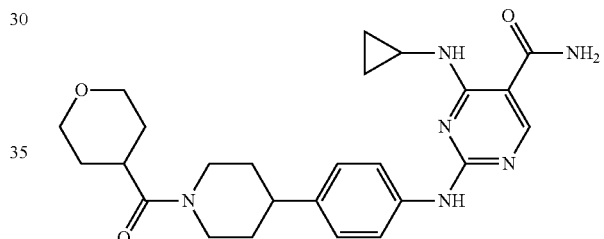

The title compound was synthesized in a manner similar to that described in Example 52 (i.e., 2-((4-(1-(2-cyanoacetyl)piperidin-4-yl)phenyl)amino)-4-(cyclopropylamino)pyrimidine-5-carboxamide), but using tetrahydropyran-4-carboxylic acid. MS found for $C_{25}H_{32}N_6O_3$ as $(M+H)^+=465.4$. UV: $\lambda=273$ nm.

Example 54: 4-(Cyclopropylamino)-2-((4-(trifluoromethyl)phenyl)amino)pyrimidine-5-carboxamide

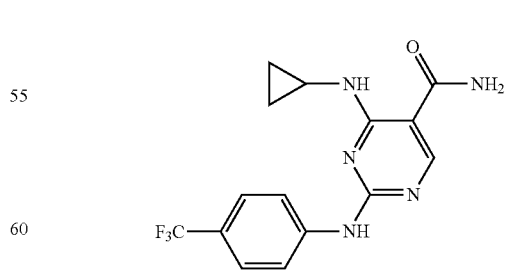

The title compound was synthesized with 4-trifluoromethylaniline in a manner similar to that described in Scheme 1. MS found for $C_{15}H_{14}F_3N_5O$ as $(M+H)^+=338.2$. UV: $\lambda=273$ nm.

Example 55: 4-(Cyclopropylamino)-2-((4-(1-(pyridin-3-ylsulfonyl)piperidin-4-yl)phenyl)amino)pyrimidine-5-carboxamide

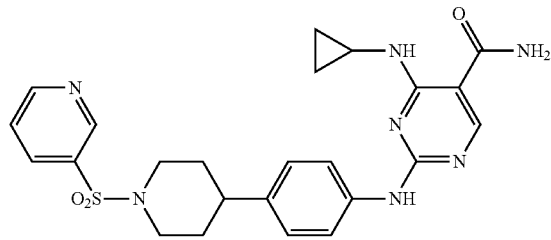 [SMILES: NC(=O)c1cnc(Nc2ccc(C3CCN(S(=O)(=O)c4cccnc4)CC3)cc2)nc1NC1CC1]

The title compound was synthesized in a manner similar to that described in Example 3 (i.e., 4-(cyclopropylamino)-2-((4-(1-(ethylsulfonyl)piperidin-4-yl)phenyl)amino)pyrimidine-5-carboxamide), but using 3-pyridinesulfonyl chloride. MS found for $C_{24}H_{27}N_7O_3S$ as $(M+H)^+=494.4$. UV: $\lambda=268$ nm.

Example 56: 4-(Cyclopropylamino)-2-((4-(1-((1-methyl-1H-imidazol-4-yl)sulfonyl)piperidin-4-yl)phenyl)amino)pyrimidine-5-carboxamide

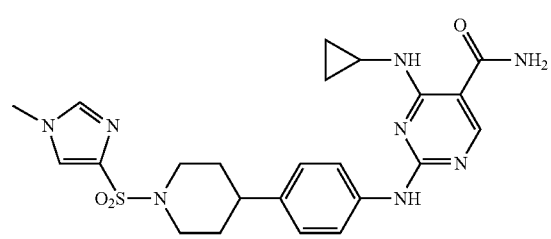 [SMILES: Cn1cnc(S(=O)(=O)N2CCC(c3ccc(Nc4ncc(C(N)=O)c(NC5CC5)n4)cc3)CC2)c1]

The title compound was synthesized in a manner similar to that described in Example 3 (i.e., 4-(cyclopropylamino)-2-((4-(1-(ethylsulfonyl)piperidin-4-yl)phenyl)amino)pyrimidine-5-carboxamide), but using 1-methylimidazole-4-sulfonyl chloride. MS found for $C_{23}H_{28}N_8O_3S$ as $(M+H)^+=497.3$. UV: $\lambda=273$ nm.

Example 57: 4-(Cyclopropylamino)-2-((4-(1-((1-methyl-1H-pyrazol-4-yl)sulfonyl)piperidin-4-yl)phenyl)amino)pyrimidine-5-carboxamide

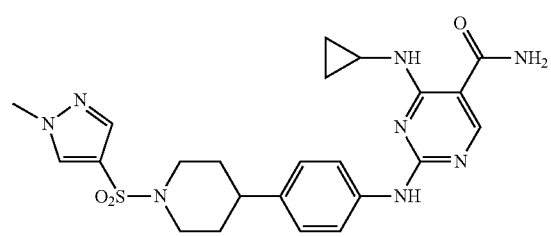 [SMILES: Cn1cc(S(=O)(=O)N2CCC(c3ccc(Nc4ncc(C(N)=O)c(NC5CC5)n4)cc3)CC2)cn1]

The title compound was synthesized in a manner similar to that described in Example 3 (i.e., 4-(cyclopropylamino)-2-((4-(1-(ethylsulfonyl)piperidin-4-yl)phenyl)amino)pyrimidine-5-carboxamide), but using 1-methyl-1H-pyrazole-4-sulfonyl chloride. MS found for $C_{23}H_{28}N_8O_3S$ as $(M+H)^+=497.4$. UV: $\lambda=273$ nm.

Example 58: 4-(Cyclopropylamino)-2-((4-(1-methylpiperidin-4-yl)phenyl)amino)pyrimidine-5-carboxamide

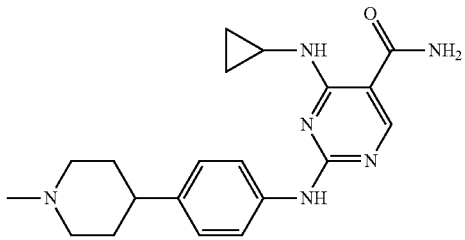 [SMILES: CN1CCC(c2ccc(Nc3ncc(C(N)=O)c(NC4CC4)n3)cc2)CC1]

The title compound was synthesized with 4-(1-methylpiperidin-4-yl)aniline in a manner similar to that described in Scheme 1. MS found for $C_{20}H_{26}N_6O$ as $(M+H)^+=367.4$. UV: $\lambda=268$ nm.

Example 59: 4-(Cyclopropylamino)-2-((4-(1-(2-methoxyacetyl)piperidin-4-yl)phenyl)amino)pyrimidine-5-carboxamide

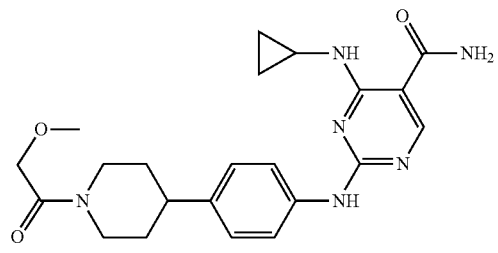 [SMILES: COCC(=O)N1CCC(c2ccc(Nc3ncc(C(N)=O)c(NC4CC4)n3)cc2)CC1]

The title compound was synthesized in a manner similar to that described in Example 18 (i.e., 4-(cyclopropylamino)-2-((4-(1-(dimethylcarbamoyl)piperidin-4-yl)phenyl)amino)pyrimidine-5-carboxamide), but using methoxyacetyl chloride. MS found for $C_{22}H_{28}N_6O_3$ as $(M+H)^+=425.4$. UV: $\lambda=273$ nm.

Example 60: 2-((4-(1-(Cyclopropanecarbonyl)piperidin-4-yl)phenyl)amino)-4-(cyclopropylamino)pyrimidine-5-carboxamide

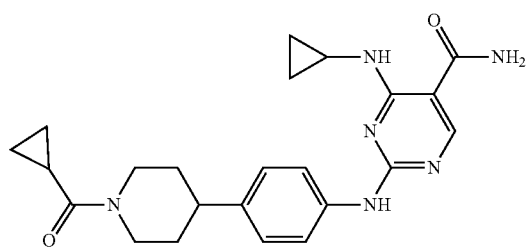 [SMILES: NC(=O)c1cnc(Nc2ccc(C3CCN(C(=O)C4CC4)CC3)cc2)nc1NC1CC1]

The title compound was synthesized in a manner similar to that described in Example 52 (i.e., 2-((4-(1-(2-cyanoacetyl)piperidin-4-yl)phenyl)amino)-4-(cyclopropylamino)pyrimidine-5-carboxamide), but using cyclopropylcarboxylic acid. MS found for $C_{23}H_{28}N_6O_2$ as $(M+H)^+=421.4$. UV: $\lambda=273$ nm.

Example 61: 4-(Cyclopropylamino)-2-((4-(1-nicotinoylpiperidin-4-yl)phenyl)amino)pyrimidine-5-carboxamide

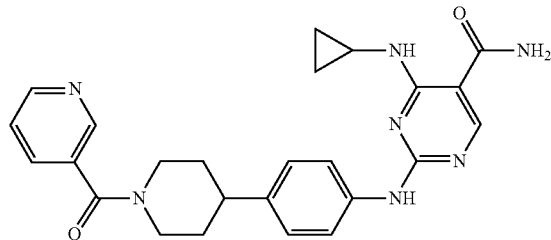 [SMILES: NC(=O)c1cnc(Nc2ccc(C3CCN(C(=O)c4cccnc4)CC3)cc2)nc1NC1CC1]

The title compound was synthesized in a manner similar to that described in Example 52 (i.e., 2-((4-(1-(2-cyanoacetyl)piperidin-4-yl)phenyl)amino)-4-(cyclopropylamino)pyrimidine-5-carboxamide), but using nicotinic acid. MS found for $C_{25}H_{27}N_7O_2$ as $(M+H)^+$=458.4. UV: $\lambda$=268 nm.

Example 62: 2-((4-(1'-Cyclopropyl-[1,4'-bipiperidin]-4-yl)phenyl)amino)-4-(cyclopropylamino)pyrimidine-5-carboxamide

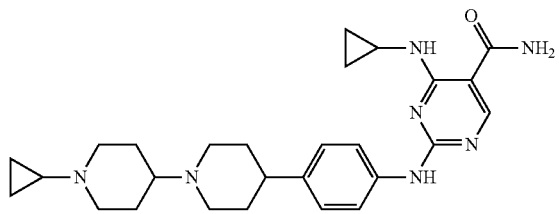 [SMILES: NC(=O)c1cnc(Nc2ccc(C3CCN(C4CCN(C5CC5)CC4)CC3)cc2)nc1NC1CC1]

The title compound was synthesized in a manner similar to that described in Example 17 (i.e., 4-(cyclopropylamino)-2-((4-(1-isopropylpiperidin-4-yl)phenyl)amino)pyrimidine-5-carboxamide), but using 1-cyclopropyl-4-piperidone. MS found for $C_{27}H_{37}N_7O$ as $(M+H)^+$=476.5. UV: $\lambda$=273 nm.

Example 63: 2-((4-(1'-Cyclopropyl-[1,4'-bipiperidin]-4-yl)phenyl)amino)-4-(cyclopropylamino)pyrimidine-5-carboxamide

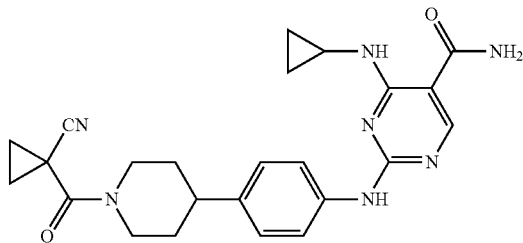 [SMILES: N#CC1(C(=O)N2CCC(c3ccc(Nc4ncc(C(N)=O)c(NC5CC5)n4)cc3)CC2)CC1]

The title compound was synthesized in a manner similar to that described in Example 52 (i.e., 2-((4-(1-(2-cyanoacetyl)piperidin-4-yl)phenyl)amino)-4-(cyclopropylamino)pyrimidine-5-carboxamide), but using 1-cyanocyclopropanecarboxylic acid. MS found for $C_{24}H_{27}N_7O_2$ as $(M+H)^+$=446.4. UV: $\lambda$=273 nm.

Example 64: 2-((4-(1-(Cyanomethyl)piperidin-4-yl)phenyl)amino)-4-(cyclopropylamino)pyrimidine-5-carboxamide

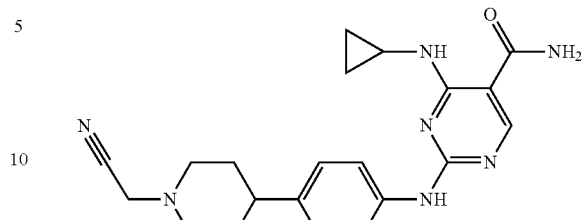

4-(Cyclopropylamino)-2-((4-(piperidin-4-yl)phenyl)amino)pyrimidine-5-carboxamide (150 mg, 0.38 mmol) was dissolved in 4 mL NMP. To the mixture were added DIEA (200 µL, 1.14 mmol) and then bromoacetonitrile (51 µL, 0.76 mmol). The mixture was stirred at room temperature for 2 h and quenched with TFA. It was diluted with water and subjected to reverse-phase prep HPLC to isolate the title compound. MS found for $C_{21}H_{25}N_7O$ as $(M+H)^+$=392.3. UV: $\lambda$=268 nm.

Example 65: 4-(Cyclopropylamino)-2-((4-(1-(2,2-difluoroethyl)piperidin-4-yl)phenyl)amino)pyrimidine-5-carboxamide

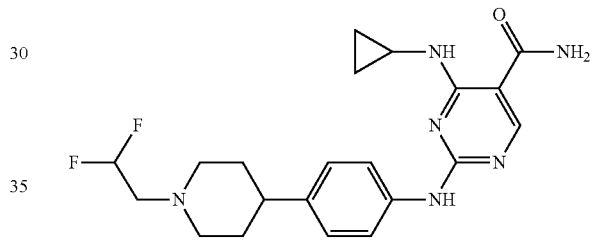

4-(Cyclopropylamino)-2-((4-(piperidin-4-yl)phenyl)amino)pyrimidine-5-carboxamide (100 mg, 0.26 mmol) was dissolved in 4 mL NMP. To the mixture were added DIEA (140 µL, 0.78 mmol) and then 2,2-difluoroethyl trifluoromethanesulfonate (200 µL). The mixture was stirred at 40° C. for 2 h and quenched with TFA. It was diluted with water and subjected to reverse-phase prep HPLC to isolate the title compound. MS found for $C_{21}H_{26}F_2N_6O$ as $(M+H)^+$=417.4. UV: =268 nm.

Example 66: 4-(Cyclopropylamino)-2-((4-(1-formylpiperidin-4-yl)phenyl)amino)pyrimidine-5-carboxamide

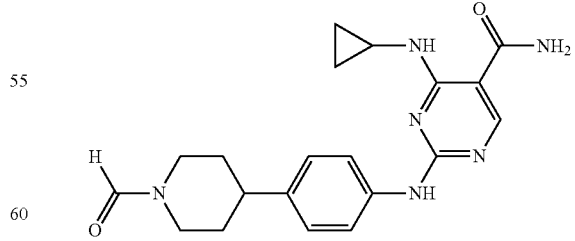

4-(Cyclopropylamino)-2-((4-(piperidin-4-yl)phenyl)amino)pyrimidine-5-carboxamide (100 mg, 0.26 mmol) was dissolved in 4 mL DMF with DIEA (200 µL). The mixture was stirred in a sealed tube at 120° C. for 1 day. It was diluted with water, acidified with TFA and subjected to reverse-phase prep HPLC to isolate the title compound. MS found for $C_{20}H_{24}N_6O_2$ as $(M+H)^+=381.3$. UV: =273 nm.

Example 67: 4-(Cyclopropylamino)-2-((4-(1-(1,3-difluoropropan-2-yl)piperidin-4-yl)phenyl amino)pyrimidine-5-carboxamide

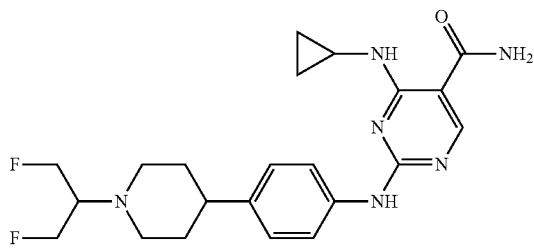

The title compound was synthesized in a manner similar to that described in Example 17 (i.e., 4-(cyclopropylamino)-2-((4-(1-isopropylpiperidin-4-yl)phenyl)amino)pyrimidine-5-carboxamide), but using 1,3-difluoroacetone. MS found for $C_{22}H_{28}F_2N_6O$ as $(M+H)^++=431.4$. UV: $\lambda=268$ nm.

Example 68: 4-(Cyclopropylamino)-2-((4-(1-(2-fluoroethyl)piperidin-4-yl)phenyl)amino)pyrimidine-5-carboxamide

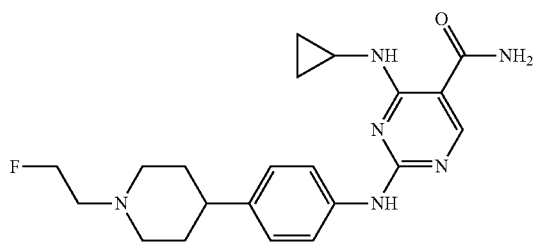 [SMILES: NC(=O)c1cnc(Nc2ccc(C3CCN(CC(F)F)CC3)cc2)nc1NC1CC1]

4-(Cyclopropylamino)-2-((4-(piperidin-4-yl)phenyl)amino)pyrimidine-5-carboxamide (100 mg, 0.26 mmol) was dissolved in 3 mL NMP. To the mixture were added DIEA (140 μL, 0.78 mmol) and 1-bromo-2-fluoroethane (300 mg, in three 100-mg portions in 1 day). It was diluted with water, acidified with TFA and subjected to reverse-phase prep HPLC to isolate the title compound. MS found for $C_{21}H_{27}FN_6O$ as $(M+H)^+=399.4$. UV: $\lambda=268$ nm.

Example 69: 5-(Cyclopropylamino)-3-((4-(1-propionylpiperidin-4-yl)phenyl)amino)-1,2,4-triazine-6-carboxamide

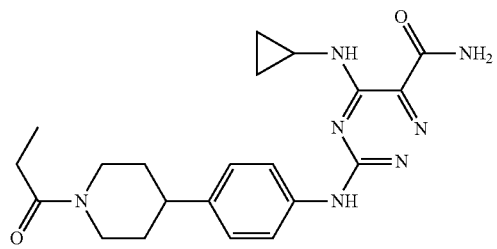 [SMILES: CCC(=O)N1CCC(c2ccc(NC(=N)/N=C(/NC3CC3)C(=N)C(N)=O)cc2)CC1]

Ethyl 3-(methylthio)-5-oxo-4,5-dihydro-1,2,4-triazine-6-carboxylate was prepared according to a known procedure (Huang, J. J., J. Org. Chem 1985, 50, 2293). This compound (500 mg, 2.15 mmol) was dissolved in 15 mL dry acetonitrile. To the mixture were added DIEA (450 μL, 2.58 mmol) and then cyclopropylamine (178 μL, 2.58 mmol). The mixture was stirred for 5 min at room temperature (RT). Then 20 mL commercial 7N $NH_3$/MeOH solution was added. The mixture was stirred overnight, concentrated in vacuo and subjected to flash column with 0%-7% MeOH in DCM to isolate 5-(cyclopropylamino)-3-(methylthio)-1,2,4-triazine-6-carboxamide (360 mg, 74% yield). This intermediate (50 mg, 0.22 mmol) was dissolved in 4 mL NMP. To the mixture was added mCPBA (101 mg, 0.44 mmol). The mixture was stirred at room temperature for 40 min. To the mixture was then added 1-(4-(4-aminophenyl)piperidin-1-yl)propan-1-one (102 mg, 0.44 mmol). The mixture was stirred at 115° C. for 2 h. It was cooled to RT, diluted with EtOAc, washed with 1N NaOH solution and then with water, concentrated in vacuo, and subjected to reverse-phase prep HPLC to isolate the title compound. MS found for $C_{21}H_{27}N_7O_2$ as $(M+H)^+=410.4$. UV: $\lambda=274$ nm.

Example 70: 5-(Cyclopropylamino)-3-((4-(4-(ethylsulfonyl)piperazin-1-yl)phenyl)amino)-1,2,4-triazine-6-carboxamide

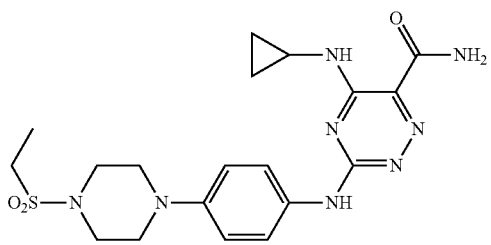

The title compound was synthesized in a manner similar to that described in Example 5-(Cyclopropylamino)-3-((4-(1-propionylpiperidin-4-yl)phenyl)amino)-1,2,4-triazine-6-carboxamide using 4-(4-(ethylsulfonyl)piperazin-1-yl)aniline. MS found for $C_{19}H_{26}N_8O_3S$ as $(M+H)^+=447.4$. UV: $\lambda=232, 288$ nm.

Example 71: 5-(Cyclopropylamino)-3-((1,2,3,4-tetrahydronaphthalen-2-yl)amino)-1,2,4-triazine-6-carboxamide

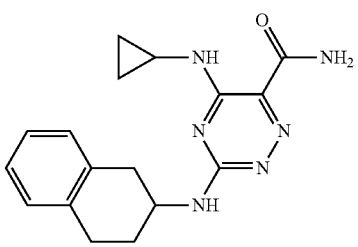 [SMILES: NC(=O)c1nnc(NC2CCc3ccccc3C2)nc1NC1CC1]

5-(Cyclopropylamino)-3-(methylthio)-1,2,4-triazine-6-carboxamide (50 mg, 0.22 mmol) was dissolved in 4 mL NMP. To the mixture was added MCPBA (101 mg, 0.44 mmol). The mixture was stirred at room temperature for 20 min. To the mixture was then added DIEA (310 μL, 1.76 mmol) and 1,2,3,4-tetrahydronaphthalen-2-amine hydrochloride (80 mg, 0.44 mmol). The mixture was stirred at 115° C. for 1.5 h. It was cooled to RT, diluted with EtOAc, washed with 1N NaOH solution and then with water, concentrated in vacuo, and subjected to reverse-phase prep HPLC to isolate the title compound. MS found for $C_1H_{20}N_6O$ as $(M+H)^+=325.2$. UV: $\lambda=237, 302$ nm.

Examples 71-77

The following compounds were synthesized in a manner similar to that described above.

| Example No. | Structure | MW | (M + H)+ | Compound Name |
|---|---|---|---|---|
| 71 | 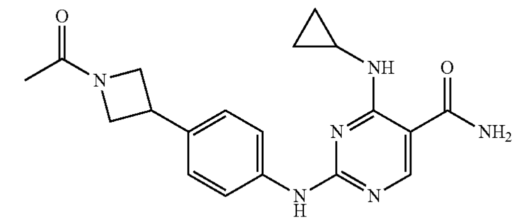 [SMILES: CC(=O)N1CC(c2ccc(Nc3ncc(C(N)=O)c(NC4CC4)n3)cc2)C1] | 366.425 | 367.3 | 2-(4-(1-acetylazetidin-3-yl)phenylamino)-4-(cyclopropylamino)pyrimidine-5-carboxamide |
| 72 | 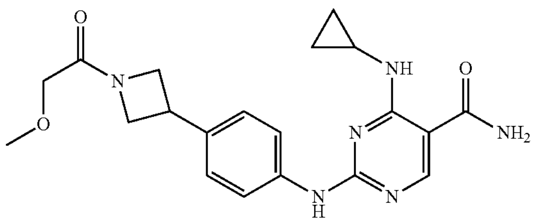 [SMILES: COCC(=O)N1CC(c2ccc(Nc3ncc(C(N)=O)c(NC4CC4)n3)cc2)C1] | 396.451 | 397.3 | 4-(cyclopropylamino)-2-(4-(1-(2-methoxyacetyl)azetidin-3-yl)phenylamino)pyrimidine-5-carboxamide |
| 73 | 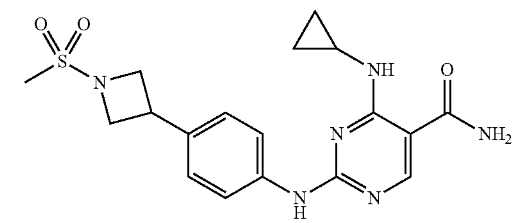 [SMILES: CS(=O)(=O)N1CC(c2ccc(Nc3ncc(C(N)=O)c(NC4CC4)n3)cc2)C1] | 402.477 | 403.3 | 4-(cyclopropylamino)-2-(4-(1-(methylsulfonyl)azetidin-3-yl)phenylamino)pyrimidine-5-carboxamide |
| 74 | 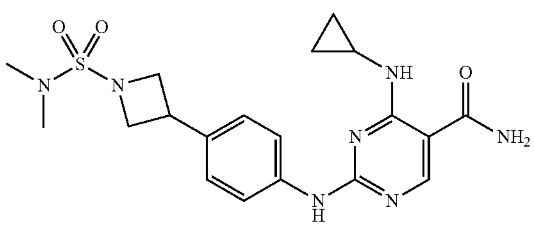 [SMILES: CN(C)S(=O)(=O)N1CC(c2ccc(Nc3ncc(C(N)=O)c(NC4CC4)n3)cc2)C1] | 431.519 | 432.4 | 4-(cyclopropylamino)-2-(4-(1-(N,N-dimethylsulfamoyl)azetidin-3-yl)phenylamino)pyrimidine-5-carboxamide |
| 75 | 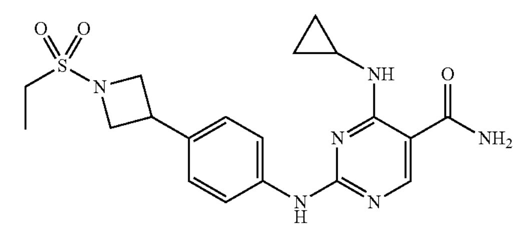 [SMILES: CCS(=O)(=O)N1CC(c2ccc(Nc3ncc(C(N)=O)c(NC4CC4)n3)cc2)C1] | 416.504 | 471.3 | 4-(cyclopropylamino)-2-(4-(1-(ethylsulfonyl)azetidin-3-yl)phenylamino)pyrimidine-5-carboxamide |
| 76 | 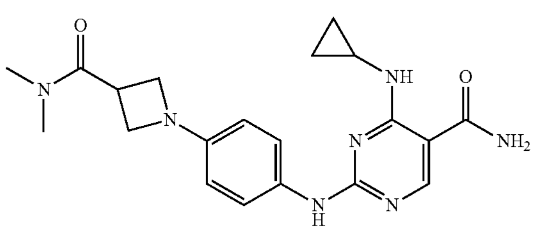 [SMILES: CN(C)C(=O)C1CN(c2ccc(Nc3ncc(C(N)=O)c(NC4CC4)n3)cc2)C1] | 395.467 | 396.3 | 4-(cyclopropylamino)-2-(4-(3-(dimethylcarbamoyl)azetidin-1-yl)phenylamino)pyrimidine-5-carboxamide |
| 77 | 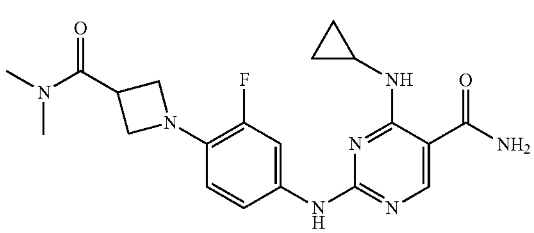 [SMILES: CN(C)C(=O)C1CN(c2ccc(Nc3ncc(C(N)=O)c(NC4CC4)n3)cc2F)C1] | 413.457 | 414.3 | 4-(cyclopropylamino)-2-(4-(3-(dimethylcarbamoyl)azetidin-1-yl)-3-fluorophenylamino)pyrimidine-5-carboxamide |

Example 78: Kinase Assay Protocols

JAK and SYK tyrosine phosphorylation activity is measured using the Z'-LYTE™ Technology developed by Invitrogen Corporation (Carlsbad, Calif.). For JAK1, JAK2 and JAK3 the Z'-LYTE™ Kinase Assay Kit-Tyr6 Peptide (part number PV4122) was used. The Z'-LYTE™ biochemical assay employs a fluorescence resonance energy transfer (FRET) coupled-enzyme format and is based on the differential sensitivity of phosphorylated and non-phosphorylated peptides to proteolitic cleavage. The assay uses a synthetic peptide substrate that is labelled with a donor fluorophore (coumarin) and an acceptor fluorophore (fluorescein) that make up a FRET pair. In the primary reaction (the Kinase Reaction), the kinase transfers the γ-phosphate of ATP to a single tyrosine residue on the substrate, while the presence of a kinase inhibitor in the primary reaction suppresses phosphorylation. In the secondary reaction (the Development Reaction), a site-specific protease (the Development Reagent) is added. The development buffer quenches the Kinase Reaction, while the protease recognizes and cleaves non-phosphorylated Z'-LYTE™ peptide substrate. Cleavage disrupts FRET between the donor and acceptor fluorophores on the non-phosphorylated substrate, while uncleaved, phosphorylated substrate maintains FRET.

To test the ability of candidate molecules to inhibit JAK tyrosine phosphorylation activity, molecules are reconstituted in 100% DMSO and serially diluted 1:10 in polypropylene v-bottom microtiter plates. The candidate molecules are then diluted 1:25 into kinase buffer and 2.5 µl transferred into duplicate wells of a 384 well low volume black microtiter assay plate (Corning, USA). The final DMSO concentration in the assay is 1%. The kinase reaction contains 2.5 µl of a candidate molecule, 5 µl of catalytic domain recombinant Kinase enzyme+Tyr peptide substrate (Invitrogen, CA) and 2.5 µl ATP (Invitrogen, CA). The kinase reaction is allowed to precede for 1 hour at room temperature. The protease reaction is initiated by the addition of 5 µl Development Reagent (Invitrogen, CA). After 1 hour incubation at room temperature the fluorescence is measured using a FlexStation plate reader (Molecular Devices, Sunnyvale, Calif.). The reader settings used are as follows: Fluorescence mode, endpoint, top read, excitation 400 nm, emission 445 nm and 520 nm. Auto Cutoff 435 nm and 515 nm, PMT sensitivity high, 6 reads per well. Inhibition of JAK activity is calculated as the percent phosphorylation of substrate in the presence of inhibitor compared to the percent phosphorylation of substrate in the absence of inhibitor. IC50's are derived using Xlfit 4.3 (IDBS, UK), 4 parameter logistic model 205: $Y=(A+((B-A)/(1+((C/x)^D))))$.

Potency of candidate molecules for inhibiting Syk tyrosine phosphorylation activity is assessed by measuring the ability of a test compound to inhibit Syk-mediated tyrosine phosphorylation of a Syk-specific substrate.

SYK tyrosine phosphorylation activity is measured using the LANCE™ Technology developed by Perkin Elmer Life and Analytical Sciences (Boston, Mass.). LANCE™ refers to homogeneous time resolved fluorometry applications using techniques such as time-resolved fluorescence resonance energy transfer assay (TR-FRET) (see generally for procedures in Perkin Elmer Application Note—How to Optimize a Tyrosine Kinase Assay Using Time Resolved Fluorescence-Based LANCE Detection, wwww.perkinelmer.com/lifesciences). The assay principle involves detection of a phosphorylated substrate using energy transfer from a phosphospecific europium-labeled antibody to streptavidin-allophycocyanin as an acceptor.

To test the ability of candidate molecules to inhibit SYK tyrosine phosphorylation activity, molecules are reconstituted in 30% DMSO and serially diluted 1:3 with the final dilution containing DMSO in the absence of the candidate molecule. The final DMSO concentration in the assay is 3%. Kinase assays are performed as a two part reaction. The first reaction is a kinase reaction that comprises a candidate molecule, full length active recombinant SYK enzyme (Millipore, CA) and biotin-labeled SYK-specific substrate biotin-DEEDYESP-OH. The second reaction involves termination of the kinase reaction and the simultaneous addition of the detection reagents-europium-labeled anti-phosphotyrosine reagent (Eu-W1024-PY100, Perkin Elmer, Boston, Mass.) and Streptavidin-Allophycocyanin detection reagent (SA-APC, Prozyme, CA). The kinase reaction is performed in a black U-bottom 96-well microtitre plate. The final reaction volume is 50 µL and contains a final concentration of 1 nM active SYK enzyme, 550 nM SYK-substrate, and 100 µM ATP diluted in a buffer containing 50 mM Tris pH 7.5, 5 mM $MgCl_2$, and 1 mM DTT. The reaction is allowed to proceed for 1 hour at room temperature. The stop buffer contains 100 mM Tris pH 7.5, 300 mM $NaCl_2$, 20 mM EDTA, 0.02% Brij35, and 0.5% BSA. The detection reagents are added to the reaction mixture at the following dilutions—1:500 for Eu-W1024-PY100 and 1:250 for SA-APC. The kinase reaction is terminated by the addition of 50 µL stop buffer containing the detection reagents. The detection is allowed to proceed for 1 hr at room temperature. Detection of the phosphorolated substrate in the absence and presence of inhibitors is measured in the TR-FRET instrument, Analyst HT (Molecular Probes, Sunnyvale, Calif.) and the condition for measurements are set up using Criterion-Host Release 2.0 (Molecular Probes, Sunnyvale, Calif.). The settings used are a follows: excitation 360 nm, emission 665-7.5 nm, beam splitter 350 nm 50/50, flash 100 pulses, delay 60 us, integration 400 us, z-height 2 mm. Inhibition of SYK-tyrosine kinase activity is calculated as the maximum response observed in the presence of inhibitor, compared to that in the absence of inhibitor. $IC_{50}$s are derived by non-linear regression analysis.

Inhibition of IL4-induced phospho STAT6 formation was measured by pre-incubating 0.5 million Ramos B lymphocytes (ATCC) with 5 µl compound or DMSO vehicle for 1 hour at 37° C./5% $CO_2$. Cells were activated by addition of 1 ng/ml [f] IL4 (R & D Research Systems) for 10 min at 37° C./5% $CO_2$ and then fixed by addition of 1.6% [f] PFA (Electron Microscopy Services). Following a PBS wash step and permeabilization with 100% methanol, cells were incubated with ALEXA-conjugated anti-phosphoSTAT6 (Y641) antibody (BD 612600). The extent of cell associated-fluorescence was determined by flow cytometry and data expressed as mean fluorescent intensity. The extent of inhibition of the IL4-induced STAT6 Y694 activation was measured.

In the tables below, activity in the biochemical assays is provided as follows: +=IC50>1.0 uM; ++=1.0 uM<IC50<0.10 uM, +++=0.10 uM<IC50<0.01 uM, ++++= 0.01 uM<IC50<0.001 uM, +++++=IC50<0.001 uM. "uM" is an alternative form of micromolar (i.e., µM).

TABLE 1

Syk and JAK1 IC50 Assay Results

| Compound No. | Syk IC50 % Inhibition | JAK1 IC50 % Inhibition |
| --- | --- | --- |
| 1 | +++ | +++ |
| 2 | +++ | +++ |
| 3 | +++ | +++ |
| 4 | +++ | +++ |
| 5 | +++ | +++ |
| 6 | +++ | +++ |
| 7 | +++ | +++ |

TABLE 1-continued

Syk and JAK1 IC50 Assay Results

| Compound No. | Syk IC50 % Inhibition | JAK1 IC50 % Inhibition |
|---|---|---|
| 8 | +++ | +++ |
| 9 | +++ | +++ |
| 10 | +++ | +++ |
| 11 | +++ | ++ |
| 12 | ++ | +++ |
| 13 | ++ | +++ |
| 14 | +++ | +++ |
| 15 | +++ | +++ |
| 16 | ++ | + |
| 17 | ++ | +++ |
| 25 | +++ | +++ |
| 41 | +++ | +++ |
| 42 | +++ | +++ |
| 43 | +++ | ++ |
| 43 | +++ | ++ |
| 47 | ++ | +++ |
| 48 | ++ | ++ |
| 49 | ++ | ++ |
| 50 | ++ | + |
| 51 | ++ | +++ |
| 52 | +++ | +++ |
| 53 | +++ | +++ |
| 54 | +++ | +++ |
| 55 | +++ | +++ |
| 56 | +++ | +++ |
| 57 | +++ | +++ |
| 58 | +++ | +++ |
| 59 | +++ | ++ |
| 63 | ++ | + |
| 67 | + | ++ |
| 68 | + | + |
| 69 | +++ | +++ |
| 71 | +++ | |
| 72 | +++ | |
| 73 | +++ | |
| 74 | +++ | |
| 75 | +++ | |
| 76 | ++ | |
| 77 | ++ | |

TABLE 2

JAK2 and JAK3 IC50 Assay Results

| Compound No. | JAK2 IC50 % Inhibition | JAK3 IC50 % Inhibition |
|---|---|---|
| 1 | ++++ | ++++ |
| 2 | ++++ | ++++ |
| 3 | ++++ | ++++ |
| 4 | +++ | ++++ |
| 5 | ++++ | ++++ |
| 6 | ++++ | ++++ |
| 7 | ++++ | ++++ |
| 8 | ++++ | ++++ |
| 9 | ++++ | ++++ |
| 10 | +++ | ++++ |
| 11 | +++ | +++ |
| 12 | +++ | ++++ |
| 13 | +++ | ++++ |
| 14 | ++++ | ++++ |
| 15 | ++++ | ++++ |
| 16 | ++ | +++ |
| 17 | +++ | +++ |
| 25 | ++++ | ++++ |
| 41 | ++++ | ++++ |
| 42 | ++++ | ++++ |
| 43 | +++ | +++ |
| 47 | ++++ | ++++ |
| 48 | +++ | ++++ |
| 49 | +++ | +++ |
| 50 | ++ | ++ |
| 51 | ++++ | ++++ |
| 52 | ++++ | ++++ |
| 53 | ++++ | ++++ |
| 54 | ++++ | ++++ |
| 55 | ++++ | ++++ |
| 56 | +++ | ++++ |
| 57 | +++ | ++++ |
| 58 | +++ | +++ |
| 59 | ++ | +++ |
| 63 | ++ | ++ |
| 67 | ++ | ++ |
| 68 | + | + |
| 69 | ++++ | ++++ |

All patents, patent applications, publications and presentations referred to herein are incorporated by reference in their entirety. Any conflict between any reference cited herein and the teaching of this specification is to be resolved in favor of the latter. Similarly, any conflict between an art-recognized definition of a word or phrase and a definition of the word or phrase as provided in this specification is to be resolved in favor of the latter.

What is claimed is:

1. A compound of Formula (Ia) (Ic), (IVa), or (IVb):

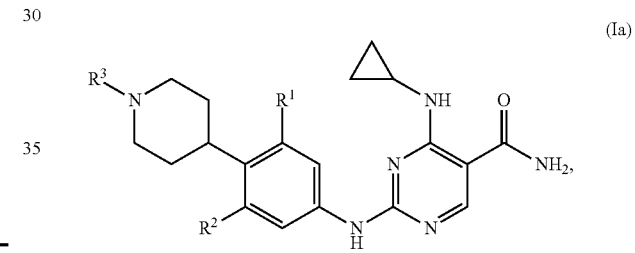

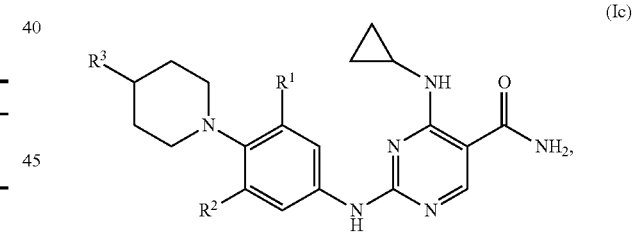

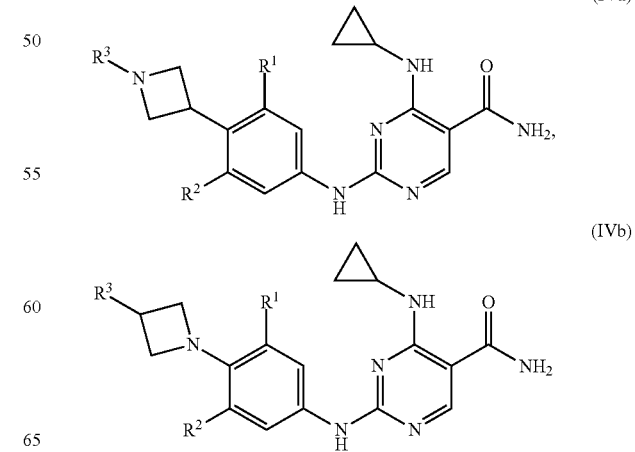

or a tautomer or a pharmaceutically acceptable salt thereof, wherein

R$^1$ is selected from the group consisting of H, halo, C$_{1-4}$ alkoxy, and cyano;

R$^2$ is selected from the group consisting of H, halo, and C$_{1-4}$ alkyl;

R$^3$ is selected from the group consisting of C$_{1-5}$alkyl, haloC$_{1-4}$alkyl, cyanoC$_{1-4}$ alkyl, C$_{3-6}$ cycloalkyl, oxetan-3-yl, 1-cyclopropylpiperidin-4-yl, tetrahydropyran-4-yl, phenyl, pyridin-2-yl, 3-fluoropyridin-2-yl, pyridin-3-yl, HC(O), R$^{3a}$C(O), R$^{3b}$S(O)$_2$, and R$^{3c}$S(O)$_2$;

R$^{3a}$ is selected from the group consisting of ethyl, cyanoC$_{1-4}$ alkyl C$_{1-4}$alkoxy, C$_{1-4}$ alkoxyC$_{1-4}$ alkyl, N-morpholino, tetrahydropyran-4-yl, pyridin-3-yl, C$_{3-6}$ cycloalkyl, 1-cyanocyclopropyl, pyrrolidin-1-yl, and (R$^{3c}$)$_2$N;

R$^{3b}$ is selected from the group consisting of cyclopropyl, pyridin-3-yl, 1-methyl-imidazol-4-yl, 1-methyl-pyrazol-4-yl, ethenyl, and (R$^{3c}$)$_2$N;

each R$^{3c}$ is independently C$_{1-4}$alkyl;

provided that when the compound is represented by formula Ia or formula IVa and R$^3$ is R$^{3c}$S(O)$_2$, then R$^{3c}$ is ethyl or isopropyl; and provided that when the compound is represented by formula Ic or formula IVb, R$^1$ and R$^2$ are not both H.

2. The compound of claim 1, wherein the compound is of Formula (Ia)

or a tautomer or a pharmaceutically acceptable salt thereof.

3. A compound of Formula (Ib):

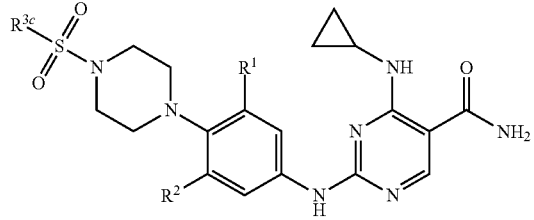

(Ib)

or a tautomer or a pharmaceutically acceptable salt thereof, wherein

R$^1$ is selected from the group consisting of H, halo, C$_{1-4}$ alkoxy, and cyano;

R$^2$ is H or halo; and

R$^{3c}$ is C$_{1-4}$alkyl, wherein

R$^1$ and R$^2$ are not both H.

4. The compound of claim 1, wherein the compound is of Formula (Ic)

or a tautomer or a pharmaceutically acceptable salt thereof.

5. The compound of claim 1 or a tautomer or a pharmaceutically acceptable salt thereof, wherein the compound is selected from the group consisting of the following compounds:

| Structure | Compound Name |
|---|---|
| 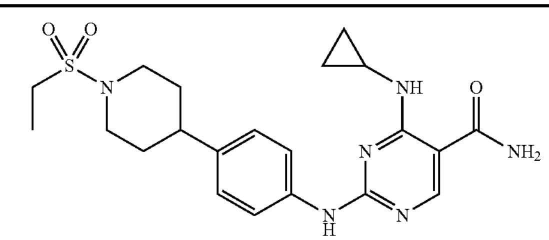 | 4-(cyclopropylamino)-2-((4-(1-(ethylsulfonyl)piperidin-4-yl)phenyl)amino)pyrimidine-5-carboxamide |
| 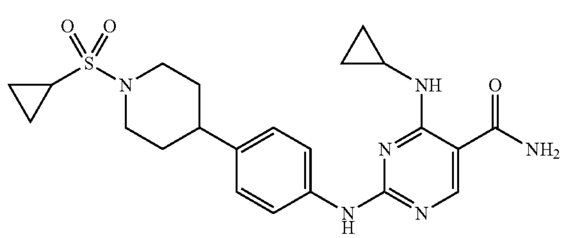 [SMILES: NC(=O)c1cnc(Nc2ccc(C3CCN(S(=O)(=O)C4CC4)CC3)cc2)nc1NC1CC1] | 4-(cyclopropylamino)-2-((4-(1-(cyclopropylsulfonyl)piperidin-4-yl)phenyl)amino)pyrimidine-5-carboxamide |
| 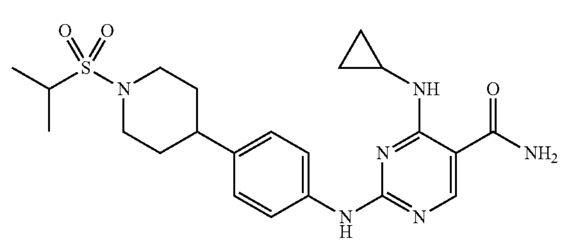 | 4-(cyclopropylamino)-2-((4-(1-(isopropylsulfonyl)piperidin-4-yl)phenyl)amino)pyrimidine-5-carboxamide |

| Structure | Compound Name |
|---|---|
| 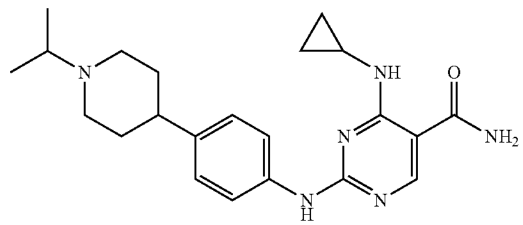 [SMILES: CC(C)N1CCC(c2ccc(Nc3ncc(C(N)=O)c(NC4CC4)n3)cc2)CC1] | 4-(cyclopropylamino)-2-((4-(1-isopropylpiperidin-4-yl)phenyl)amino)pyrimidine-5-carboxamide |
| 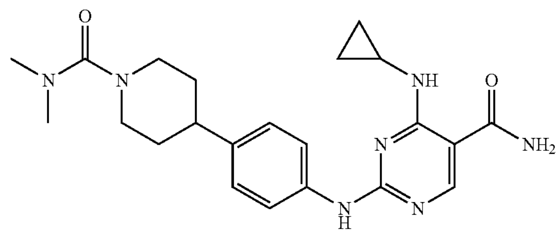 [SMILES: CN(C)C(=O)N1CCC(c2ccc(Nc3ncc(C(N)=O)c(NC4CC4)n3)cc2)CC1] | 4-(cyclopropylamino)-2-((4-(1-(dimethylcarbamoyl)piperidin-4-yl)phenyl)amino)pyrimidine-5-carboxamide |
| 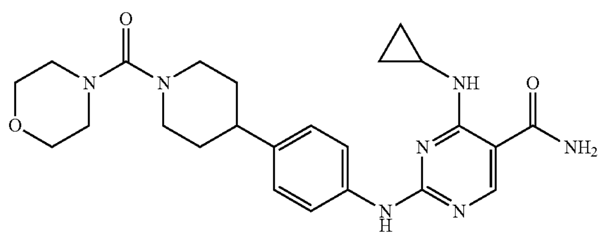 [SMILES: NC(=O)c1cnc(Nc2ccc(C3CCN(C(=O)N4CCOCC4)CC3)cc2)nc1NC1CC1] | 4-(cyclopropylamino)-2-((4-(1-(morpholine-4-carbonyl)piperidin-4-yl)phenyl)amino)pyrimidine-5-carboxamide |
| 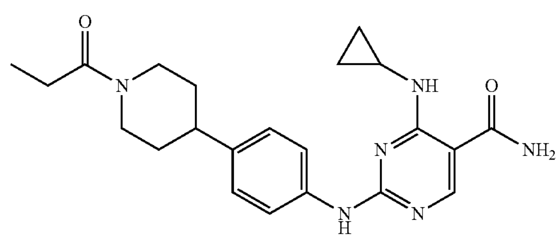 [SMILES: CCC(=O)N1CCC(c2ccc(Nc3ncc(C(N)=O)c(NC4CC4)n3)cc2)CC1] | 4-(cyclopropylamino)-2-((4-(1-propionylpiperidin-4-yl)phenyl)amino)pyrimidine-5-carboxamide |
| 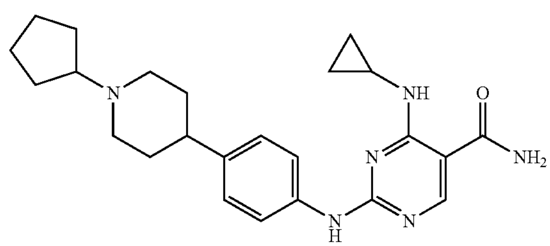 [SMILES: NC(=O)c1cnc(Nc2ccc(C3CCN(C4CCCC4)CC3)cc2)nc1NC1CC1] | 2-((4-(1-cyclopentylpiperidin-4-yl)phenyl)amino)-4-(cyclopropylamino)pyrimidine-5-carboxamide |
| 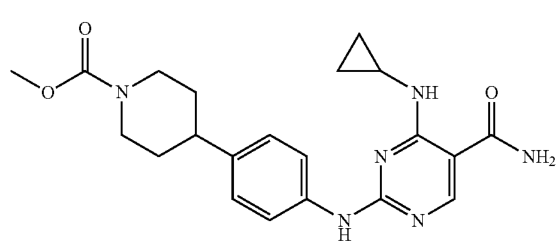 | methyl 4-(4-((5-carbamoyl-4-(cyclopropylamino)pyrimidin-2-yl)amino)phenyl)piperidine-1-carboxylate |

-continued

| Structure | Compound Name |
|---|---|
| 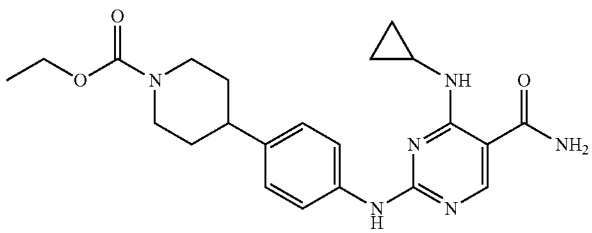 [SMILES: CCOC(=O)N1CCC(c2ccc(Nc3ncc(C(N)=O)c(NC4CC4)n3)cc2)CC1] | ethyl 4-(4-((5-carbamoyl-4-(cyclopropylamino)pyrimidin-2-yl)amino)phenyl)piperidine-1-carboxylate |
| 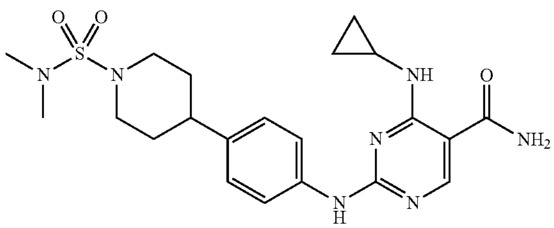 [SMILES: CN(C)S(=O)(=O)N1CCC(c2ccc(Nc3ncc(C(N)=O)c(NC4CC4)n3)cc2)CC1] | 4-(cyclopropylamino)-2-((4-(1-(N,N-dimethylsulfamoyl)piperidin-4-yl)phenyl)amino)pyrimidine-5-carboxamide |
| 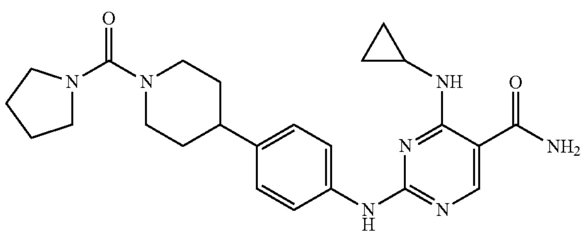 [SMILES: NC(=O)c1cnc(Nc2ccc(C3CCN(C(=O)N4CCCC4)CC3)cc2)nc1NC1CC1] | 4-(cyclopropylamino)-2-((4-(1-(pyrrolidine-1-carbonyl)piperidin-4-yl)phenyl)amino)pyrimidine-5-carboxamide |
| 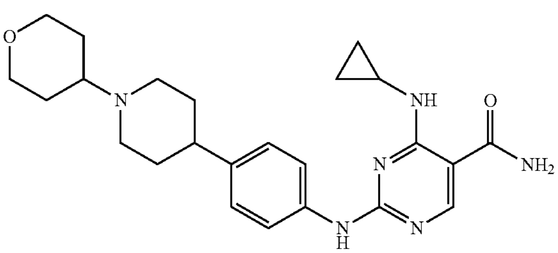 [SMILES: NC(=O)c1cnc(Nc2ccc(C3CCN(C4CCOCC4)CC3)cc2)nc1NC1CC1] | 4-(cyclopropylamino)-2-((4-(1-(tetrahydro-2H-pyran-4-yl)piperidin-4-yl)phenyl)amino)pyrimidine-5-carboxamide |
| 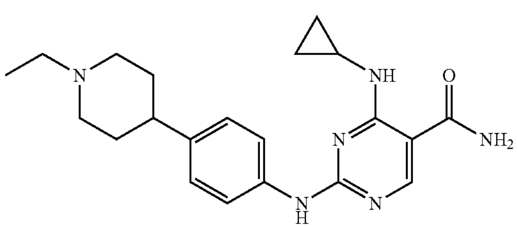 [SMILES: CCN1CCC(c2ccc(Nc3ncc(C(N)=O)c(NC4CC4)n3)cc2)CC1] | 4-(cyclopropylamino)-2-((4-(1-ethylpiperidin-4-yl)phenyl)amino)pyrimidine-5-carboxamide |
| 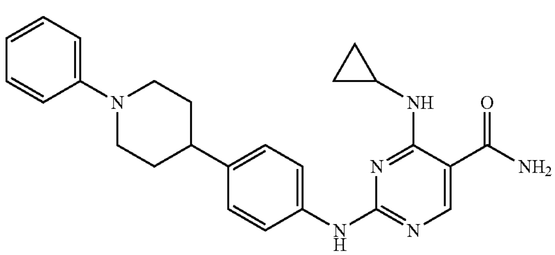 [SMILES: NC(=O)c1cnc(Nc2ccc(C3CCN(c4ccccc4)CC3)cc2)nc1NC1CC1] | 4-(cyclopropylamino)-2-((4-(1-phenylpiperidin-4-yl)phenyl)amino)pyrimidine-5-carboxamide |

| Structure | Compound Name |
|---|---|
| 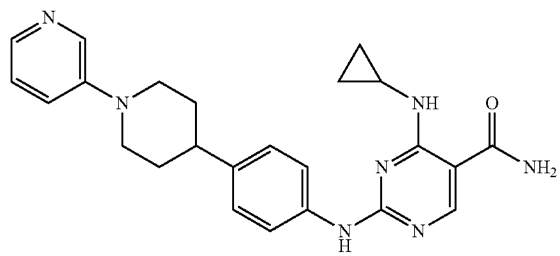 [SMILES: NC(=O)c1cnc(Nc2ccc(C3CCN(c4cccnc4)CC3)cc2)nc1NC1CC1] | 4-(cyclopropylamino)-2-((4-(1-(pyridin-3-yl)piperidin-4-yl)phenyl)amino)pyrimidine-5-carboxamide |
| 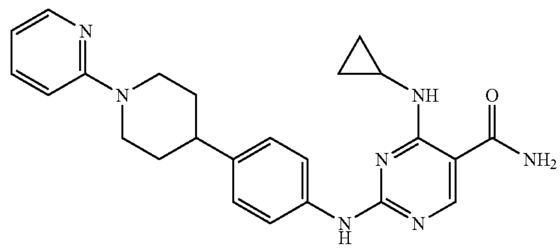 [SMILES: NC(=O)c1cnc(Nc2ccc(C3CCN(c4ccccn4)CC3)cc2)nc1NC1CC1] | 4-(cyclopropylamino)-2-((4-(1-(pyridin-2-yl)piperidin-4-yl)phenyl)amino)pyrimidine-5-carboxamide |
| 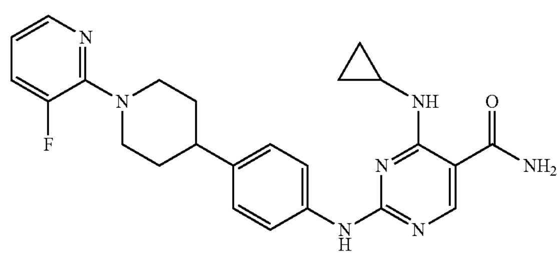 [SMILES: NC(=O)c1cnc(Nc2ccc(C3CCN(c4ncccc4F)CC3)cc2)nc1NC1CC1] | 4-(cyclopropylamino)-2-((4-(1-(3-fluoropyridin-2-yl)piperidin-4-yl)phenyl)amino)pyrimidine-5-carboxamide |
| 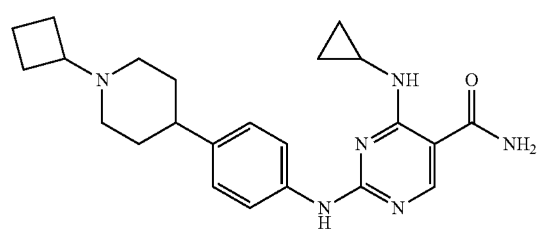 [SMILES: NC(=O)c1cnc(Nc2ccc(C3CCN(C4CCC4)CC3)cc2)nc1NC1CC1] | 2-((4-(1-cyclobutylpiperidin-4-yl)phenyl)amino)-4-(cyclopropylamino)pyrimidine-5-carboxamide |
| 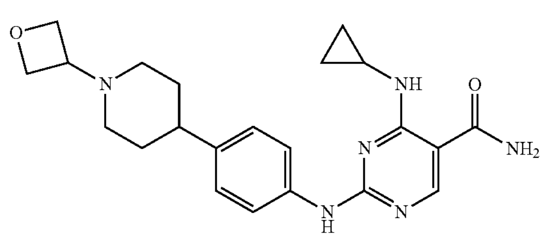 [SMILES: NC(=O)c1cnc(Nc2ccc(C3CCN(C4COC4)CC3)cc2)nc1NC1CC1] | 4-(cyclopropylamino)-2-((4-(1-(oxetan-3-yl)piperidin-4-yl)phenyl)amino)pyrimidine-5-carboxamide |
| 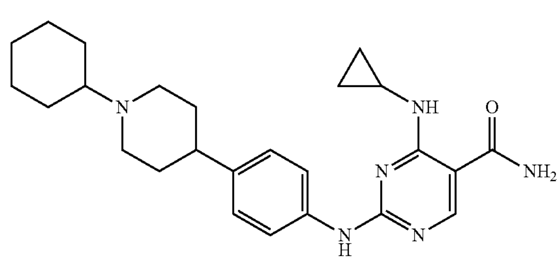 [SMILES: NC(=O)c1cnc(Nc2ccc(C3CCN(C4CCCCC4)CC3)cc2)nc1NC1CC1] | 2-((4-(1-cyclohexylpiperidin-4-yl)phenyl)amino)-4-(cyclopropylamino)pyrimidine-5-carboxamide |

-continued

| Structure | Compound Name |
|---|---|
| 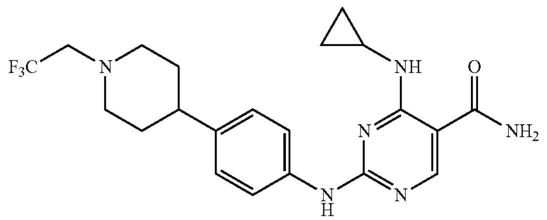 [SMILES: NC(=O)c1cnc(Nc2ccc(C3CCN(CC(F)(F)F)CC3)cc2)nc1NC1CC1] | 4-(cyclopropylamino)-2-((4-(1-(2,2,2-trifluoroethyl)piperidin-4-yl)phenyl)amino)pyrimidine-5-carboxamide |
| 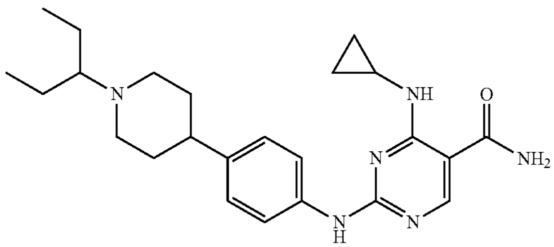 [SMILES: CCC(CC)N1CCC(c2ccc(Nc3ncc(C(N)=O)c(NC4CC4)n3)cc2)CC1] | 4-(cyclopropylamino)-2-((4-(1-(pentan-3-yl)piperidin-4-yl)phenyl)amino)pyrimidine-5-carboxamide |
| 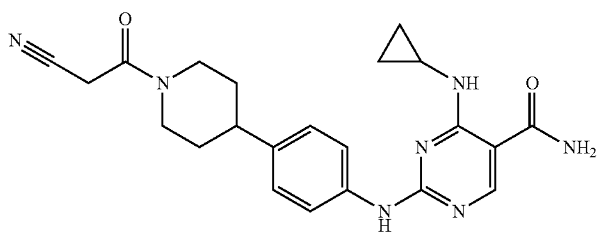 [SMILES: N#CCC(=O)N1CCC(c2ccc(Nc3ncc(C(N)=O)c(NC4CC4)n3)cc2)CC1] | 2-((4-(1-(2-cyanoacetyl)piperidin-4-yl)phenyl)amino)-4-(cyclopropylamino)pyrimidine-5-carboxamide |
| 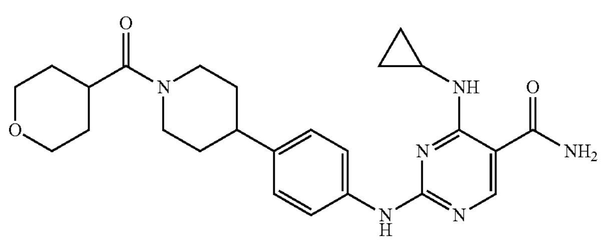 [SMILES: NC(=O)c1cnc(Nc2ccc(C3CCN(C(=O)C4CCOCC4)CC3)cc2)nc1NC1CC1] | 4-(cyclopropylamino)-2-((4-(1-(tetrahydro-2H-pyran-4-carbonyl)piperidin-4-yl)phenyl)amino)pyrimidine-5-carboxamide |
| 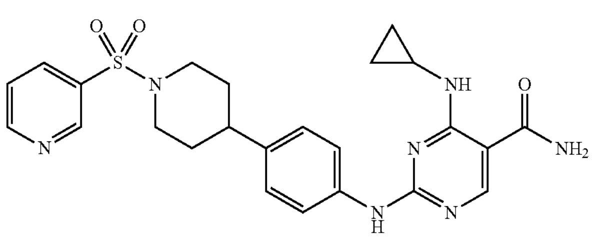 [SMILES: NC(=O)c1cnc(Nc2ccc(C3CCN(S(=O)(=O)c4cccnc4)CC3)cc2)nc1NC1CC1] | 4-(cyclopropylamino)-2-((4-(1-(pyridin-3-ylsulfonyl)piperidin-4-yl)phenyl)amino)pyrimidine-5-carboxamide |
| 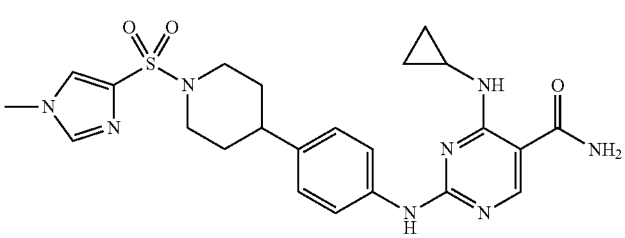 [SMILES: Cn1cnc(S(=O)(=O)N2CCC(c3ccc(Nc4ncc(C(N)=O)c(NC5CC5)n4)cc3)CC2)c1] | 4-(cyclopropylamino)-2-((4-(1-((1-methyl-1H-imidazol-4-yl)sulfonyl)piperidin-4-yl)phenyl)amino)pyrimidine-5-carboxamide |

| Structure | Compound Name |
|---|---|
| 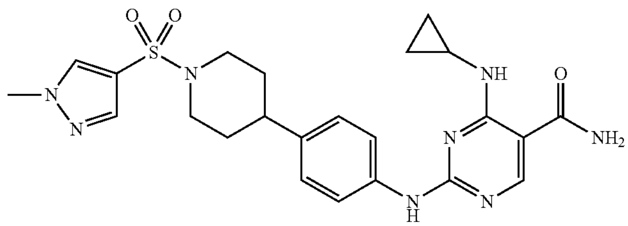 [SMILES: Cn1cc(S(=O)(=O)N2CCC(c3ccc(Nc4ncc(C(N)=O)c(NC5CC5)n4)cc3)CC2)cn1] | 4-(cyclopropylamino)-2-((4-(1-((1-methyl-1H-pyrazol-4-yl)sulfonyl)piperidin-4-yl)phenyl)amino)pyrimidine-5-carboxamide |
| 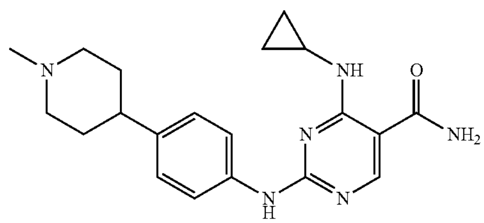 [SMILES: CN1CCC(c2ccc(Nc3ncc(C(N)=O)c(NC4CC4)n3)cc2)CC1] | 4-(cyclopropylamino)-2-((4-(1-methylpiperidin-4-yl)phenyl)amino)pyrimidine-5-carboxamide |
| 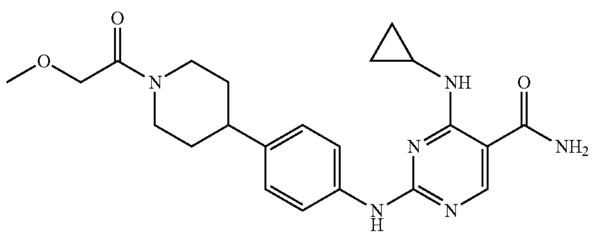 [SMILES: COCC(=O)N1CCC(c2ccc(Nc3ncc(C(N)=O)c(NC4CC4)n3)cc2)CC1] | 4-(cyclopropylamino)-2-((4-(1-(2-methoxyacetyl)piperidin-4-yl)phenyl)amino)pyrimidine-5-carboxamide |
| 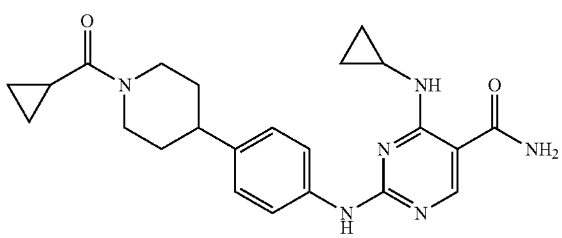 [SMILES: NC(=O)c1cnc(Nc2ccc(C3CCN(C(=O)C4CC4)CC3)cc2)nc1NC1CC1] | 2-((4-(1-(cyclopropanecarbonyl)piperidin-4-yl)phenyl)amino)-4-(cyclopropylamino)pyrimidine-5-carboxamide |
| 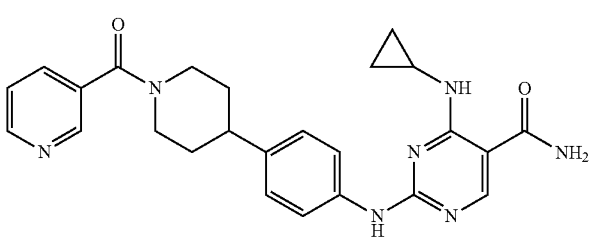 [SMILES: NC(=O)c1cnc(Nc2ccc(C3CCN(C(=O)c4cccnc4)CC3)cc2)nc1NC1CC1] | 4-(cyclopropylamino)-2-((4-(1-nicotinoylpiperidin-4-yl)phenyl)amino)pyrimidine-5-carboxamide |
| 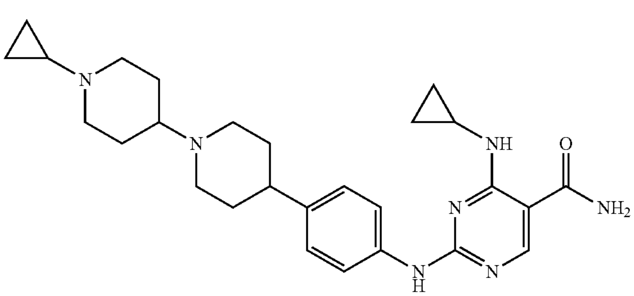 [SMILES: NC(=O)c1cnc(Nc2ccc(C3CCN(C4CCN(C5CC5)CC4)CC3)cc2)nc1NC1CC1] | 2-((4-(1'-cyclopropyl-[1,4'-bipiperidin]-4-yl)phenyl)amino)-4-(cyclopropylamino)pyrimidine-5-carboxamide |

| Structure | Compound Name |
|---|---|
| 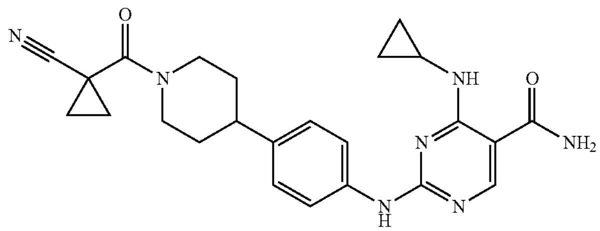 [SMILES: N#CC1(C(=O)N2CCC(c3ccc(Nc4ncc(C(N)=O)c(NC5CC5)n4)cc3)CC2)CC1] | 2-((4-(1-(1-cyanocyclopropanecarbonyl)piperidin-4-yl)phenyl)amino)-4-(cyclopropylamino)pyrimidine-5-carboxamide |
| 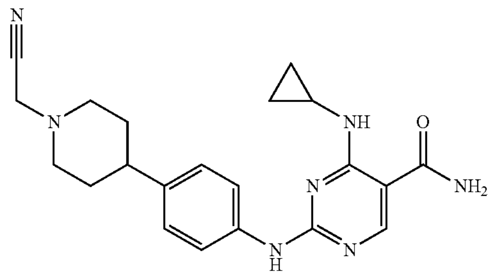 [SMILES: N#CCN1CCC(c2ccc(Nc3ncc(C(N)=O)c(NC4CC4)n3)cc2)CC1] | 2-((4-(1-(cyanomethyl)piperidin-4-yl)phenyl)amino)-4-(cyclopropylamino)pyrimidine-5-carboxamide |
| 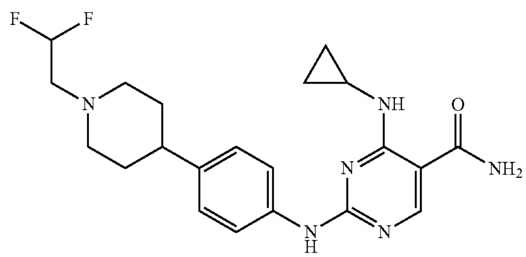 [SMILES: NC(=O)c1cnc(Nc2ccc(C3CCN(CC(F)F)CC3)cc2)nc1NC1CC1] | 4-(cyclopropylamino)-2-((4-(1-(2,2-difluoroethyl)piperidin-4-yl)phenyl)amino)pyrimidine-5-carboxamide |
| 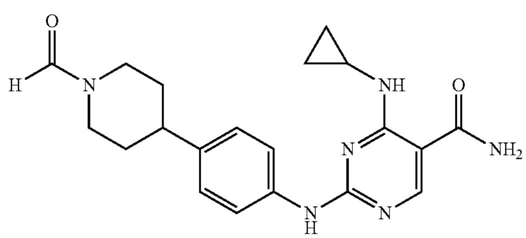 [SMILES: NC(=O)c1cnc(Nc2ccc(C3CCN(C=O)CC3)cc2)nc1NC1CC1] | 4-(cyclopropylamino)-2-((4-(1-formylpiperidin-4-yl)phenyl)amino)pyrimidine-5-carboxamide |
| 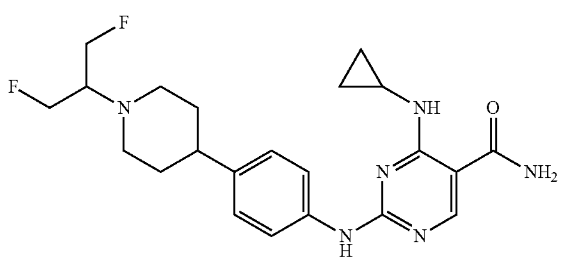 [SMILES: NC(=O)c1cnc(Nc2ccc(C3CCN(C(CF)CF)CC3)cc2)nc1NC1CC1] | 4-(cyclopropylamino)-2-((4-(1-(1,3-difluoropropan-2-yl)piperidin-4-yl)phenyl)amino)pyrimidine-5-carboxamide |
| | 4-(cyclopropylamino)-2-((4-(1-(2-fluoroethyl)piperidin-4-yl)phenyl)amino)pyrimidine-5-carboxamide | or a tautomer or a pharmaceutically acceptable salt thereof.

6. The compound of claim 3, wherein the compound is selected from the group consisting of the following compounds:

| Structure | Compound Name |
|---|---|
| 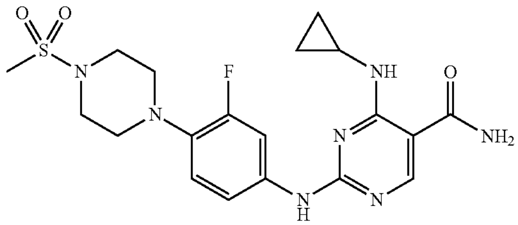 [SMILES: CS(=O)(=O)N1CCN(c2ccc(Nc3ncc(C(N)=O)c(NC4CC4)n3)cc2F)CC1] | 4-(cyclopropylamino)-2-((3-fluoro-4-(4-(methylsulfonyl)piperazin-1-yl)phenyl)amino)pyrimidine-5-carboxamide |
| 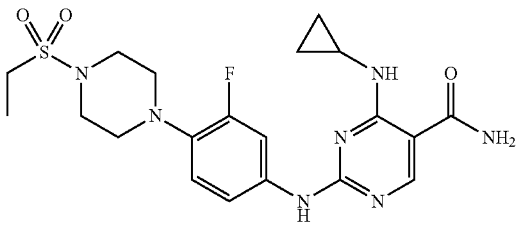 [SMILES: CCS(=O)(=O)N1CCN(c2ccc(Nc3ncc(C(N)=O)c(NC4CC4)n3)cc2F)CC1] | 4-(cyclopropylamino)-2-((4-(4-(ethylsulfonyl)piperazin-1-yl)-3-fluorophenyl)amino)pyrimidine-5-carboxamide |
| 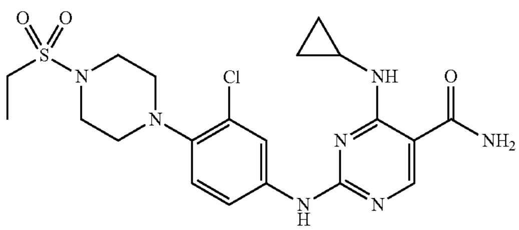 [SMILES: CCS(=O)(=O)N1CCN(c2ccc(Nc3ncc(C(N)=O)c(NC4CC4)n3)cc2Cl)CC1] | 2-((3-chloro-4-(4-(ethylsulfonyl)piperazin-1-yl)phenyl)amino)-4-(cyclopropylamino)pyrimidine-5-carboxamide |
| 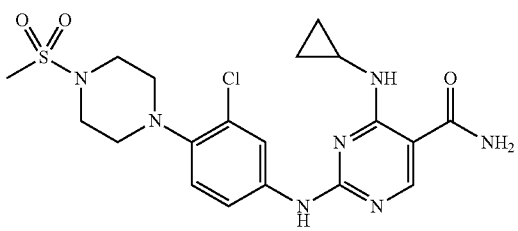 | 2-((3-chloro-4-(4-(methylsulfonyl)piperazin-1-yl)phenyl)amino)-4-(cyclopropylamino)pyrimidine-5-carboxamide |
| 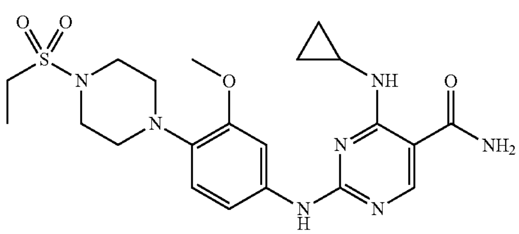 [SMILES: CCS(=O)(=O)N1CCN(c2ccc(Nc3ncc(C(N)=O)c(NC4CC4)n3)cc2OC)CC1] | 4-(cyclopropylamino-2-((4-(4-(ethylsulfonyl)piperazin-1-yl)-3-methoxyphenyl)amino)pyrimidine-5-carboxamide |
| 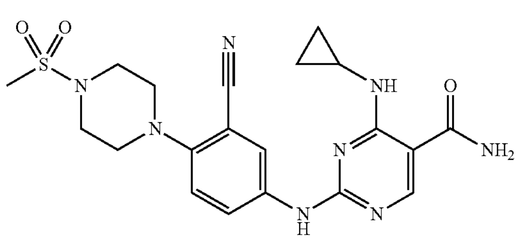 [SMILES: CS(=O)(=O)N1CCN(c2ccc(Nc3ncc(C(N)=O)c(NC4CC4)n3)cc2C#N)CC1] | 2-((3-cyano-4-(4-(methylsulfonyl)piperazin-1-yl)phenyl)amino)-4-(cyclopropylamino)pyrimidine-5-carboxamide |

-continued

| Structure | Compound Name |
|---|---|
| 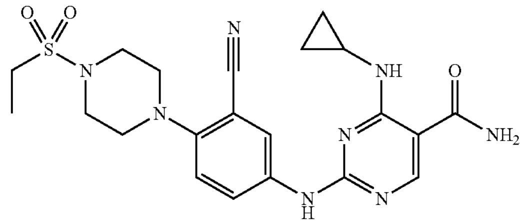 [SMILES: CCS(=O)(=O)N1CCN(c2ccc(Nc3ncc(C(N)=O)c(NC4CC4)n3)cc2C#N)CC1] | 2-((3-cyano-4-(4-(ethylsulfonyl)piperazin-1-yl)phenyl)amino)-4-(cyclopropylamino)pyrimidine-5-carboxamide |
| 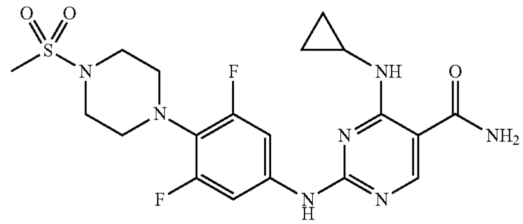 [SMILES: CS(=O)(=O)N1CCN(c2c(F)cc(Nc3ncc(C(N)=O)c(NC4CC4)n3)cc2F)CC1] | 4-(cyclopropylamino)-2-((3,5-difluoro-4-(4-(methylsulfonyl)piperazin-1-yl)phenyl)amino)pyrimidine-5-carboxamide |
| 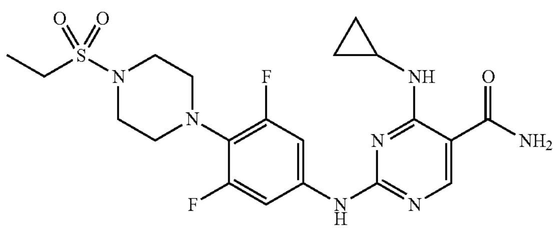 [SMILES: CCS(=O)(=O)N1CCN(c2c(F)cc(Nc3ncc(C(N)=O)c(NC4CC4)n3)cc2F)CC1] | 4-(cyclopropylamino)-2-((4-(4-(ethylsulfonyl)piperazin-1-yl)-3,5-difluorophenyl)amino)pyrimidine-5-carboxamide |
| | 4-(cyclopropylamino)-2-((4-(4-(ethylsulfonyl)piperazin-1-yl)-3-methoxyphenyl)amino)pyrimidine-5-carboxamide | or a tautomer or a pharmaceutically acceptable salt thereof.

7. The compound of claim 4, wherein the compound is selected from the group consisting of the following compounds:

| Structure | Compound Name |
|---|---|
| 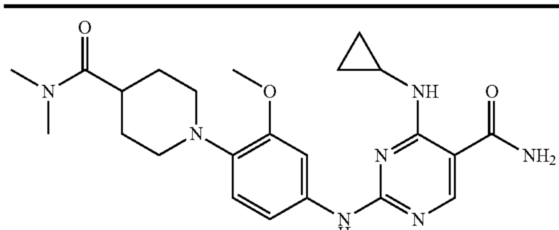 | 4-(cyclopropylamino)-2-((4-(4-(dimethylcarbamoyl)piperidin-1-yl)-3-methoxyphenyl)amino)pyrimidine-5-carboxamide |

| Structure | Compound Name |
|---|---|
| 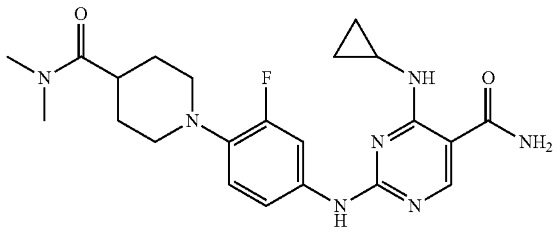 [SMILES: CN(C)C(=O)C1CCN(c2ccc(Nc3ncc(C(N)=O)c(NC4CC4)n3)cc2F)CC1] | 4-(cyclopropylamino)-2-((4-(4-(dimethylcarbamoyl)piperidin-1-yl)-3-fluorophenyl)amino)pyrimidine-5-carboxamide |
| | 2-((3-chloro-4-(4-(dimethylcarbamoyl)piperidin-1-yl)phenyl)amino)-4-(cyclopropylamino)pyrimidine-5-carboxamide | or a tautomer or a pharmaceutically acceptable salt thereof.

8. A compound of Formula (II):

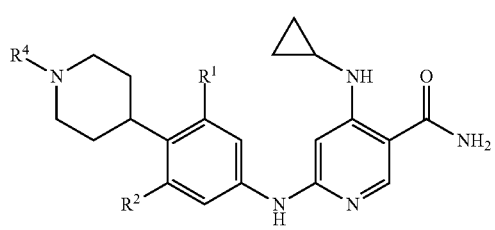

(II)

or a tautomer or a pharmaceutically acceptable salt thereof, wherein $R^1$ is selected from the group consisting of H, halo, $C_{1-4}$alkoxy, and cyano;

$R^2$ is selected from the group consisting of H, halo, and $C_{1-4}$alkyl;

$R^4$ is selected from the group consisting of H and $C_{1-4}$alkylS(O)$_2$.

9. The compound of claim 8, wherein the compound is selected from the group consisting of the following compounds:

| Structure | Compound Name |
|---|---|
| 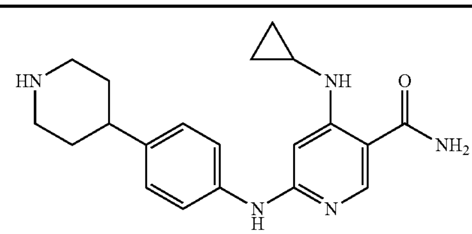 | 4-(cyclopropylamino)-6-((4-(piperidin-4-yl)phenyl)amino)nicotinamide |
| | 4-(cyclopropylamino)-6-((4-(1-(ethylsulfonyl)piperidin-4-yl)phenyl)amino)nicotinamide | or a tautomer or a pharmaceutically acceptable salt thereof.

10. A compound of Formula (III):

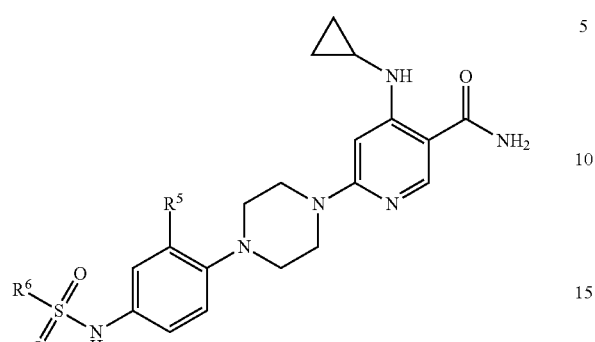

(III)

or a tautomer or a pharmaceutically acceptable salt thereof, wherein $R^5$ is selected from the group consisting of H and $C_{1-4}$alkoxy; and $R^6$ is $C_{1-4}$alkyl.

11. The compound of claim 10, wherein the compound is selected from the group consisting of the following compounds:

| Structure | Compound Name |
|---|---|
| 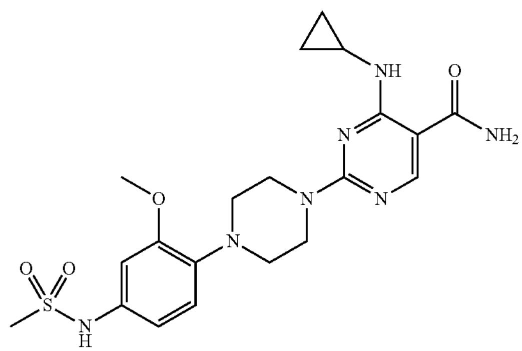 [SMILES: COc1cc(NS(C)(=O)=O)ccc1N1CCN(c2ncc(C(N)=O)c(NC3CC3)n2)CC1] | 4-(cyclopropylamino)-2-(4-(2-methoxy-4-(methylsulfonamido)phenyl)piperazin-1-yl)pyrimidine-5-carboxamide |
| | 4-(cyclopropylamino)-2-(4-(4-(ethylsulfonamido)-2-methoxyphenyl)piperazin-1-yl)pyrimidine-5-carboxamide | or a tautomer or a pharmaceutically acceptable salt thereof.

12. A compound that is selected from the group consisting of the following compounds:

| Structure | Compound Name |
|---|---|
| 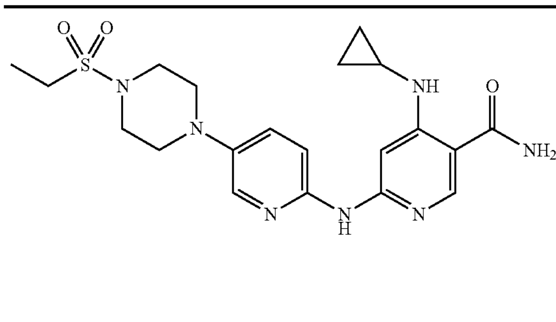 | 4-(cyclopropylamino)-2-((5-(4-(ethylsulfonyl)piperazin-1-yl)pyridin-2-yl)amino)pyrimidine-5-carboxamide |

-continued

| Structure | Compound Name |
|---|---|
| | 6-(cyclopropylamino)-4-((4-(piperidin-4-yl)phenyl)amino)nicotinamide | or a tautomer or a pharmaceutically acceptable salt thereof.

13. The compound of claim 1, wherein the compound is of Formula (IVa)

or a tautomer or a pharmaceutically acceptable salt thereof.

14. The compound of claim 1, wherein the compound is of Formula (IVb)

or a tautomer or a pharmaceutically acceptable salt thereof.

15. A compound of claim 1 selected from the group consisting of the following compounds:

| Structure | Compound Name |
|---|---|
| 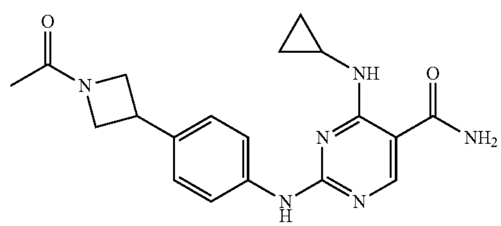 [SMILES: CC(=O)N1CC(c2ccc(Nc3ncc(C(N)=O)c(NC4CC4)n3)cc2)C1] | 2-(4-(1-acetylazetidin-3-yl)phenylamino)-4-(cyclopropylamino)pyrimidine-5-carboxamide |
| 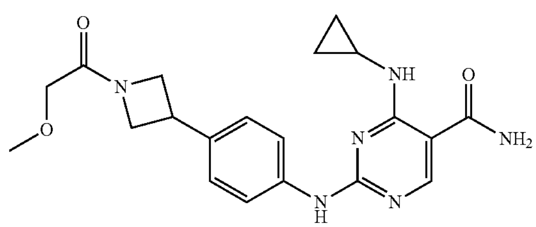 [SMILES: COCC(=O)N1CC(c2ccc(Nc3ncc(C(N)=O)c(NC4CC4)n3)cc2)C1] | 4-(cyclopropylamino)-2-(4-(1-(2-methoxyacetyl)azetidin-3-yl)phenylamino)pyrimidine-5-carboxamide |
| 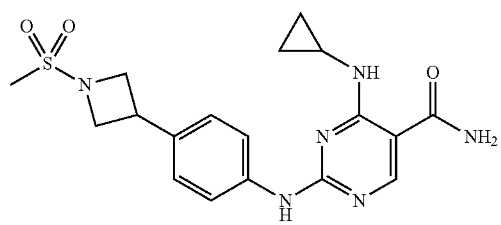 [SMILES: CS(=O)(=O)N1CC(c2ccc(Nc3ncc(C(N)=O)c(NC4CC4)n3)cc2)C1] | 4-(cyclopropylamino)-2-(4-(1-(methylsulfonyl)azetidin-3-yl)phenylamino)pyrimidine-5-carboxamide |
| 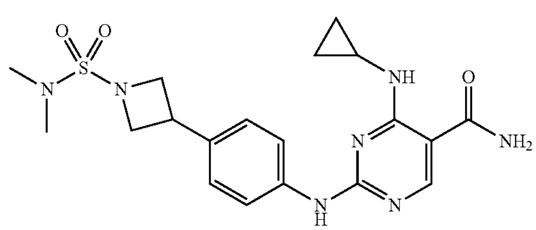 [SMILES: CN(C)S(=O)(=O)N1CC(c2ccc(Nc3ncc(C(N)=O)c(NC4CC4)n3)cc2)C1] | 4-(cyclopropylamino)-2-(4-(1-(N,N-dimethylsulfamoyl)azetidin-3-yl)phenylamino)pyrimidine-5-carboxamide |

| Structure | Compound Name |
|---|---|
| (structure) | 4-(cyclopropylamino)-2-(4-(1-(ethylsulfonyl)azetidin-3-yl)phenylamino)pyrimidine-5-carboxamide |
| (structure) | 4-(cyclopropylamino)-2-(4-(3-(dimethylcarbamoyl)azetidin-1-yl)phenylamino)pyrimidine-5-carboxamide |
| (structure) | 4-(cyclopropylamino)-2-(4-(3-(dimethylcarbamoyl)azetidin-1-yl)-3-fluorophenylamino)pyrimidine-5-carboxamide | or a tautomer or a pharmaceutically acceptable salt thereof.

16. A composition comprising a compound of claim 1 in combination with a pharmaceutically acceptable carrier or diluent.

17. A method for inhibiting Syk or JAK kinase, wherein the method comprises contacting a cell with a compound of claim 1.

18. A method for treating a condition or disorder mediated at least in part by Syk or JAK kinase activity, wherein the method comprises administering to a subject in need of such treatment a therapeutically effective amount of a composition of claim 16.

19. The method of claim 18, wherein the condition or disorder is selected from the group consisting of cardiovascular disease, inflammatory disease, autoimmune disease, and cell proliferative disorder.

20. The compound of claim 2, or a tautomer or a pharmaceutically acceptable salt thereof, wherein $R^3$ is $R^{3a}C(O)$.

21. The compound of claim 20, or a tautomer or a pharmaceutically acceptable salt thereof, wherein $R^{3a}$ is selected from the group consisting of ethyl, N-morpholino, tetrahydropyran-4-yl, pyridine-3-yl, ethoxymethyl, cyclopropyl, methoxy, ethoxy, pyrrolidine-1-yl, 1-cyanocyclopropyl, dimethylamino, and cyano$C_{1-4}$alkylene.

22. The compound of claim 20, or a tautomer or a pharmaceutically acceptable salt thereof, wherein $R^{3a}$ is ethyl or cyanomethyl.

23. The compound of claim 22, wherein the compound is selected from the group consisting of the following compounds:

| Structure | Compound Name |
|---|---|
| (structure) | 4-(cyclopropylamino)-2-((4-(1-propionylpiperidin-4-yl)phenyl)amino)pyrimidine-5-carboxamide |

| Structure | Compound Name |
|---|---|
| 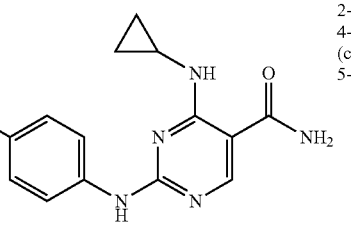 | 2-((4-(1-(2-cyanoacetyl)piperidin-4-yl)phenyl)amino)-4-(cyclopropylamino)pyrimidine-5-carboxamide |
or a tautomer or a pharmaceutically acceptable salt thereof.